US011801226B2

(12) United States Patent
Byröd et al.

(10) Patent No.: US 11,801,226 B2
(45) Date of Patent: *Oct. 31, 2023

(54) PHARMACEUTICAL FORMULATION OF ODEVIXIBAT

(71) Applicant: Albireo AB, Gothenburg (SE)

(72) Inventors: Eva Byröd, Mölndal (SE); Per-Göran Gillberg, Mölndal (SE); Anna-Maria Tivert, Gothenburg (SE); Rikard Bryland, Limhamn (SE); Ann-Charlotte Dahlquist, Lund (SE); Jessica Elversson, Dalby (SE); Nils Ove Gustafsson, Löddeköpinge (SE); Robert Lundqvist, Hälsö (SE); Ingvar Ymen, Saltsjö-Boo (SE); Martin Bohlin, Johanneshov (SE)

(73) Assignee: Albireo AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/113,966

(22) Filed: Dec. 7, 2020

(65) Prior Publication Data

US 2021/0177767 A1 Jun. 17, 2021

Related U.S. Application Data

(63) Continuation of application No. 16/477,160, filed as application No. PCT/SE2019/050603 on Jun. 20, 2019.

(30) Foreign Application Priority Data

Jun. 20, 2018 (SE) ..................................... 1850761-6
Jun. 20, 2018 (SE) ..................................... 1850762-4

(51) Int. Cl.
| | | |
|---|---|---|
| *A61K 31/554* | (2006.01) | |
| *A61K 9/16* | (2006.01) | |
| *A61K 9/50* | (2006.01) | |
| *A61K 9/48* | (2006.01) | |
| *A61K 9/00* | (2006.01) | |

(52) U.S. Cl.
CPC ............ *A61K 9/5047* (2013.01); *A61K 9/009* (2013.01); *A61K 9/4816* (2013.01); *A61K 9/5089* (2013.01); *A61K 31/554* (2013.01)

(58) Field of Classification Search
CPC .. A61K 31/554; A61K 9/1676; A61K 9/5047; A61K 9/5042; A61K 9/167
See application file for complete search history.

(56) References Cited

U.S. PATENT DOCUMENTS

| | | |
|---|---|---|
| 3,539,380 A | 11/1970 | Johnson |
| 4,507,235 A | 3/1985 | Wunsch |
| 5,167,965 A | 12/1992 | Schulz |
| 5,384,130 A * | 1/1995 | Kamada ............... A61K 9/1676 424/461 |
| 5,422,124 A | 6/1995 | Valducci |
| 5,663,165 A | 9/1997 | Brieaddy |
| 5,723,458 A | 3/1998 | Brieaddy et al. |
| 5,811,388 A | 9/1998 | Friend et al. |
| 5,817,652 A | 10/1998 | Brieaddy et al. |
| 5,900,233 A | 5/1999 | Day |
| 5,910,494 A | 6/1999 | Brieaddy |
| 5,976,811 A | 11/1999 | Mullner et al. |
| 5,994,391 A | 11/1999 | Lee et al. |
| 5,998,400 A | 12/1999 | Brieaddy et al. |
| 6,020,330 A | 2/2000 | Enhsen et al. |
| 6,069,167 A | 5/2000 | Sokol |
| 6,277,831 B1 | 8/2001 | Frick et al. |
| 6,346,527 B1 | 2/2002 | Takanaka et al. |
| 6,355,672 B1 | 3/2002 | Yasuma et al. |
| 6,387,924 B2 | 5/2002 | Lee et al. |
| 6,387,944 B1 | 5/2002 | Frick et al. |
| 6,426,340 B1 | 7/2002 | Gibson et al. |
| 6,562,860 B1 | 5/2003 | Keller et al. |
| 6,635,280 B2 | 10/2003 | Shell et al. |
| 6,642,269 B2 | 11/2003 | Frick et al. |
| 6,676,979 B2 | 1/2004 | Marlett et al. |
| 6,784,201 B2 | 8/2004 | Lee et al. |
| 6,906,058 B2 | 6/2005 | Starke et al. |

(Continued)

FOREIGN PATENT DOCUMENTS

| | | |
|---|---|---|
| DE | 3930168 | 3/1991 |
| DE | 19825804 | 8/2000 |

(Continued)

OTHER PUBLICATIONS

Fisher, Elizabeth S. "Milling of active pharmaceutical ingredients." Encyclopedia of Pharmaceutical Technology (2006) 2339-2351.*
Parikh, Dilip M., and David M. Jones. "Batch Fluid Bed Granulation." Handbook of Pharmaceutical Granulation Technology (2010): 204-260. (Year: 2010).*
PCT International Search Report and Written Opinion in Application No. PCT/SE2019/050208, dated Jul. 8, 2019, 15 pages.

(Continued)

*Primary Examiner* — Bethany P Barham
*Assistant Examiner* — Peter Anthopolos
(74) *Attorney, Agent, or Firm* — Fish & Richardson P.C.

(57) ABSTRACT

The invention relates to a pharmaceutical formulation, e.g. a paediatric formulation, of odevixibat, which comprises a plurality of small particles. The formulation may be used in the treatment of liver diseases such as bile acid-dependent liver diseases, and particularly cholestatic liver diseases such as biliary atresia, progressive familial intrahepatic cholestasis (PFIC), Alagille syndrome (ALGS) and paediatric cholestatic pruritus. The invention also relates to a process for the preparation of the pharmaceutical formulation.

15 Claims, 6 Drawing Sheets

Specification includes a Sequence Listing.

(56) References Cited

U.S. PATENT DOCUMENTS

| | | |
|---|---|---|
| 6,943,189 B2 | 9/2005 | Keller et al. |
| 7,125,864 B2 | 10/2006 | Starke et al. |
| 7,132,416 B2 | 11/2006 | Starke et al. |
| 7,132,557 B2 | 11/2006 | Wilkes et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,514,421 B2 | 4/2009 | Abrahamsson et al. |
| 7,615,536 B2 | 11/2009 | Frick et al. |
| 7,767,229 B1 | 8/2010 | Milne et al. |
| 7,923,468 B2 | 4/2011 | Frick et al. |
| 7,939,061 B2 | 5/2011 | Prakash et al. |
| 7,956,085 B2 | 6/2011 | Frick et al. |
| 8,048,413 B2 | 11/2011 | Huguet |
| 8,067,584 B2 | 11/2011 | Starke et al. |
| 8,101,583 B2 | 1/2012 | Glombik et al. |
| 8,106,023 B2 | 1/2012 | Glombik et al. |
| 9,295,677 B2 | 3/2016 | Ling et al. |
| 9,339,480 B2 | 5/2016 | Young et al. |
| 9,684,018 B2 | 6/2017 | Horanzy |
| 9,688,720 B2 | 6/2017 | Gillberg et al. |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 10,000,528 B2 | 6/2018 | Gillberg et al. |
| 10,011,633 B2 | 7/2018 | Gillberg et al. |
| 10,093,697 B2 | 10/2018 | Gillberg et al. |
| 10,428,109 B1 | 10/2019 | Bhat et al. |
| 10,487,111 B2 | 11/2019 | Gillberg et al. |
| 10,709,755 B2 | 7/2020 | Ando et al. |
| 10,941,127 B2 | 3/2021 | Gilberg et al. |
| 10,975,046 B2* | 4/2021 | Lundqvist ................ A61P 1/16 |
| 10,995,115 B2 | 5/2021 | Bhat et al. |
| 11,014,898 B1 | 5/2021 | Gillberg et al. |
| 11,111,224 B2 | 9/2021 | Gillberg |
| 11,225,466 B2 | 1/2022 | Gillberg et al. |
| 11,267,794 B2 | 3/2022 | Gillberg et al. |
| 11,572,350 B1 | 2/2023 | Gillberg et al. |
| 2002/0142054 A1 | 10/2002 | Marlett et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0199515 A1 | 10/2003 | Mudipalli et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2005/0282822 A1 | 12/2005 | Alstermark et al. |
| 2005/0287178 A1 | 12/2005 | Steed |
| 2006/0083790 A1 | 4/2006 | Anderberg et al. |
| 2007/0197522 A1 | 8/2007 | Edwards et al. |
| 2008/0207592 A1 | 8/2008 | Frick et al. |
| 2008/0300171 A1 | 12/2008 | Balkan et al. |
| 2009/0131395 A1 | 5/2009 | Antonelli et al. |
| 2010/0286122 A1 | 11/2010 | Belyk |
| 2011/0003782 A1 | 1/2011 | Pellicciari |
| 2011/0152204 A1 | 6/2011 | Gedulin et al. |
| 2011/0294767 A1 | 12/2011 | Gedulin et al. |
| 2012/0114588 A1 | 5/2012 | Starke et al. |
| 2013/0029938 A1 | 1/2013 | Aquino et al. |
| 2013/0108573 A1 | 5/2013 | Gedulin et al. |
| 2013/0109671 A1 | 5/2013 | Gedulin et al. |
| 2013/0225511 A1* | 8/2013 | Gillberg ................ A61K 31/575 514/21.91 |
| 2013/0236541 A1* | 9/2013 | Gillberg .................... A61P 3/06 424/463 |
| 2014/0275090 A1 | 9/2014 | Gedulin et al. |
| 2015/0031636 A1 | 1/2015 | Gillberg et al. |
| 2015/0031637 A1 | 1/2015 | Gillberg et al. |
| 2016/0146715 A1 | 5/2016 | Shim et al. |
| 2016/0194353 A1 | 7/2016 | Gillberg et al. |
| 2017/0143738 A1 | 5/2017 | Ando et al. |
| 2017/0182115 A1 | 6/2017 | Gillberg et al. |
| 2017/0240516 A1 | 8/2017 | Ymen et al. |
| 2018/0140219 A1 | 5/2018 | Yin et al. |
| 2019/0177286 A1 | 6/2019 | Ymen et al. |
| 2019/0276493 A1 | 9/2019 | Bhat et al. |
| 2019/0367467 A1 | 12/2019 | Gillberg et al. |
| 2020/0002299 A1 | 1/2020 | Lundqvist |
| 2020/0247768 A1 | 8/2020 | Gillberg et al. |
| 2020/0247769 A1 | 8/2020 | Gillberg et al. |
| 2021/0017141 A1 | 1/2021 | Gillberg et al. |
| 2021/0024475 A1 | 1/2021 | Lundqvist |
| 2021/0147372 A1 | 5/2021 | Gillberg |
| 2021/0171479 A1 | 6/2021 | Gillberg |
| 2021/0171480 A1 | 6/2021 | Gillberg |
| 2021/0171481 A1 | 6/2021 | Gillberg |
| 2021/0171482 A1 | 6/2021 | Gillberg |
| 2021/0171483 A1 | 6/2021 | Gillberg |
| 2021/0179572 A1 | 6/2021 | Gillberg |
| 2021/0236511 A1 | 8/2021 | Byrod |
| 2022/0041567 A1 | 2/2022 | Gillberg et al. |
| 2022/0143043 A1 | 5/2022 | Gillberg |
| 2022/0402885 A1 | 12/2022 | Gillberg et al. |
| 2023/0049950 A1 | 2/2023 | Gillberg et al. |
| 2023/0109432 A1 | 4/2023 | Gillberg et al. |

FOREIGN PATENT DOCUMENTS

| | | |
|---|---|---|
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0864582 | 9/1998 |
| EP | 1173205 | 4/2000 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | A-2004-516285 | 6/2004 |
| JP | B-3665055 | 6/2005 |
| JP | 2013-541584 | 11/2013 |
| JP | A-2013-542953 | 11/2013 |
| JP | H02258719 | 10/2019 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |

(56) References Cited

FOREIGN PATENT DOCUMENTS

| | | |
|---|---|---|
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |
| WO | WO 2004/020421 | 10/2004 |
| WO | WO 2004/089350 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2011/137135 | 11/2011 |
| WO | WO 2011/150286 | 12/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2013/168671 | 11/2013 |
| WO | WO 2014/174066 | 10/2014 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |
| WO | WO 2019/172834 | 9/2019 |
| WO | WO 2020/161216 | 8/2020 |
| WO | WO 2020/161217 | 8/2020 |
| WO | WO 2020/167958 | 8/2020 |
| WO | WO 2020/167964 | 8/2020 |
| WO | WO 2020/167981 | 8/2020 |

OTHER PUBLICATIONS

PCT International Search Report and Written Opinion in International Appln No. PCT/EP2020/084569, dated Mar. 9, 2021, 13 pages.
PCT International Search Report and Written Opinion in International Appln. No. PCT/EP2020/084567, dated Feb. 11, 2021, 13 pages.
PCT International Search Report and Written Opinion in International Appln. No. PCT/EP2020/084568, dated Feb. 11, 2021, 13 pages.
PCT International Search Report and Written Opinion in International Appln. No. PCT/EP2020/084570, dated Feb. 11, 2021, 13 pages.
PCT International Search Report and Written Opinion in International Appln. No. PCT/EP2020/084571, dated Feb. 4, 2021, 14 pages.
A Long-Term, Open-Label Study of LUM001 With a Double-Blind, Placebo Controlled, Randomized Drug Withdrawal Period to Evaluate Safety and Efficacy in Children With Alagille Syndrome (ICONIC), Clinical Trials.gov, Jun. 9, 2014, retrieved Oct. 3, 2014, http://clinicaltrials.gov/ct2/show/NCT02160782?term=LUM001&rank=7, 4 pages.
AASLD: 2017 68th Annual Meeting of the American Association for the Study of Liver Diseases, Washington, DC, Oct. 20-24, 2017, (Abstract only).
Adams et al., "Hepascore: an accurate validated predictor of liver fibrosis in chronic hepatitis C infection," Clin. Chem. 2005, vol. 51(10), p. 1867-1873.
Alagile Syndrome,Wikipedia, the free encyclopedia, posted on or about Feb. 11, 2005, retrieved Feb. 12, 2014, http://en.wikipedia.org/wiki/Alagille_syndrome, 3 pages.
Alashkar et al., "Meeting Info.: 57th Annual Meeting of the AmericanSociety-of-Hematology," Orlando, FL, USA. Dec. 5-8, 2015, Amer Soc Hematol, Blood, 2015, 126(23).
Albireo's Lead Compound in Cholestatic Liver Diseases, A4250, Projects Against Bile Acid-Mediated Cholestatic Liver Injury in Mice, Albireo Press Release, Apr. 11, 2014, 2 pages.
Alissa et al., "Invited Review: Update on Progressive Familial Intrahepatic Cholestasis," Journal of Pediatric Gastroenterology and Nutrition, 2008, 46:241-252.
Alonso et al., "Histologic pathology of the liver in progressive familial intrahepatic cholestasis," Journal of Pediatric Gastroenterology and Nutrition, 14: 128-133, 1994.
Alvarez et al., "Reduced hepatic expression of farnesoid X receptor in hereditary cholestasis associated to mutation in ATP8B1," Hum Mol Genet, 2004, 13(20):2451-2460.
Alvarez, "Development of crystallization processes for pharmaceutical applications," LACCEI, 2007, 2E.3-1-2E.3-9.
Alvarez, Fernando; "Treatments in chronic cholestasis in children." Ann. Nestlé (2008) 66 p. 127-135.
American Diabetes Association, "Management of Dyslipidemia in Adults with Diabetes," Diabetes Care, Jan. 2003, 26(1).
An Extension Study to Evaluate the Long-Term Safety and Durability of Effect of LUM001 in the Treatment of Cholestatic Liver Disease in Subjects With Alagille Syndrome (IMAGINE), Clinical Trials.gov, Jan. 23, 2014, retrieved on Oct. 3, 2014, http://clinicaltrials.gov/ct2/show/NCT02047318?term=LUM001&rank=3, 3 pages.
An Extension Study to Evaluate the Long-Term Safety and Durability of Effect of LUM001 in the Treatment of Cholestatic Liver Disease in Subjects With Alagille Syndrome (IMAGINE-II), Clincal Trials.gov, Apr. 16, 2014, retrieved on Oct. 3, 2014, http://clinicaltrials.gov/ct2/show/NCT02117713?term=LUM001&rank=2, 3 pages.
Anakk et al., "Bile acids activate YAP to promote liver carcinogenesis," Cell Rep., Nov. 27, 2013, 5(4):1060-1069.
Angulo et al., "Independent Predictors of Liver Fibrosis in Patients With Nonalcoholic Steatohepatitis," Hepatology, Dec. 1999, 30(6): 1356-1362.
Angulo et al., "The NAFLD fibrosis score: a noninvasive system that identifies liver fibrosis in patients with NAFLD," Hepatology, 2007, vol. 45(4), p. 846-54.
Angulo, "Use of ursodeoxycholic acid inpatients with liver disease," Current Gastroenterology Reports, Feb. 1, 2002, 4(1):37-44.
Anzivino et al., "ABCB4 and ABCB11 mutations in intrahepatic cholestasis of pregnancy in an Italian population," Dig Liver Dis., 2013, 45(3):226-232.
Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.
Arnell et al., "Follow-up in children with progressive familial intrahepatic cholestasis after partial external biliary diversion," J Pediatr Gastroenterol Nutr., 2010, 51(4):494-499.

(56) References Cited

OTHER PUBLICATIONS

Artursson and Karlsson, "Corresalation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibito A4250 protects against bile acid-mediated cholestatic liver injury in mice," J. Hepatology, 2014, 60:S57.
Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Balbach et al., "Pharmaceutical evaluation of early development candidates "the 100 mg-approach"," Int J Pharm, May 4, 2004, 275(1):1-12.
Banker et al., "Modern Pharmaceutics, 3ed", Marcel Dekker, New York, 1996, pp. 451 and 596.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Bavin, "Polymorphism in Process Development," Chemistry and Industry, 527-529, 1989.
Beausejour et al., "Description of two new ABCB11 mutations responsible for type 2 benign recurrent intrahepatic cholestasis in a French-Canadian family," Can J Gastroenterol., 2011, 25(6):311-314.
Beraza et al., Nor-ursodeoxycholic acid reverses hepatocyte-specific nemo-dependnt steatohepatitis. Gut, 2011: 60: 387-396.
Billington et al., "Effects of bile salts on the plasma membranes of isolated rat hepatocytes," Bichem. J. 188: 321-327, 1980.
Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Board of Appeal of European Patent Office, Case No. T 077/08-3.3.01, dated May 24, 2011, 17 pages.
Boncristani et al., Respiratory Viruses, Encyclopedia of Microbiology, 2009, 19 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Bounford. University of Birmingham. Dissertation Abstracts International, (2016) vol. 75, No. IC. Order No. AAI10588329. ProQuest Dissertations & Theses.
Bowel Diversion Surgeries: Ileostomy, Colostomy, Ileoanal Reservoir and Continent Ileostomy, US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
Brunt et al., "Nonalcoholic Steatohepatitis: a Proposal for Grading and Staging the Histological Lesions," American Journal of Gastroenterology, Sep. 1999, 94(9): 2467-2474.
Brunzell and Hokanson, "Dislipidemia of Central Obesity and Insulin Resistance," Diabetes Care, 1999, 22(Suppl. 3):C10-C13.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Burrows, "Interventions for treating cholestasis in pregnancy," Cochrane Database Syst. Rev., 4:CD00493, 2001.

Byrn et al., "Pharmaceutical Solids: a Strategic Approach to Regulatory Considerations," Pharmaceutical Research, 1995, 12(7), pp. 945-954.
Byrne et al., "Missense mutations and single nucleotide polymorphisms in ABCB11 impair bile salt export pump processing and function or disrupt pre-messenger RNA splicing," Hepatology., 2009, 49(2):553-567.
Caira, "Crystalline Polymorphism of Organic Compounds," in: Topics in Current Chemistry, Jan. 1998, 198:163-208.
Camilleri, "Probiotics and irritable bowel syndrome: rationale, putative mechanisms, and evidence of clinical efficacy," Clin. Gastroenterol,, 40(3):264-9, Mar. 2006.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.
Chang et al., "Bile acids promote the expression of hepatitis c virus in replicon-harboring cells," Journal of Virology, Sep. 2007, 81(18):9633-9640.
Chauhan et al., "Pharmaceutical polymers," Encycl. Biomed. Polymers and Polymeric Biomaterials, 2016, 5929-5942.
Chen et al., "Bile salt export pump is dysregulated with altered farnesoid X receptor isoform expression in patients with hepatocelular carcinoma," Hepatologu, 57: 4, 1530-1541, 2013.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chen et al., "Serum and urine metabolite profiling reveals potential biomarkers of human hepatocellular carcinoma," Molecular and Cellular Proteomics 10.7, 2011.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chey et al., "A Randomized Placebo-Controlled Phase II b Trial of A3309, a Bile Acid Transporter Inhibitor, for Chronic Idiopathic Constipation," Am. J. Gastroenterology, May 2011, 106:1803-1812.
Chiang, "Bile acids: regulation of synthesis," J. Lipid Res, 2009, 50(10):1955-1966.
Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platfoim," PLoS One, 2017, 12(6):e0179200.
Das & Kar., Non alcoholic steatohepatitis. JAPI. 53:, Mar. 2005.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," Hepatology: Autoimmune, Cholestatic and Biliary Disease, May 2010, 1645-1655.
Davit-Spraul et al., "Liver transcript analysis reveals aberrant splicing due to silent and intronic variations in the ABCB11 gene," Mol Genet Metab., 2014, 113(3):225-229.
Davit-Spraul et al., "Progressive familial intrahepatic cholestasis," Orphanet Journal of Rare Diseases, Jan. 2009, 4:1-12.
Dawson et al., "Bile acid transporters" J. Lipid Res. 2009, 50, 2340-2357.
Dawson, "Role of the intestinal bile acid transporters in bile acid and drug disposition," Handb. Exp. Pharmacol. 2011, 201:169-203.

(56) References Cited

OTHER PUBLICATIONS

De Lédinghen et al., "Controlled attenuation parameter for the diagnosis of steatosis in non-alcoholic fatty liver disease," J Gastroenterol Hepatol., 2016, 31(4):848-855.
DeFronzo et al., "Insuline resistance, a multisurfaced syndrome responsible for NIDDM, obesity, hypertension, dyslipidemia and atherosclerotic cardiovascular disease," Diabetes Care, 1991, 14:173-194.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-Invasive Quantitative Assessment of Liver Fat by Ultrasound Imaging," Ultrasound Med Biol., 2018, 44(8):1585-1596.
Di Padova et al., "Double-blind placebo-controlled clinical trial of microporous chlestyramine in the treatment of intra- and extrahepatic cholestasis: relationship between itching and serum bile acids," Methods Find Exp Clin Pharmacol., Dec. 1984, 6(12):773-776 (Abstract Only).
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drags as inhibitors of the human sodium taurocholate cotransporting polypeptide (NTCP).," Mol. Pharm. 2013, 10(3):1008-1019.
Dongiovanni et al., "Genetic Predisposition in NAFLD and NASH: Impact on Severity of Liver Disease and Response to Treatment," Curren Pharma Design, 2013, 19:5219-5238.
Drage et al., "Exon-skipping and mRNA decay in human liver tissue: molecular consequences of pathogenic bile salt export pump mutations," Sci Rep., 2016, vol. 6: 24827.
Drage et al., "Sequencing of FIC1, BSEP and MDR3 in a large cohort of patients with cholestasis revealed a high number of different genetic variants," J Hepatol. 2017, 67(6):1253-1264.
Droge et al., Zeitschrift fur Gastroenterologie 2015, 53(12) Abstract No. A3-27. Meeting Info: 32. Jahrestagung der Deutschen Arbeitsgemeinschaft zum Stadium der Leber. Dusseldorf, Germany. Jan. 22, 2016-Jan. 23, 2016.
Drumond et al., "Patients' appropriateness, acceptability, usability and preferences for pharmaceutical preparations: Results from a literature review on clinical evidence," Int. J. Pharm. 2017, 521(1-2):294-305.
EASL Clinical Practice Guidelines: Management of cholestatic liver diseases, European Assoc. for the Study of the Liver, Journal of Hepatology, 2009, 51:237-267.
Einspahr et al., "Protective role of wheat bran fiber: data from marker trials," Am. J. Med., 106(1A):32s-37s, Jan. 1999.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Ellinger et al., "Partial external biliary diversion in bile salt export pump deficiency: Association between outcome and mutation," World J Gastroenterol., 2017, 23(29):5295-5303.
Ellis et al., "Zebrafish abcb11b mutant reveals strategies to restore bile excretion impaired by bile salt export pump deficiency," Hepatology, 2018, 67(4)1531-1545.
Engelen et al., "Oral size perception of particles: effect of size, type, viscosity and method," J. Text. Studies 2005, 36(4):373-386.
Espenshade and Hughes, "Regulation of Sterol Synthesis in Eukaryotes," Annu. Rev. Genet., 2007, 41:401-427.
Evaluation of LUM001 in the Reduction of Pruritus in Alagille Syndrome (ITCH), Clinical Trials.gov, Feb. 5, 2014, retrieved on Oct. 3, 2014, http://clinicaltrials.gov/ct2/show/NCT02057692?term=LUM001&rank=5, 4 pages.
Evason et al., "Morphologic findings in progressive familial intrahepatic cholestasis 2 (PFIC2): correlation with genetic and immunohistochemical studies," Am J Surg Pathol., 2011, 35(5):687-696.

Extended European Search Report in European Application No. 11840392.2, dated Feb. 24, 2014, 7 pages.
Extended European Search Report in European Application No. 11840481.3, dated Feb. 13, 2014, 10 pages.
Faubion et al., "Toxic bile salts induce rodent hepatocyte apoptosis via direct activation of Fas," The Journal of Clinical Investigation, 103: 1, 137-145, 1999.
Ferreira et al., Pediatric Transplantation 2013, 17(SUPPL. 1):99. Abstract No. 239. Meeting Info: IPTA 7th Congress on Pediatric Transplantation, Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Forner et al., "Treatment of hepatocellular carcinoma," Critical Reviews in Oncology/Hematology, 2006, 60:89-98.
Francalanci et al., "Progressive familial intrahepatic cholestasis: Detection of new mutations and unusal modality of transmission," Digestive and Liver Disease 2010, 42(SUPPL. 1):516, Abstract No. T.N.5.
Francalanci et al., Laboratory Investigation 2011, vol. 91, Supp. SUPPL. 1, pp. 360A. Abstract No. 1526.
Gao et al., "Detection of hepatitis in children with idiopathic cholestatic bile salt export pump gene mutations," Shandong Yiyao, 2012, 52(10):14-16.
Gao et al., "Recent developments in the crystallization process: toward the pharmaceutical industry," Engineering, 2017, 3:343-353.
Gao et al., "The Identification of Two New ABCB11 Gene Mutations and the Treatment Outcome in a Young Adult with Benign Recurrent Intrahepatic Cholestasis: a Case Report," Hepatitis Monthly 2017, 17(10):e55087/1-e55087/6.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "The IBAT Inhibition by A3309—a Potential Mechanism for the Treatment of Constipation," Gastroenterology, 2010, 138(5), Supp 1, S-224.
Giovannoni et al., "Genetics and Molecular Modeling of New Mutations of Familial Intrahepatic Cholestasis in a Single Italian Center," PLoS One, 2015, 10(12):e0145021.
Glagov et al., "Compensatory enlargement of human athersclerotic coronary arteries," N Engl. J. Med., May 1987, 316(22):1371-1375 (Abstract Only).
Goldschmidt et al., "Increased frequency of double and triple heterozygous gene variants in children with intrahepatic cholestasis," Hepatol Res., 2016, 46(4):306-311.
Govers et al., "Characterization of the adsorption of conjugated and unconjugated bile acids to insoluble, amorphous calcium phosphate", Journal of Lipid Research 35(5):741-748, 1994.
Greten, "Molecular therapy for the treatment of hepatocellular carcinoma," Br. J. Cancer, 2009, 100:19-23.
Griffin, et al., "A novel gene mutation in ABCB11 in siblings with progessive familial intrahepatic cholestasis type 2," Canadian Journal of Gastroenterology and Hepatology 2016, vol. 2016. Abstract No. A200. Meeting Info: 2016 Canadian Digestive Diseases Week, CDDW 2016. Montreal, QC, United States. Feb. 26, 2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchuang Erke Zazhi, 2013, 31(10):905-909.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.

(56) References Cited

OTHER PUBLICATIONS

Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.

Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.

Hasegawa et al., "Intractable itch relieved by 4-phenylbutyrate therapy in patients with progressive familial intrahepatic cholestasis type 1," Orphanet J Rare Dis., 2014, 9:89.

Hayashi et al., "Assessment of ATP8B1 Deficiency in Pediatric Patients With Cholestasis Using Peripheral Blood Monocyte-Derived Macrophages," EBioMedicine, 2018, 27:187-199.

Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.

Heathcote, "Management of primary biliary cirrhosis," Hepatology, 2000, 31(4):1005-1013.

hepc.liverfoundation.org' [online]. "Nonalcoholic Fatty Liver Disease," Brochure, 2016 [retrieved on Feb. 1, 2018], Retrived from the Internet: URL<http://hepc.liverfoundation.org/wp-content/uploads/2012/07/NAFLD-Brochure-2016.pdf>, 8 pages.

Herbst et al., "Taking the next step forward—Diagnosing inherited infantile cholestatic disorders with next generation sequencing," Mol Cell Probes, 2015, 29(5):291-298.

Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.

Ho et al., "Polymorphic variants in the human bile salt export pump (BSEP; ABCB11): functional characterization and interindividual variability," Pharmacogenet Genomics, 2010, 20(1):45-57.

Hollands et al., "Ileal exclusion for Byler's disease: an alternative surgical approach with promising early results for pruritus," Journal of Pediatric Surgery, Feb. 1988, 33(2): 220-224.

Holz et al., "Can genetic testing guide the therapy of cholestatic pruritus? A case of benign recurrent intrahepatic cholestasis type 2 with severe nasobiliary drainage-refractory itch," Hepatol Conunun., 2018, 2(2):152-154.

Holz et al., "Plasma separation and anion adsorption results in rapid improvement of nasobiliary drainage (NBD) -refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie- 10. Herbsttagung derDeutschen Gesellschaft fur Allgemein- und Viszeralchirurgie. Hamburg, Germany. Sep. 21, 2016-Sep. 24, 2016.

Hsu et al., "Adult progressive intrahepatic cholestasis associated with genetic variations in ATP8B1 and ABCB11," Hepatol Res., 2009, 39(6):625-631.

Hu et al., "Diagnosis of ABCB11 gene mutations in children with intrahepatic cholestasis using high resolution melting analysis and direct sequencing," Mol Med Rep., 2014, 10(3):1264-1274.

Huang et al., "Discovery of Potent, Nonsystemic Apical Sodium-Codependent Bile Acid Transporter Inhibitors (Part 2)," J. Med. Chem., 2005, 48:5853-5868.

IBAT inhibitor A4250 for Cholestatic Pruritus, ClinicalTrials.gov, Last updated Feb. 10, 2015, https://clinicaltrials.gov/ct2/show/NCT02360852?term=a4250&rank=1, 3 pages.

Imagawa et al., "Clinical phenotype and molecular analysis of a homozygous ABCB11 mutation responsible for progressive infantile cholestasis," J Hum Genet. 2018, 63(5):569-577.

Imagawa et al., "Generation of a bile salt export pump deficiency model using patient-specific induced pluripotent stem cell-derived hepatocyte-like cells," Sci Rep., 2017, 7:41806.

Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016.

Initiation of a Phase II Trial for A4250, the Company's Lead Compound for Cholestatic Liver Diseases and NASH, Albireo Pharma Press Release, Feb. 5, 2015, http://www.alberiopharma.com/News.aspx?PageID=1600872, 2 pages.

International Preliminary Report on Patentability for Application No. PCT/JP2015/068240, dated Jan. 5, 2017, 12 pages (with English translation).

International Preliminary Report on Patentability for International Application No. PCT/EP2015/074573, dated Apr. 25, 2017, 8 pages.

International Preliminary Report on Patentability for International Application No. PCT/SE2011/051335, dated May 23, 2011, 7 pages.

International Preliminary Report on Patentability for International Application No. PCT/SE2011/051336, dated May 23, 2013, 11 pages.

International Search Report and Written Opinion for Application No. PCT/EP2014/058432, dated Jul. 11, 2014, 9 pages.

International Search Report and Written Opinion for Appln. No. PCT/EP2019/064602, dated Aug. 9, 2019, 11 pages.

International Search Report and Written Opinion for International Application No. PCT/EP2015/074573, dated Apr. 28, 2016, 11 pages.

International Search Report and Written Opinion for International Application No. PCT/SE2011/051335, dated Feb. 3, 2012, 12pages.

International Search Report and Written Opinion for International Application No. PCT/SE2011/051366, dated Feb. 22, 2012, 18 pages.

International Search Report and Written Opinion in Appln. No. PCT/SE2019/050603, dated Sep. 18, 2019, 11 pages.

International Search Report and Written Opinion in International Application No. PCT/SE2018/050802, dated Oct. 26, 2018.

International Search Report and Written Opinion in International Application No. PCT/SE2018/050803, dated Oct. 26, 2018.

International Search Report and Written Opinion in International Appln. No. PCT/EP2020/052940, dated Mar. 23, 2020, 12 pages.

International Search Report and Written Opinion in International Appln. No. PCT/EP2020/052942, dated Mar. 23, 2020, 9 pages.

International Search Report, Application No. PCT/JP2015/068240, dated Sep. 15, 2015, 11 pages (with English translation).

Ishak et al., "Histological grading and staging of chronic hepatitis," J. Hepatol. 1995, vol. 22, p. 696-699.

Ishibashi et al., "Hypercholesterolemia in low density lipoprotein receptor knockout mice and its reversal by adenovirus-mediated gene delivery", Journal of Clinical Investigation 92(2):883-893, 1993.

Ivashkin et al., "A novel mutation of ATP8B1 gene in young patient with familial intrahepatic cholestasis.," Hepatology International 2016, 10(1):S461, Abstract No. LBO-38. Meeting Info: 25th Annual Conference of the Asian Pacific Association for the Study of the Liver, APASL 2016. Tokyo, Japan, Feb. 20, 2016-Feb. 24, 2016.

Jacquet et al., "Alagille Syndrome in Adult Patients: It is Never Too Late," American Journal of Kidney Diseases, May 2007, 49(5):705-709.

Jankowska et al., "[Cholestatic liver disease in children]," Przegl. Epidemiol., 56:16-21, 2002.

Jankowska et al., "Ileal exclusion in children with progressive familial intrahepatic cholestasis," J Pediatr Gastroenterol Nutr. 2014,58(1):92-95.

Jansen et al., "Endogenous bile acids as carcinogens," Journal of Hepatology, Sep. 2007, 47(3):434-435.

Jaquotot-Haerranz et al., "Clinical variability of mutations in the ABCB11 gene: a case report," Rev Esp Enferm Dig., 2013, 105(1):52-54.

(56) References Cited

OTHER PUBLICATIONS

Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.

Jiang et al., "Non alcoholic steatohepatitis a precursor for hepatocellular carcinoma development," World Journal of Gastroenterology: WJG, Nov. 28, 2014, 20(44):16464-16473.

Jirsa et al., "Indel in the FIC1/ATP8B1 gene-a novel rare type of mutation associated with benign recurrent intrahepatic cholestasis," Hepatol Res. 2004, 30(1):1-3.

Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.

Kang et al., "Progressive Familial Intrahepatic Cholestasis in Korea: a Clinicopathological Study of Five Patients," J Pathol Transl Med. May 16, 2019, 53(4):253-260.

Karpen and Dawson, "Not all (bile acids) who wander are lost: the first report of a patient with an isolated NTCP defect," Hepatology, 2015, 61(1):24-27.

Khosla et al., "Recurrent Post-partum Jaundice: Rare Genetic Disorder With Novel Genetic Mutations Identified," American Journal of Gastroenterology 2015, 110(1):5397. Meeting Info.: 80th Annual Scientific Meeting of the American-College-of-Gastroenterology. Honolulu, HI, USA. Oct. 16-21, 2015.

Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Knisely et al., "Hepatocellular Carcinoma in ten children under five years of age with bile salt export pump deficiency," Hepatology, Aug. 2006, 44(2):478-486.

Kooistra, et al., "KLIFS: a structural kinase-ligand interaction database," Nucleic Acids Res., 2016, vol. 44, No. DI, pp. D365-D371.

Korman et al., "Assessment of Activity in Chronic Active Liver Disease," New England Journal of Medicine, 2010, 290(25):1399-1402.

Kosters et al., "Bile acid transporters in health and disease," Xenobiotica 2008, 38(7-8):1043-1071.

Kozarewicz, "Regulatory perspectives on acceptability testing of dosage forms in children," Int. J. Pharm. 2014, 469(2):245-248.

Krawczyk et al., "Prolonged cholestasis triggered by hepatitis A virus infection and variants of the hepatocanalicular phospholipid and bile salt transporters," Ann Hepatol., 2012, 11(5):710-744.

Kumar and Tandon, "Use of ursodeoxycholic acid in liver diseases," J. Gastroenterology and Hepatology, 2001, 16:3-14.

Kumar et al., "Cholestatic presentation of chronic hepatitis c." Dig. Dis.Sci, 2001, 46(10):2066-2073.

Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.

Kurbegov et al., Biliary diversion for progressive familial intrahepatic cholestasis: Improved liver morphology and bile acid profile, Gastroenterology, 125: 4, 1227-1234, 2003.

Lam et al., "A patient with novel ABCB11 gene mutations with phenotypic transition between BRIC2 and PFIC2," J Hepatol. 2006, 44(1):240-242.

Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.

Lang et al,. "Genetic variability, haplotype structures, and ethnic diversity of hepatic transporters MDR3 (ABCB4) and bile salt export pump (ABCB11)," Drug Metab Dispos. 2006, 34(9):1582-1599.

Lang et al., "Mutations and polymorphisms in the bile salt export pump and the multidrug resistance protein 3 associated with drug-induced liver injury," Pharmacogenet Genomics, 2007, 17(1):47-60.

Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.

Lee et al., "Early Diagnosis of ABCB11 Spectrum Liver Disorders by Next Generation Sequencing," Pediatr Gastroenterol Hepatol Nutr. 2017, 20(2):114-123.

Lewis et al., "Effects of 2164U90 on ileal bile acid adsorption and serum cholesterol in rats and mice", Journal of Lipid Research 36(5):1098-1105, 1995.

Li et al., "ATP8B1 and ABCB11 mutations in Chinese patients with normal gamma-glutamyl transferase cholestasis: Phenotypic differences between progressive familial intrahepatic cholestasis type 1 and 2," Hepatology International 2017, 11(1):5180. Abstract No. OP284.

Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China. Feb. 15, 2017-Feb. 19, 2017.

Li et al., "Effect of Resistant Starch Film Properties on the Colon-Targeting Release of Drug From Coated Pellets", 152 J Control. Rel. e5, 2011.

Lichtinghagen R, et al., "The Enhanced Liver Fibrosis (ELF) score: normal values, influence factors and proposed cut-off values," J Hepatol. Aug. 2013;59(2):236-42.

Lin et al., "[Clinical and genetic analysis of an infant with progressive familial intrahepatic cholestasis type II].," Zhongguo Dang Dai Er Ke Za Zhi. 2018, 20(9)758-764 (with English abstract).

Ling, "Congenital cholestatic syndromes: What happens when children grow up?," Can J Gastroenterol, Nov. 11, 2007, 21(11):743-751.

Liu et al., "ABCB11 gene mutations in Chinese children with progressive intrahepatic cholestasis and low gamma glutamyltransferase," Liver International 2010, 30(6):809-815.

Liu et al., "Association of variants of ABCB11 with transient neonatal cholestasis," Pediatr Int. 2013, 55(2):138-144.

Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.

Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver, Hong Kong, China. Feb. 13, 2009-Feb. 16, 2009.

Liu et al., "Homozygous p.Ser267Phe in SLC10A1 is associated with a new type of hypercholanemia and implications for personalized medicine," Scientific Reports, 2017, 7:9214.

Liu, et al., "Patient-centered pharmaceutical design to improve acceptability of medicines: similarities and differences in paediatric and geriatric populations," Drugs 2014, 74(16):1871-1889.

Loh et al., "Overview of milling techniques for improving the solubility of poorly water-soluble drugs," Asian J Pharm Sci., 2015, 10:225-274.

Longo et al., "Hyperlipidemia in chronic cholestatic liver disease," Curr. Treat. Options Gastrenterol. ,2001, 4:111-114.

Lopez et al., "Effect of formulation variables on oral grittiness and preferences of multiparticulate formulations in adult volunteers," Eur. J. Pharm. Sci. 2016, 92:156-162.

(56) References Cited

OTHER PUBLICATIONS

Lopez et al., "Formulation approaches to pediatric oral drag delivery: benefits and limitations of current platforms," Expert Opin. Drug Deliv., 2015, 12(11):1727-1740.

Lumena Pharmaceuticals Now Dosing Patients in the INDIGO Phase 2 Clinical Trial of LUM001 in Pediatric Patients with Progressive Familial Intrahepatic Cholestasis, PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.

Lv et al., "Noninvasive Quantitative Detection Methods of Liver Fat Content in Nonalcoholic Fatty Liver Disease," J Clin Transl Hepatol. 2018, 6(2):217-221.

Lykavieris et al., "Outcome of liver disease in children with Alagille syndrome: a study of 163 patients," Gut, 2001, 49:431-435.

Maggiore et al., "Relapsing features of bile salt export pump deficiency after liver transplantation in two patients with progressive familial intrahepatic cholestasis type 2," J Hepatol. 2010, 53(5):981-6.

Manghat and Wierzbicki, "Colesevelam hydrochloride: a specifically engineered bile acid sequestrant," Future Lipidology, 3(3):237-255, Jun. 2008.

Marzorati et al., "A novel hypromellose capsule, with acid resistance properties, permits the targeted delivery of acid-sensitive products to the intestine," LWT-Food Sci. Techno.Jan. 2015, vol. 60, p. 544-551.

Masahata et al., "Recurrence of Progressive Familial Intrahepatic Cholestasis Type 2 Phenotype After Living-donor Liver Transplantation: a Case Report," Transplant Proc. 2016, 48(9):3156-3162.

Matte et al., "Analysis of gene mutations in children with cholestasis of undefined etiology," J Pediatr Gastroenterol Nutr. 2010, 51(4):488-493.

McCullough et al., "The epidemiology and risk factors of NASH.", Blackwell Publishing, Chapter 3, 2005.

McKay et al., "Mutation detection in cholestatic patients using microarray resequncing of ATP8B1 and ABCB11 [version 2; peer review: 2 approved, 1 approved with reservations]," F1000 Res., 2013, 2:32.

McMichael and Potter, "Reproduction, endogenous and exogenous sex hormones, and colon cancer: a review and hypothesis," J. Natl. Cancer Inst., 65(6):1201-07, Dec. 1980.

McPherson et al., "Simple non-invasive fibrosis scoring systems can reliably exclude advanced fibrosis in patients with non-alcoholic fatty liver disease," Gut 2010, 59(9):1265-9.

MerckManuals.com', "Obesity," 2008, Merch Manual for Health Care Professionals, Section-Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.

Michielsen et al., "Viral hepatitis and hepatocellular carcinoma," World Journal of Surg. Oncol, May 2005, 3(27):1-18.

Miloh et al., Gastroenterology 2006, vol. 130, No. 4, Suppl. 2, pp. A759-A760. Meeting Info.: Digestive Disease Week Meeting/107th Annual Meeting of the American-GastroenterologicalAssociation. Los Angeles, CA, USA. May 19.

Mishra et al., "Investigation of organoleptic characteristics in the development of soft chews of calcium carbonate as mineral supplement," Yakugaku Zasshi 2009, 129(12):1537-1544.

Mistry et al., "Evidence of acceptability of oral paediatric medicines: a review," J. Pharm. Pharmacol. 2017, 69(4):361-376.

Mizuochi et al., "Characterization of urinary bile acids in a pediatric BRIC-1 patient: effect of rifampicin treatment," Clin Chim Acta. 2012, 413(15-16):1301-1304.

Moghadamrad et al., "Cholestasis in a patient with gallstones and a normal gamma-glutamyl transferase," Hepatology, 2013, 57(6):2539-2541.

Morissette et al., "High-throughput crystallization: polymorphs, salts, co-crystals and solvates of pharmaceutical solids," Advanced Drug Delivery Reviews, 2004, 56:275-300.

Morotti et al., "Progressive Familial Intrahepatic Cholestasis (PFIC) Type 1, 2, and 3: a Review of the Liver Pathology Findings," Seminars in Liver Disease, Feb. 2011, 31(1):3-10.

Mouzaki and Allard, "Non-alcoholic steatohepatitis: the therapeutic challenge of a global epidemic," Annals of Gastroenterology, 2012, 25: 207-217.

Mowat et al., "Respiratory chain complex III [correction of complex] in deficiency with pruritus: a novel vitamin responsive clinical feature," J. Pediatr., 134(3):352-4, Mar. 1999.

Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.

Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.

Narchi et al., "Intrahepatic cholestasis in two omani siblings associated with a novel homozygous ATP8B1 mutation, c.379C>G (p.L127V).," Saudi J Gastroenterol. 2017, 23(5):303-305.

Neuman, et al., "Biomarkers in nonalcoholic fatty liver disease," Can. J. Gastroenterol. Hepatol. 2014, 28(11):607-618.

Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.

Noe et al., "Impaired expression and function of the bile salt export pump due to three novel ABCB11 mutations in intrahepatic cholestasis," J Hepatol. 2005, 43(3):536-543.

O'Neill et al.,"Comparison of efficacy of plant stanol ester and sterol ester: short-term and longer-term studies," American Journal of Cardiology, 96(1A):29d-36D, Jul. 2005.

Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.

Open Label Study to Evaluate Efficacy and Long Term Safety of LUM001 in the Treatment of Cholestatic Liver Disease in Patients With Progressive Familial Intrahepatic Cholestasis (INDIGO), Clinical Trials.gov, Feb. 5, 2014, retrieved on Oct. 3, 2014, http://clinicaltrials.gov/ct2/show/NCT02057718?term=LUM001&rank=4, 3 pages.

Open Label Study to Evaluate Safety and Efficacy of LUM001 in Patients With Primary Sclerosing Cholangitis (CAMEO), Clinical Trials.gov, Feb. 11, 2014, retrieved Oct. 3, 2014, http://clinicaltrials.gov/ct2/show/NCT02061540?term=LUM001&rank=6, 3 pages.

Painter et al.," Sequence variation in the ATP8B1 gene and intrahepatic cholestasis of pregnancy," Eur J Hum Genet. 2005, 13(4):435-439.

Park et al., "Clinical and ABCB11 profiles in Korean infants with progressive familial intrahepatic cholestasis," World J Gastroenterol., 2016, 22(20):4901-4907.

Parker et al., "Molecular mechanisms underlying bile acid-stimulated glucagon-like peptide-1 secretion," British J. Pharmacology, 2012, 165:414-423.

Patani et al., "Bioisosterism: a Rational Approach in Drug Design," Chem Rev, 1996, 96:3147-3176.

Pauli-Magnus et al., "Enterohepatic transport of bile salts and genetics of cholestasis," Journal of Hepatology, 2005, 43(2):342-357.

Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.

(56) References Cited

OTHER PUBLICATIONS

Peng et al., "[Relationship between phenotype and genotype of ABCB11 deficiency in siblings and literature review].," Zhonghua er ke za zhi (Chinese journal of pediatrics) 2018, 56(6):440-444.

Perez et al., "Bile-acid-induced cell injury and protection," World J Gastroenterol, Apr. 2009, 15(14)1677-1689.

Perumpail et al., "Clinical epidemiology and disease burden of nonalcoholic fatty liver disease," World Journal of Gastroenterology, Dec. 2017, 23(47): 8263-8276.

Phase 2 Study to Evaluate LUM001 in Combination With Ursodeoxycholic Acid in Patients With Primary Biliary Cirrhosis (CLARITY),Clinical Trials.gov, Jul. 17, 2013, retrieved Oct. 3, 2014, http://clinicaltrials.gov/ct2/show/NCT01904058?term=LUM001&rank=8, 3 pages.

Plump et al., "Severe hypercholesterolemia and atherosclerosis in apolipoprotein E-deficient mice created by homologous recombination in ES cells", Cell (71):343-353, 1992.

Podesta et al., "Treatment of pruritus of primary biliary cirrhosis with rifampin," Dig. Dis. Sci, 1991, 36(2):216-220.

Poupon et al., "Chronic Cholestatic Disease," J. Hepatology, 2000, 32(1):12-140.

Progressive familial intrahepatic cholestasis, Wikipedia, the free encyclopedia, posted on or about Feb. 24, 2006, http://en.wikipedia.org/wiki/Progressive_familial_intrahepatic_cholestasis, 3 pages.

Qiu et al., "Defects in myosin VB are associated with a spectrum of previously undiagnosed low γ-glutamyltransferase cholestasis," Hepatology 2017, 65(5)1655-1669.

Qiu et al., "Disruption of BSEP function in HepaRG cells alters bile acid disposition and is a susceptive factor to drug-induced cholestatic injury," Mol. Pharmaceutics, 13:4,, 2016 (Abstract only).

Rancaniello, "How many viruses on earth?" Virology Blog, Sep. 2013, 6 pages.

Reeder et al., "Quantitative assessment of liver fat with magnetic resonance imaging and spectroscopy," J Magn Reson Imaging, 2011, 34(4):729-749.

Renga et al., "Role of FXR in regulating bile acid homeostasis and relevance for human diseases," Curr. Drug. Targets Immune Endocr. Metabol. Disord., 5(3):289-303, Sep. 2005.

Report EC20082069.02.01 dated Feb. 2009, filed with appellant's letter of Apr. 26, 2011.

Report filed at oral proceedings before opposition division, GMS-CFEP-2007-20, "Filtration and Drying Study on Amorphous and Form IV Atorvastatin Calcium," 2007.

Ricci, "Bridging studies in support of oral pediatric formulation development," Int. J. Pharmaceuticals, 2013, 457:323-326.

Rolo et al., "Bile acids affect liver mitochondrial bioenergetics: Possible relevance for cholestasis therapy," Toxocological Sciences, 57: 177-185, 2000.

Rumbo et al., Transplantation 2018, vol. 102, No. 7, Supp. Supplement 1, pp. 5848. Abstract No. P.752. Meeting Info: 27th International Congress of the Transplantation Society, TTS 2018. Madrid, Spain. Jun. 30, 2018-Jul. 5, 2018.

Ryder, "Guidelines for the diagnosis and treatment of hepatocellular carcinoma (HCC) in adults," Gut, May 2003, 52:(Suppl.111):iii1-iii8.

Safety and Efficacy Study of LUM001 in the Treatment of Cholestatic Liver Disease in Patients With Alagille Syndrome (IMAGO), Clinical Trials.gov, Jul. 16, 2013, http://clinicaltrials.gov/ct2/show/NCT01903460?term=LUM001&rank=1, 3 pages.

Sanyal et al. The etiology of hepatocellular carcinonna and consequences of treatment. The Oncologist, 2010, 15 Suppl 4, 14-22.

Satapathy and Sanyal, "Epidemiology and Natural History of Nonalcoholic Fatty Liver Disease," Seminars in Liver Disease, Aug. 2015, 35(3): 221-235.

Sattler et al., "Functional analysis of previously uncharacterised disease-causing mutations of the bile salt export pump," Journal of Hepatology 2017, 66(1):5177. Meeting Info.: International Liver Congress/ 52nd Annual Meeting of the European-Association-for-the-Studyof- the-Liver. Amsterdam, Netherlands. Apr. 19-23, 2017, European Assoc Study Liver.

Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-GastroenterologicalAssociation. Washington, DC, USA. May 19-24, 2007. Amer Gastroenterol Assoc; Amer Assoc Study Liver Dis; Amer Soc Gastrointestinal Endoscopy; Soc Surg Alimentary Tract.

Scheuer, "Primary Biliary Cirrhosis," Proc. R. Soc. Med., Dec. 1967, 60:1257-1260.

Schiller, "Review article: the therapy of constipation", Alimentary Pharmacology and Therapeutics 15(6):749-763, 2001.

Schumpelick et al., "[Ulcerative colitis—late functional results of ileoanal pouch absortption]," Chirung, 69(10):1013-19, Oct. 1998.

Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):5329. Abstract No. CO18. Meeting Info: 17th National Congress SIGENP. Pescara, Italy. Oct. 7, 2010-Oct. 9, 2010.

Shah et al., "Progressive Familial Intrahepatic Cholestasis Type 2 in an Indian Child," J Pediatr Genet. 2017, 6(2):126-127.

Shah et al., "Role of Caco-2 Cell Monolayers in Prediction of Intestinal Drug Absortption," Biotechnol. Prog., 2006, 22:186-198.

Shang et al., "Colesevelam improves insulin resistance in a diet-induced obesity (F-DIO) rat model by increasing the release of GLP-1," Am J. Physiol Gastrointest Liver Physiol, 2010, 298:G419-G424.

Shaprio et al., "DHPLC screening for mutations in progressive familial intrahepatic cholestasis patients," J Hum Genet. 2010, 55(5):308-313.

Sharma et al., "Spectrum of genomic variations in Indian patients with progressive familial intrahepatic cholestasis," BMC Gastroenterol, 2018, 18(1):107.

Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017, Bhubaneswar, India. Dec. 14, 2017-Dec. 17, 2017.

Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.

Shimizu et al., "Living-related liver transplantation for siblings with progressive familial intrahepatic cholestasis 2, with novel genetic findings," Am J Transplant. 2011, 11(2):394-398.

Simons, "The fate of the orally administered bile acid sequestrant, polidexide, in humans," Clin. Exp. Pharmacol. Physiol., 3(1):99-101, Jan.-Feb. 1976.

Singhal et al., "Drug polymorphism and dosage form design: a practical perspective," Adv Drug Deliv Rev, Feb. 23, 2004, 56(3):335-347.

Sirtori, "Mechanisms of lipid-lowering agents," Cardiology, 78(3):226-35, 1991.

Sohn et al., "Benign Recurrent Intrahepatic Cholestasis Type 2 in Siblings with Novel ABCB11 Mutations," Pediatr Gastroenterol Hepatol Nutr. 2019, 22(2):201-206.

Sorrentino et al., "A Clinical-Morphological Study on Cholestatic Presentation of Nonalcoholic Fatty Liver Disease," Digestive Disease and Sciences, Jun. 2005, 50(6):1130-1135.

Sprong et al., "Dietary Calcium Phosphate Promotes Listeria monosytogenes colonization and translocation in rats red diets containing corn oil but not milk fat1", J. Nutrition (US) 132(6):1269-1274, 2002.

Squires et al., "Clinical Variability After Partial External Biliary Diversion in Familial Intrahepatic Cholestasis 1 Deficiency," J Pediatr Gastroenterol Nutr. 2017, 64(3):425-430.

Staels and Kuipers, "Bile acid sequestrants and the treatment of type 2 diabetes mellitus," Drugs, 67(10):1383-92, 2007.

Stein, "Managing Dyslipidemia in the High-Risk Patient," Am J. Cardiol., 2002, 89:50-57.

(56) References Cited

OTHER PUBLICATIONS

Sterling et al.,"Steatohepatitis: Risk factors and impact on disease severity in human immunodeficiency virus/hepatitis c virus coinfection," Hepatology, Apr. 2008, 47(4) 1118-1127.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology. 2008, 134(4):1203-1214.
Sun et al., "Bile acids promote diethylnitrosamine-induced hepatocellular carcinoma via increased inflammatory signaling," American Journal of Physiology-Gastrointestinal and Liver Physiology, May 5, 2016, 311(1):G91-104.
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Office Action in SW Appln. No. 1950463-8, dated Sep. 26, 2019, 3 pages.
Swedish Office Action in SW Appln. No. 1950464-6, dated Sep. 26, 2019, 3 pages.
Swedish Office Action in Swedish Appln. No. 1850761-6, dated Dec. 17, 2018, 8 pages.
Swedish Office Action in Swedish Appln. No. 1850762-4, dated Dec. 27, 2018, 7 pages.
Swedish Search Report for Swedish Appln. No. 1850915-8, dated Feb. 15, 2019, 2 pages.
Swedish Search Report in SW Appln. No. 1950463-8, dated Sep. 26, 2019, 2 pages.
Swedish Search Report in SW Appln. No. 1950464-6, dated Sep. 26, 2019, 3 pages.
Swedish Search Report in Swedish Appln. No. 1850761-6, dated Dec. 17, 2018, 3 pages.
Swedish Search Report in Swedish Appln. No. 1850762-4, dated Dec. 27, 2018, 3 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Biliary Cirrhosis," Am. J. Gastroenterology, 2001, 96(1): 8-15.
Tian et al., "Factors affecting crystallization of hydrates," J. Pharm. Pharmacol., 2010, 62:1534-1546.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in Japanese patients with intrahepatic cholestasis associated with low gamma-glutamyl transpeptidase level," Journal of Pediatric Gastroenterology and Nutrition 2018, 67(1):5363, Abstract No. 615.
Tollefson et al., "A novel class of apical sodium co-dependent bile acid transporter inhibitors: the 1,2-Benzothiazepines", Bioorganic and Medicinal Chemistry Letters 12:3727-3730, 2003.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codepndent Bile Acid Transporter Inhibitors (Part 1)," J. Med. Chem, 2005, 48:5837-5852.
Tyle, "Effect of size, shape and hardness of particles in suspension on oral texture and palatability," Acta Psychologica 1993, 84(1):111-118.

Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology, 2004, 127(2):379-384.
Van Tilberg et al., "Na+-dependent bile acid transport in the ileum: the balance between diarrhea and constipation", Gastroenterology 98(1):25-32, 1989.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties-a review," Pol. J. Food Nutr. Sci., 58(4):401-405, 2008.
Walsh et al., "Patient acceptability, safety and access: a balancing act for selecting age-appropriate oral dosage forms for paediatric and geriatric populations," Int. J. Pharm. 2017, 536(2):547-562.
Walsh et al., "Respiratory syncytial and other virus infections in persons with chronic cardiopulmonary disease," Americal Journal of Respiratory Critical Care Med., 1999, 160:791-795.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Wang et al.,"Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; 11(4):e0153114.
Watts and Illum, "Colonic Drug Delivery," Drug Development and Industrial Pharmacy, 1997, 23(9):893-913.
Welberg et al., "Calcium and the prevention of colon cancer", Scandinavian J. Gastroenterology Suppl. 188:52-59, 1991.
What is Alagille Syndrome?,European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Whitington et al., "Partial external diversion of bile for the treatment of intractable pruritus associated with intrahepatic cholestasis," Gastroenterology, 95: 1, 130-136, 1988 (Abstract only).
Williams et al., Foye's Principles of Medicinal Chemistry, 5th Edition, 2002, 59-63.

(56) References Cited

OTHER PUBLICATIONS

Wolff, "Burger's Medicinal Chemistry, 5ed, Part I", John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.
Zhang et al., "Abcb11 deficiency induces cholestasis coupled to impaired B-Fatty acid oxidation in mice," Journal of biological chemistry, 287: 29, 24784-2479, 2012.
Zhang et al., "Effect of bile duct ligation on bile acid composition in mouse serum and liver," Liver int, 32: 1, 58-69, 2012.
[No Author Listed],"Practical Pharmaceutical Preparation Technology," People's Medical Publishing House, Jan. 1999, 286-287 (Machine Translation).
Colorcon.com[online] "Achieving tablet stability with moisture management," retrieved on May 28, 2021, retrieved from URL<https://www.colorcon.com/connect-with-colorcon/achieving-tablet-stability-with-moisture-management>, 4 pages.
Eisai Co., Ltd., "Results from two phase 3 clinical trials of chronic constipation treatment "GOOFICE 5 mg tablet"," The Lancet Gastro & Hepat., Jul. 9, 2018, 3 pages.
Massei et al., "Cholestasis as a presenting feature of acute Epstein-Barr virus infection," The Pediatric Infectious Disease J., Feb. 2001, 5 pages.
Mwesigwa et al., "An investigation into moisture barrier fil coating efficacy and its relevance to drug stability in solid dosage forms," Int. J. Pharmacies, Jan. 2016, 497:70-77.
Trauner et al., "Inflammation-induced cholestasis," J. Gastroenterology and Hepatology, Dec. 2001, 14:10:946-959.
[No Author]"EASL Clinical Practice Guidelines: management of cholestatic liver diseases," J. Hepatol., Aug. 2009, 51:2:237-67.
Al-Dury,"Ileal Bile Acid Transporter Inhibition for the Treatment of Chronic Constipation, Cholestatic Pruritus, and NASH," Fromtiers in Pharmacology, 2018, 9:931.
Baker et al. "Systematic review of progressive familial intrahepatic cholestasis," Clin Res Hepatol Gastroenterol., 2019;43:20-36.
Bull et al., "Progressive Familial Intrahepatic Cholestasis," Clin Liver Dis., Nov. 2018, 22:4:657-669.
Clinical Trials Identifier: NCT03566238, "A Double-Blind, Randomized, Placebo-Controlled, Phase 3 Study to Demonstrate Efficacy and Safety of A4250 in Children With Progressive Familial Intrahepatic Cholestasis Types 1 and 2 (PEDFIC 1)," version 24, Apr. 18, 2019, 8 pages.
Clinical Trials Identifier: NCT03659916, "Long Term Safety & Efficacy Study Evaluating the Effect of A4250 in Children With PFIC," version 11, Oct. 24, 2019, 7 pages.
Fujino et al., "Pruritus in patients with chronic liver disease and serum autotaxin levels in patients with primaiy biliary cholangitis," BMC Gastro., 2019, 19:169.

Gillberg et al., "Clinical Pharmacology of odevixibat, a potent, selective ileal bile acid transport inhibitor with minimal systemic exposure," Annual Meeting A4250: NASPGHAN, J Pediatr Gastroenterol Nutr., 69(suppl 2):S113 Abstract No. 166-167, 2019.
International Search Report and Written Opinion in Appl. No. PCT/EP2021/081462, dated Jan. 1, 2022, 18 pages.
International Search Report and Written Opinion in Appln. No. PCT/EP2021/071618, dated Oct. 4, 2021, 13 pages.
Kamath et al., "Potential of ileal bile acid transporter inhibition as a therapeutic target in Alagille syndrome and progressive familial intrahepatic cholestasis," Liver int., Aug. 2020, 40:8:1812-1822.
Kremer et al., "Serum autotaxin is increased in pruritus of cholestasis, but not of other origin, and responds to therapeutic interventions," Hepatology, Oct. 2012, 56:4:1391-400.
Sangkhathat et al., "Variants Associated with Infantile Cholestatic Syndromes Detected in Extrahepatic Biliary Atresia by Whole Exome Studies: a 20-Case Series from Thailand," J. Pediatr Genet, 2018, 7:67-73.
Slavetinsky et al., "Odevixibat and partial external biliary diversion showed equal improvement of cholestasis in a patient with progressive familial intrahepatic cholestasis," BMJ Case Rep, 2020, 13:e234185.
Thebaut et al., "An update on the physiopathology and therapeutic management of cholestatic pruritus in children," Clinics and Res in Hepatology and Gastro., 2018, 42:2:103-109.
Van Wessel et al., "Genotype correlates with the natural history of severe bile salt export pump deficiency," Multicenter Study., Jul. 2020, 73:1:84-93.
Almasio et al., "Role of S-adenosyl-L-methionine in the treatment of intrahepatic cholestasis," Drugs, 1990, 40 Suppl (3):111-123.
Asami et al., "Treatment of children with familial hypercholesterolemia with colestilan, a newly developed bile acid-binding resin," Atherosclerosis, 2002, 164:381-2.
Baringhaus, "Substrate specificity of the ileal and the hepatic Na+/bile acid cotransporters of the rabbit. II. A reliable 3D QSAR pharmacophore model for the ileal Na+/bile acid cotransporter," J. Lipid Res., 1999, 40:2158-2168.
Bass et al., "Inherited Disorders of Cholestasis in Adulthood," Clin. Liver. Dis., 2013, 2(5):200-203.
Charach et al., "The association of bile acid excretion and atherosclerotic coronary artery disease," Therapeutic Advances in Gastroenterology, 2011, 4(2):95-101.
Ellis et al. "Feedback regulation of human bile acid synthesis," Falk Symposium, 2005, 141:73-79.
Farmer et al., "Currently available hypolipidaemic drugs and future therapeutic developments," Baillieres Clin Endocrinol Metab, 1995, 9(4):825-47.
Glueck, "Colestipol and probucol: treatment of primary and familial hypercholesterolemia and amelioration of atherosclerosis," Ann. Intern. Med, Apr. 1982, 96(4): 475-82.
Guo et al., "Serum Metabolomic Analysis of Coronary Heart Disease Patients with Stable Angina Pectoris Subtyped by Traditional Chinese Medicine Diagnostics Reveals Biomarkers Relevant to Personalized Treatments," Frontiers in Pharmacology, Jun. 2022, 12:1-14.
Hofmann, "Defective Biliary Secretion during Total Parenteral Nutrition," J. Ped. Gastro. & Nutr, May 1995, 20(4):376-390.
Khurana et al., "Bile Acids Regulate Cardiovascular Function," Clin Transl Sci, Jun. 2011, 4(3):210-218.
Mehl et al. "Liver transplantation and the management of progressive familial intrahepatic cholestasis in children," World J. Transplant, 2016, 6(2):278-90.
Schonherr, "Profound Methyl Effects in Drug Discovery and a Call for New C-H Methylation Reactions," Angew. Chem. Int. Ed., 2013, 52:12256-12267.
Vasavan et al., "Heart and bile acids—Clinical consequences of altered bile acid metabolism," BBA—Molecular Basis of Disease, 2018, 1864:1345-1355.
PCT International Search Report and Written Opinion in International Application No. PCT/EP2021/084081, dated Jan. 27, 2022, 13 pages.
PCT International Search Report and Written Opinion in International Application No. PCT/EP2022/065165, dated Aug. 23, 2022, 9 pages.

(56) References Cited

OTHER PUBLICATIONS

Garsuch et al., "Comparative investigations on different polymers for the preparation of fast-dissolving oral films," Journal of Pharmacy and Pharmacology, 2010, 62:539-545.

Gildeeva, "Polymorphism: the influence on the quality of drugs and actual methods of analysis," Kachestvennaya Klinicheskaya Praktika= Good Clinical Practice, 2017, (1):56-60 (with English abstract).

Gordienko et al., "Chemistry and Technology of Drugs and Biologically Active Compounds," Bulletin of MITHT, 2010, 5(1):93-97 (with machine translation).

Russian Office Action in Russian Appln. No. 2021100978, dated Dec. 20, 2022, 16 pages.

Setkina et al., "Biopharmaceutical aspects of drug technology and ways to modify bioavailability," Vestnik VSUM, 2014, 12(4):162-172 (with English abstract).

"Formulation and Analytical Development for Low-Dose Oral Drug Products," Zheng ed., Feb. 2008, p. 40 and 218.

"The Theory and Practice of Industrial Pharmacy," 3rd Ed., 1987, p. 46.

\* cited by examiner

SEQUENCE LISTING

<160> NUMBER OF SEQ ID NOS: 4

<210> SEQ ID NO 1
<211> LENGTH: 1251
<212> TYPE: PRT
<213> ORGANISM: Homo sapiens

<400> SEQUENCE: 1

```
Met Ser Thr Glu Arg Asp Ser Glu Thr Thr Phe Asp Glu Asp Ser Gln
1               5                   10                  15

Pro Asn Asp Glu Val Val Pro Tyr Ser Asp Glu Thr Glu Asp Glu
            20                  25                  30

Leu Asp Asp Gln Gly Ser Ala Val Glu Pro Glu Gln Asn Arg Val Asn
        35                  40                  45

Arg Glu Ala Glu Glu Asn Arg Glu Pro Phe Arg Lys Glu Cys Thr Trp
50                  55                  60

Gln Val Lys Ala Asn Asp Arg Lys Tyr His Glu Gln Pro His Phe Met
65                  70                  75                  80

Asn Thr Lys Phe Leu Cys Ile Lys Glu Ser Lys Tyr Ala Asn Asn Ala
                85                  90                  95

Ile Lys Thr Tyr Lys Tyr Asn Ala Phe Thr Phe Ile Pro Met Asn Leu
            100                 105                 110

Phe Glu Gln Phe Lys Arg Ala Ala Asn Leu Tyr Phe Leu Ala Leu Leu
        115                 120                 125

Ile Leu Gln Ala Val Pro Gln Ile Ser Thr Leu Ala Trp Tyr Thr Thr
130                 135                 140

Leu Val Pro Leu Leu Val Val Leu Gly Val Thr Ala Ile Lys Asp Leu
145                 150                 155                 160

Val Asp Asp Val Ala Arg His Lys Met Asp Lys Glu Ile Asn Asn Arg
                165                 170                 175

Thr Cys Glu Val Ile Lys Asp Gly Arg Phe Lys Val Ala Lys Trp Lys
            180                 185                 190

Glu Ile Gln Val Gly Asp Val Ile Arg Leu Lys Lys Asn Asp Phe Val
        195                 200                 205

Pro Ala Asp Ile Leu Leu Leu Ser Ser Ser Glu Pro Asn Ser Leu Cys
210                 215                 220

Tyr Val Glu Thr Ala Glu Leu Asp Gly Glu Thr Asn Leu Lys Phe Lys
225                 230                 235                 240

Met Ser Leu Glu Ile Thr Asp Gln Tyr Leu Gln Arg Glu Asp Thr Leu
                245                 250                 255

Ala Thr Phe Asp Gly Phe Ile Glu Cys Glu Glu Pro Asn Asn Arg Leu
            260                 265                 270
```

-continued

```
Asp Lys Phe Thr Gly Thr Leu Phe Trp Arg Asn Thr Ser Phe Pro Leu
            275                 280                 285
Asp Ala Asp Lys Ile Leu Leu Arg Gly Cys Val Ile Arg Asn Thr Asp
290                 295                 300
Phe Cys His Gly Leu Val Ile Phe Ala Gly Ala Asp Thr Lys Ile Met
305                 310                 315                 320
Lys Asn Ser Gly Lys Thr Arg Phe Lys Arg Thr Lys Ile Asp Tyr Leu
            325                 330                 335
Met Asn Tyr Met Val Tyr Thr Ile Phe Val Val Leu Ile Leu Leu Ser
                340                 345                 350
Ala Gly Leu Ala Ile Gly His Ala Tyr Trp Glu Ala Gln Val Gly Asn
            355                 360                 365
Ser Ser Trp Tyr Leu Tyr Asp Gly Glu Asp Thr Pro Ser Tyr Arg
370                 375                 380
Gly Phe Leu Ile Phe Trp Gly Tyr Ile Ile Val Leu Asn Thr Met Val
385                 390                 395                 400
Pro Ile Ser Leu Tyr Val Ser Val Glu Val Ile Arg Leu Gly Gln Ser
            405                 410                 415
His Phe Ile Asn Trp Asp Leu Gln Met Tyr Tyr Ala Glu Lys Asp Thr
            420                 425                 430
Pro Ala Lys Ala Arg Thr Thr Thr Leu Asn Glu Gln Leu Gly Gln Ile
            435                 440                 445
His Tyr Ile Phe Ser Asp Lys Thr Gly Thr Leu Thr Gln Asn Ile Met
            450                 455                 460
Thr Phe Lys Lys Cys Cys Ile Asn Gly Gln Ile Tyr Gly Asp His Arg
465                 470                 475                 480
Asp Ala Ser Gln His Asn His Asn Lys Ile Glu Gln Val Asp Phe Ser
                485                 490                 495
Trp Asn Thr Tyr Ala Asp Gly Lys Leu Ala Phe Tyr Asp His Tyr Leu
            500                 505                 510
Ile Glu Gln Ile Gln Ser Gly Lys Glu Pro Glu Val Arg Gln Phe Phe
            515                 520                 525
Phe Leu Leu Ala Val Cys His Thr Val Met Val Asp Arg Thr Asp Gly
530                 535                 540
Gln Leu Asn Tyr Gln Ala Ala Ser Pro Asp Glu Gly Ala Leu Val Asn
545                 550                 555                 560
Ala Ala Arg Asn Phe Gly Phe Ala Phe Leu Ala Arg Thr Gln Asn Thr
                565                 570                 575
Ile Thr Ile Ser Glu Leu Gly Thr Glu Arg Thr Tyr Asn Val Leu Ala
            580                 585                 590
Ile Leu Asp Phe Asn Ser Asp Arg Lys Arg Met Ser Ile Ile Val Arg
            595                 600                 605
Thr Pro Glu Gly Asn Ile Lys Leu Tyr Cys Lys Gly Ala Asp Thr Val
610                 615                 620
Ile Tyr Glu Arg Leu His Arg Met Asn Pro Thr Lys Gln Glu Thr Gln
625                 630                 635                 640
Asp Ala Leu Asp Ile Phe Ala Asn Glu Thr Leu Arg Thr Leu Cys Leu
                645                 650                 655
Cys Tyr Lys Glu Ile Glu Glu Lys Glu Phe Thr Glu Trp Asn Lys Lys
            660                 665                 670
Phe Met Ala Ala Ser Val Ala Ser Thr Asn Arg Asp Glu Ala Leu Asp
            675                 680                 685
Lys Val Tyr Glu Glu Ile Glu Lys Asp Leu Ile Leu Leu Gly Ala Thr
```

```
            690             695             700
Ala Ile Glu Asp Lys Leu Gln Asp Gly Val Pro Glu Thr Ile Ser Lys
705             710             715             720

Leu Ala Lys Ala Asp Ile Lys Ile Trp Val Leu Thr Gly Asp Lys Lys
                725             730             735

Glu Thr Ala Glu Asn Ile Gly Phe Ala Cys Glu Leu Leu Thr Glu Asp
                740             745             750

Thr Thr Ile Cys Tyr Gly Glu Asp Ile Asn Ser Leu Leu His Ala Arg
            755             760             765

Met Glu Asn Gln Arg Asn Arg Gly Val Tyr Ala Lys Phe Ala Pro
    770             775             780

Pro Val Gln Glu Ser Phe Pro Pro Gly Gly Asn Arg Ala Leu Ile
785             790             795             800

Ile Thr Gly Ser Trp Leu Asn Glu Ile Leu Leu Glu Lys Lys Thr Lys
                805             810             815

Arg Asn Lys Ile Leu Lys Leu Lys Phe Pro Arg Thr Glu Glu Arg
            820             825             830

Arg Met Arg Thr Gln Ser Lys Arg Leu Glu Ala Lys Lys Glu Gln
            835             840             845

Arg Gln Lys Asn Phe Val Asp Leu Ala Cys Glu Cys Ser Ala Val Ile
850             855             860

Cys Cys Arg Val Thr Pro Lys Gln Lys Ala Met Val Val Asp Leu Val
865             870             875             880

Lys Arg Tyr Lys Lys Ala Ile Thr Leu Ala Ile Gly Asp Gly Ala Asn
            885             890             895

Asp Val Asn Met Ile Lys Thr Ala His Ile Gly Val Gly Ile Ser Gly
            900             905             910

Gln Glu Gly Met Gln Ala Val Met Ser Ser Asp Tyr Ser Phe Ala Gln
            915             920             925

Phe Arg Tyr Leu Gln Arg Leu Leu Leu Val His Gly Arg Trp Ser Tyr
            930             935             940

Ile Arg Met Cys Lys Phe Leu Arg Tyr Phe Phe Tyr Lys Asn Phe Ala
945             950             955             960

Phe Thr Leu Val His Phe Trp Tyr Ser Phe Asn Gly Tyr Ser Ala
                965             970             975

Gln Thr Ala Tyr Glu Asp Trp Phe Ile Thr Leu Tyr Asn Val Leu Tyr
            980             985             990

Thr Ser Leu Pro Val Leu Leu Met  Gly Leu Leu Asp Gln  Asp Val Ser
            995             1000            1005

Asp Lys  Leu Ser Leu Arg Phe  Pro Gly Leu Tyr Ile  Val Gly Gln
    1010            1015            1020

Arg Asp  Leu Leu Phe Asn Tyr  Lys Arg Phe Phe Val  Ser Leu Leu
    1025            1030            1035

His Gly  Val Leu Thr Ser Met  Ile Leu Phe Phe Ile  Pro Leu Gly
    1040            1045            1050

Ala Tyr  Leu Gln Thr Val Gly  Gln Asp Gly Glu Ala  Pro Ser Asp
    1055            1060            1065

Tyr Gln  Ser Phe Ala Val Thr  Ile Ala Ser Ala Leu  Val Ile Thr
    1070            1075            1080

Val Asn  Phe Gln Ile Gly Leu  Asp Thr Ser Tyr Trp  Thr Phe Val
    1085            1090            1095

Asn Ala  Phe Ser Ile Phe Gly  Ser Ile Ala Leu Tyr  Phe Gly Ile
    1100            1105            1110
```

| | | | | | | | | | | |
|---|---|---|---|---|---|---|---|---|---|---|
|Met|Phe|Asp|Phe|His|Ser|Ala|Gly|Ile|His|Val|Leu|Phe|Pro|Ser|
| |1115| | | |1120| | | |1125| | | | | |

Met Phe Asp Phe His Ser     Ala Gly Ile His Val Leu Phe Pro Ser
    1115            1120                1125

Ala Phe Gln Phe Thr Gly Thr Ala Ser Asn Ala Leu Arg Gln Pro
    1130                1135                1140

Tyr Ile Trp Leu Thr Ile Ile Leu Ala Val Ala Val Cys Leu Leu
    1145                1150                1155

Pro Val Val Ala Ile Arg Phe Leu Ser Met Thr Ile Trp Pro Ser
    1160                1165                1170

Glu Ser Asp Lys Ile Gln Lys His Arg Lys Arg Leu Lys Ala Glu
    1175                1180                1185

Glu Gln Trp Gln Arg Gln Gln Val Phe Arg Arg Gly Val Ser
    1190                1195                1200

Thr Arg Arg Ser Ala Tyr Ala Phe Ser His Gln Arg Gly Tyr Ala
    1205                1210                1215

Asp Leu Ile Ser Ser Gly Arg Ser Ile Arg Lys Lys Arg Ser Pro
    1220                1225                1230

Leu Asp Ala Ile Val Ala Asp Gly Thr Ala Glu Tyr Arg Arg Thr
    1235                1240                1245

Gly Asp Ser
    1250

<210> SEQ ID NO 2
<211> LENGTH: 3756
<212> TYPE: DNA
<213> ORGANISM: Homo sapiens

<400> SEQUENCE: 2

```
atgagtacag aaagagactc agaaacgaca tttgacgagg attctcagcc taatgacgaa      60
gtggttccct acagtgatga tgaaacagaa gatgaacttg atgaccaggg gtctgctgtt     120
gaaccagaac aaaaccgagt caacagggaa gcagaggaga accggagcc attcagaaaa      180
gaatgtacat ggcaagtcaa agcaaacgat cgcaagtacc acgaacaacc tcactttatg     240
aacacaaaat tcttgtgtat taaggagagt aaatatgcga ataatgcaat taaaacatac     300
aagtacaacg catttacctt tataccaatg aatctgtttg agcagtttaa agagcagcc      360
aatttatatt tcctggctct tcttatctta caggcagttc ctcaaatctc taccctggct     420
tggtacacca cactagtgcc cctgcttgtg gtgctgggcg tcactgcaat caagacctg      480
gtggacgatg tggctcgcca taaaatggat aaggaaatca acaataggac gtgtgaagtc     540
attaaggatg gcaggttcaa agttgctaag tggaaagaaa ttcaagttgg agacgtcatt     600
cgtctgaaaa aaaatgattt tgttccagct gacattctcc tgctgtctag ctctgagcct     660
aacagcctct gctatgtgga acagcagaa ctggatggaa aaaccaattt aaaatttaag      720
atgtcacttg aaatcacaga ccagtacctc aaagagaag atacattggc tacatttgat     780
ggttttattg aatgtgaaga acccaataac agactagata agtttacagg aacactattt     840
tggagaaaca caagttttcc tttggatgct gataaaattt tgttacgtgg ctgtgtaatt     900
aggaacaccg atttctgcca cggcttagtc atttttgcag gtgctgacac taaaataatg     960
aagaatagtg ggaaaaccag atttaaaaga actaaaattg attacttgat gaactacatg    1020
gtttacacga tctttgttgt tcttattctg ctttctgctg gtcttgccat cggccatgct    1080
tattgggaag cacaggtggg caattcctct tggtacctct atgatggaga agacgataca    1140
ccctcctacc gtggattcct catttttctgg ggctatatca ttgttctcaa caccatggta    1200
```

-continued

| | |
|---|---|
| cccatctctc tctatgtcag cgtggaagtg attcgtcttg acagagtca cttcatcaac | 1260 |
| tgggacctgc aaatgtacta tgctgagaag gacacacccg caaaagctag aaccaccaca | 1320 |
| ctcaatgaac agctcgggca gatccattat atcttctctg ataagacggg gacactcaca | 1380 |
| caaaatatca tgacctttaa aaagtgctgt atcaacgggc agatatatgg ggaccatcgg | 1440 |
| gatgcctctc aacacaacca caacaaaata gagcaagttg attttagctg gaatacatat | 1500 |
| gctgatggga agcttgcatt ttatgaccac tatcttattg agcaaatcca gtcaggaaaa | 1560 |
| gagccagaag tacgacagtt cttcttcttg ctcgcagttt gccacacagt catggtggat | 1620 |
| aggactgatg gtcagctcaa ctaccaggca gcctctcccg atgaaggtgc cctggtaaac | 1680 |
| gctgccagga actttggctt tgccttcctc gccaggaccc agaacaccat caccatcagt | 1740 |
| gaactgggca ctgaaaggac ttacaatgtt cttgccattt ggacttcaa cagtgaccgg | 1800 |
| aagcgaatgt ctatcattgt aagaacccca gaaggcaata tcaagcttta ctgtaaaggt | 1860 |
| gctgacactg ttatttatga acggttacat cgaatgaatc ctactaagca agaaacacag | 1920 |
| gatgccctgg atatctttgc aaatgaaact cttagaaccc tatgcctttg ctacaaggaa | 1980 |
| attgaagaaa aagaatttac agaatggaat aaaaagttta tggctgccag tgtggcctcc | 2040 |
| accaaccggg acgaagctct ggataaagta tatgaggaga ttgaaaaaga cttaattctc | 2100 |
| ctgggagcta cagctattga agacaagcta caggatggag ttccagaaac catttcaaaa | 2160 |
| cttgcaaaag ctgacattaa gatctgggtg cttactggga caaaaagga aactgctgaa | 2220 |
| aatataggat ttgcttgtga acttctgact gaagacacca ccatctgcta tggggaggat | 2280 |
| attaattctc ttcttcatgc aaggatggaa accagagga atagaggtgg cgtctacgca | 2340 |
| aagtttgcac ctcctgtgca ggaatctttt tttccacccg gtggaaaccg tgccttaatc | 2400 |
| atcactggtt cttggttgaa tgaaattctt ctcgagaaaa agaccaagag aaataagatt | 2460 |
| ctgaagctga agttcccaag aacagaagaa gaaagacgga tgcggaccca agtaaaagg | 2520 |
| aggctagaag ctaagaaaga gcagcggcag aaaaactttg tggacctggc ctgcgagtgc | 2580 |
| agcgcagtca tctgctgccg cgtcaccccc aagcagaagg ccatggtggt ggacctggtg | 2640 |
| aagaggtaca agaaagccat cacgctggcc atcgagatg gggccaatga cgtgaacatg | 2700 |
| atcaaaactg cccacattgg cgttggaata agtggacaag aaggaatgca agctgtcatg | 2760 |
| tcgagtgact attcctttgc tcagttccga tatctgcaga ggctactgct ggtgcatggc | 2820 |
| cgatggtctt acataaggat gtgcaagttc ctacgatact tcttttacaa aaactttgcc | 2880 |
| tttactttgg ttcatttctg gtactccttc ttcaatggct actctgcgca gactgcatac | 2940 |
| gaggattggt tcatcacccct ctacaacgtg ctgtacacca gcctgccgt gctcctcatg | 3000 |
| gggctgctcg accaggatgt gagtgacaaa ctgagcctcc gattccctgg gttatacata | 3060 |
| gtgggacaaa gagacttact attcaactat aagagattct tgtaagctt gttgcatggg | 3120 |
| gtcctaacat cgatgatcct cttcttcata cctcttggag cttatctgca aaccgtaggg | 3180 |
| caggatggag aggcaccttc cgactaccag tcttttgccg tcaccattgc ctctgctctt | 3240 |
| gtaataacag tcaatttcca gattggcttg gatacttctt attggacttt tgtgaatgct | 3300 |
| ttttcaattt ttgaagcat tgcactttat tttggcatca tgtttgactt tcatagtgct | 3360 |
| ggaatacatg ttctcttcc atctgcattt caatttacag gcacagcttc aaacgctctg | 3420 |
| agacagccat acatttggtt aactatcatc ctggctgttg ctgtgtgctt actacccgtc | 3480 |
| gttgccattc gattcctgtc aatgaccatc tggcctcag aaagtgataa gatccagaag | 3540 |
| catcgcaagc ggttgaaggc ggaggagcag tggcagcgac ggcagcaggt gttccgccgg | 3600 |

```
ggcgtgtcaa cgcggcgctc ggcctacgcc ttctcgcacc agcggggcta cgcggacctc    3660
atctcctccg ggcgcagcat ccgcaagaag cgctcgccgc ttgatgccat cgtggcggat    3720
ggcaccgcgg agtacaggcg caccggggac agctga                              3756
```

<210> SEQ ID NO 3
<211> LENGTH: 1321
<212> TYPE: PRT
<213> ORGANISM: Homo sapiens

<400> SEQUENCE: 3

```
Met Ser Asp Ser Val Ile Leu Arg Ser Ile Lys Lys Phe Gly Glu Glu
1               5                   10                  15

Asn Asp Gly Phe Glu Ser Asp Lys Ser Tyr Asn Asn Asp Lys Lys Ser
            20                  25                  30

Arg Leu Gln Asp Glu Lys Lys Gly Asp Gly Val Arg Val Gly Phe Phe
        35                  40                  45

Gln Leu Phe Arg Phe Ser Ser Thr Asp Ile Trp Leu Met Phe Val
    50                  55                  60

Gly Ser Leu Cys Ala Phe Leu His Gly Ile Ala Gln Pro Gly Val Leu
65                  70                  75                  80

Leu Ile Phe Gly Thr Met Thr Asp Val Phe Ile Asp Tyr Asp Val Glu
                85                  90                  95

Leu Gln Glu Leu Gln Ile Pro Gly Lys Ala Cys Val Asn Asn Thr Ile
            100                 105                 110

Val Trp Thr Asn Ser Ser Leu Asn Gln Asn Met Thr Asn Gly Thr Arg
        115                 120                 125

Cys Gly Leu Leu Asn Ile Glu Ser Glu Met Ile Lys Phe Ala Ser Tyr
    130                 135                 140

Tyr Ala Gly Ile Ala Val Ala Val Leu Ile Thr Gly Tyr Ile Gln Ile
145                 150                 155                 160

Cys Phe Trp Val Ile Ala Ala Arg Gln Ile Gln Lys Met Arg Lys
                165                 170                 175

Phe Tyr Phe Arg Arg Ile Met Arg Met Glu Ile Gly Trp Phe Asp Cys
            180                 185                 190

Asn Ser Val Gly Glu Leu Asn Thr Arg Phe Ser Asp Asp Ile Asn Lys
        195                 200                 205

Ile Asn Asp Ala Ile Ala Asp Gln Met Ala Leu Phe Ile Gln Arg Met
    210                 215                 220

Thr Ser Thr Ile Cys Gly Phe Leu Leu Gly Phe Phe Arg Gly Trp Lys
225                 230                 235                 240

Leu Thr Leu Val Ile Ile Ser Val Ser Pro Leu Ile Gly Ile Gly Ala
                245                 250                 255

Ala Thr Ile Gly Leu Ser Val Ser Lys Phe Thr Asp Tyr Glu Leu Lys
            260                 265                 270

Ala Tyr Ala Lys Ala Gly Val Val Ala Asp Glu Val Ile Ser Ser Met
        275                 280                 285

Arg Thr Val Ala Ala Phe Gly Gly Glu Lys Arg Glu Val Glu Arg Tyr
    290                 295                 300

Glu Lys Asn Leu Val Phe Ala Gln Arg Trp Gly Ile Arg Lys Gly Ile
305                 310                 315                 320

Val Met Gly Phe Phe Thr Gly Phe Val Trp Cys Leu Ile Phe Leu Cys
                325                 330                 335

Tyr Ala Leu Ala Phe Trp Tyr Gly Ser Thr Leu Val Leu Asp Glu Gly
```

```
            340                 345                 350
Glu Tyr Thr Pro Gly Thr Leu Val Gln Ile Phe Leu Ser Val Ile Val
            355                 360                 365

Gly Ala Leu Asn Leu Gly Asn Ala Ser Pro Cys Leu Glu Ala Phe Ala
370                 375                 380

Thr Gly Arg Ala Ala Thr Ser Ile Phe Glu Thr Ile Asp Arg Lys
385                 390                 395                 400

Pro Ile Ile Asp Cys Met Ser Glu Asp Gly Tyr Lys Leu Asp Arg Ile
                    405                 410                 415

Lys Gly Glu Ile Glu Phe His Asn Val Thr Phe His Tyr Pro Ser Arg
                420                 425                 430

Pro Glu Val Lys Ile Leu Asn Asp Leu Asn Met Val Ile Lys Pro Gly
            435                 440                 445

Glu Met Thr Ala Leu Val Gly Pro Ser Gly Ala Gly Lys Ser Thr Ala
        450                 455                 460

Leu Gln Leu Ile Gln Arg Phe Tyr Asp Pro Cys Glu Gly Met Val Thr
465                 470                 475                 480

Val Asp Gly His Asp Ile Arg Ser Leu Asn Ile Gln Trp Leu Arg Asp
                485                 490                 495

Gln Ile Gly Ile Val Glu Gln Glu Pro Val Leu Phe Ser Thr Thr Ile
                500                 505                 510

Ala Glu Asn Ile Arg Tyr Gly Arg Glu Asp Ala Thr Met Glu Asp Ile
            515                 520                 525

Val Gln Ala Ala Lys Glu Ala Asn Ala Tyr Asn Phe Ile Met Asp Leu
        530                 535                 540

Pro Gln Gln Phe Asp Thr Leu Val Gly Glu Gly Gly Gln Met Ser
545                 550                 555                 560

Gly Gly Gln Lys Gln Arg Val Ala Ile Ala Arg Ala Leu Ile Arg Asn
                565                 570                 575

Pro Lys Ile Leu Leu Leu Asp Met Ala Thr Ser Ala Leu Asp Asn Glu
                580                 585                 590

Ser Glu Ala Met Val Gln Glu Val Leu Ser Lys Ile Gln His Gly His
            595                 600                 605

Thr Ile Ile Ser Val Ala His Arg Leu Ser Thr Val Arg Ala Ala Asp
        610                 615                 620

Thr Ile Ile Gly Phe Glu His Gly Thr Ala Val Glu Arg Gly Thr His
625                 630                 635                 640

Glu Glu Leu Leu Glu Arg Lys Gly Val Tyr Phe Thr Leu Val Thr Leu
                645                 650                 655

Gln Ser Gln Gly Asn Gln Ala Leu Asn Glu Glu Asp Ile Lys Asp Ala
                660                 665                 670

Thr Glu Asp Asp Met Leu Ala Arg Thr Phe Ser Arg Gly Ser Tyr Gln
            675                 680                 685

Asp Ser Leu Arg Ala Ser Ile Arg Gln Arg Ser Lys Ser Gln Leu Ser
        690                 695                 700

Tyr Leu Val His Glu Pro Pro Leu Ala Val Val Asp His Lys Ser Thr
705                 710                 715                 720

Tyr Glu Glu Asp Arg Lys Asp Lys Asp Ile Pro Val Gln Glu Val
                725                 730                 735

Glu Pro Ala Pro Val Arg Arg Ile Leu Lys Phe Ser Ala Pro Glu Trp
            740                 745                 750

Pro Tyr Met Leu Val Gly Ser Val Gly Ala Ala Val Asn Gly Thr Val
        755                 760                 765
```

```
Thr Pro Leu Tyr Ala Phe Leu Phe Ser Gln Ile Leu Gly Thr Phe Ser
    770                 775                 780

Ile Pro Asp Lys Glu Glu Gln Arg Ser Gln Ile Asn Gly Val Cys Leu
785                 790                 795                 800

Leu Phe Val Ala Met Gly Cys Val Ser Leu Phe Thr Gln Phe Leu Gln
                805                 810                 815

Gly Tyr Ala Phe Ala Lys Ser Gly Glu Leu Leu Thr Lys Arg Leu Arg
                820                 825                 830

Lys Phe Gly Phe Arg Ala Met Leu Gly Gln Asp Ile Ala Trp Phe Asp
    835                 840                 845

Asp Leu Arg Asn Ser Pro Gly Ala Leu Thr Thr Arg Leu Ala Thr Asp
    850                 855                 860

Ala Ser Gln Val Gln Gly Ala Ala Gly Ser Gln Ile Gly Met Ile Val
865                 870                 875                 880

Asn Ser Phe Thr Asn Val Thr Val Ala Met Ile Ile Ala Phe Ser Phe
                885                 890                 895

Ser Trp Lys Leu Ser Leu Val Ile Leu Cys Phe Phe Pro Phe Leu Ala
                900                 905                 910

Leu Ser Gly Ala Thr Gln Thr Arg Met Leu Thr Gly Phe Ala Ser Arg
    915                 920                 925

Asp Lys Gln Ala Leu Glu Met Val Gly Gln Ile Thr Asn Glu Ala Leu
    930                 935                 940

Ser Asn Ile Arg Thr Val Ala Gly Ile Gly Lys Glu Arg Arg Phe Ile
945                 950                 955                 960

Glu Ala Leu Glu Thr Glu Leu Glu Lys Pro Phe Lys Thr Ala Ile Gln
                965                 970                 975

Lys Ala Asn Ile Tyr Gly Phe Cys Phe Ala Phe Ala Gln Cys Ile Met
    980                 985                 990

Phe Ile Ala Asn Ser Ala Ser Tyr Arg Tyr Gly Gly Tyr Leu Ile Ser
    995                 1000                1005

Asn Glu Gly Leu His Phe Ser Tyr Val Phe Arg Val Ile Ser Ala
    1010                1015                1020

Val Val Leu Ser Ala Thr Ala Leu Gly Arg Ala Phe Ser Tyr Thr
    1025                1030                1035

Pro Ser Tyr Ala Lys Ala Lys Ile Ser Ala Ala Arg Phe Phe Gln
    1040                1045                1050

Leu Leu Asp Arg Gln Pro Pro Ile Ser Val Tyr Asn Thr Ala Gly
    1055                1060                1065

Glu Lys Trp Asp Asn Phe Gln Gly Lys Ile Asp Phe Val Asp Cys
    1070                1075                1080

Lys Phe Thr Tyr Pro Ser Arg Pro Asp Ser Gln Val Leu Asn Gly
    1085                1090                1095

Leu Ser Val Ser Ile Ser Pro Gly Gln Thr Leu Ala Phe Val Gly
    1100                1105                1110

Ser Ser Gly Cys Gly Lys Ser Thr Ser Ile Gln Leu Leu Glu Arg
    1115                1120                1125

Phe Tyr Asp Pro Asp Gln Gly Lys Val Met Ile Asp Gly His Asp
    1130                1135                1140

Ser Lys Lys Val Asn Val Gln Phe Leu Arg Ser Asn Ile Gly Ile
    1145                1150                1155

Val Ser Gln Glu Pro Val Leu Phe Ala Cys Ser Ile Met Asp Asn
    1160                1165                1170
```

| | | | | | | | | | | |
|---|---|---|---|---|---|---|---|---|---|---|
|Ile|Lys|Tyr|Gly|Asp|Asn|Thr|Lys|Glu|Ile|Pro|Met|Glu|Arg|Val|
|1175| | | | |1180| | | | |1185| | | | |

Ile Ala Ala Ala Lys Gln Ala Gln Leu His Asp Phe Val Met Ser
1190                    1195                    1200

Leu Pro Glu Lys Tyr Glu Thr Asn Val Gly Ser Gln Gly Ser Gln
1205                    1210                    1215

Leu Ser Arg Gly Glu Lys Gln Arg Ile Ala Ile Ala Arg Ala Ile
1220                    1225                    1230

Val Arg Asp Pro Lys Ile Leu Leu Leu Asp Glu Ala Thr Ser Ala
1235                    1240                    1245

Leu Asp Thr Glu Ser Glu Lys Thr Val Gln Val Ala Leu Asp Lys
1250                    1255                    1260

Ala Arg Glu Gly Arg Thr Cys Ile Val Ile Ala His Arg Leu Ser
1265                    1270                    1275

Thr Ile Gln Asn Ala Asp Ile Ile Ala Val Met Ala Gln Gly Val
1280                    1285                    1290

Val Ile Glu Lys Gly Thr His Glu Glu Leu Met Ala Gln Lys Gly
1295                    1300                    1305

Ala Tyr Tyr Lys Leu Val Thr Thr Gly Ser Pro Ile Ser
1310                    1315                    1320

<210> SEQ ID NO 4
<211> LENGTH: 3966
<212> TYPE: DNA
<213> ORGANISM: Homo sapiens

<400> SEQUENCE: 4

```
atgtctgact cagtaattct tcgaagtata aagaaatttg gagaggagaa tgatggtttt      60
gagtcagata atcatataaa taatgataag aaatcaaggt tacaagatga aagaaaggt     120 gatggcgtta gagttggctt cttttcaattg tttcggtttt cttcatcaac tgacatttgg    180
ctgatgtttg tgggaagttt gtgtgcattt ctccatggaa tagcccagcc aggcgtgcta    240
ctcatttttg gcacaatgac agatgttttt attgactacg acgttgagtt acaagaactc    300
cagattccag aaaagcatg tgtgaataac accattgtat ggactaacag ttccctcaac    360
cagaacatga caaatggaac acgttgtggg ttgctgaaca tcgagagcga aatgatcaaa    420
tttgccagtt actatgctgg aattgctgtc gcagtactta tcacaggata tattcaaata    480
tgcttttggg tcattgccgc agctcgtcag atacagaaaa tgagaaaatt ttactttagg    540
agaataatga aatggaaat agggtggttt gactgcaatt cagtgggga gctgaataca    600 agattctctg atgatattaa taaaatcaat gatgccatag ctgaccaaat ggccttttc    660 attcagcgca tgacctcgac catctgtggt ttcctgttgg attttttcag gggttggaaa    720
ctgaccttgg ttattattc tgtcagccct ctcattggga ttggagcagc caccattggt    780
ctgagtgtgt ccaagtttac ggactatgag ctgaaggcct atgccaaagc aggggtggtg    840
gctgatgaag tcatttcatc aatgagaaca gtggctgctt ttggtggtga aaaagagag    900 gttgaaaggt atgagaaaaa tcttgtgttc gcccagcgtt ggggaattag aaaaggaata    960
gtgatgggat tctttactgg attcgtgtgg tgtctcatct ttttgtgtta tgcactggcc   1020
ttctggtacg gctccacact tgtcctggat gaaggagaat ataccaccag aaccettgtc   1080 cagatttcc tcagtgtcat agtaggagct ttaaatctg caatgcctc tccttgttg     1140 gaagcctttg caactggacg tgcagcagcc accagcattt ttgagacaat agacaggaa   1200 cccatcattg actgcatgtc agaagatggt tacaagttgg atcgaatcaa gggtgaaatt   1260
```

-continued

```
gaattccata atgtgacctt ccattatcct tccagaccag aggtgaagat tctaaatgac    1320
ctcaacatgg tcattaaacc aggggaaatg acagctctgg taggacccag tggagctgga    1380
aaaagtacag cactgcaact cattcagcga ttctatgacc cctgtgaagg aatggtgacc    1440
gtggatggcc atgacattcg ctctcttaac attcagtggc ttagagatca gattgggata    1500
gtggagcaag agccagttct gttctctacc accattgcag aaaatattcg ctatggcaga    1560
gaagatgcaa caatggaaga catagtccaa gctgccaagg aggccaatgc ctacaacttc    1620
atcatggacc tgccacagca atttgacacc cttgttggag aaggaggagg ccagatgagt    1680
ggtggccaga acaaagggt agctatcgcc agagccctca tccgaaatcc caagattctg    1740
cttttggaca tggccaccct agctctggac aatgagagtg aagccatggt gcaagaagtg    1800
ctgagtaaga ttcagcatgg gcacacaatc atttcagttg ctcatcgctt gtctacggtc    1860
agagctgcag ataccatcat tggttttgaa catggcactg cagtggaaag agggacccat    1920
gaagaattac tggaaaggaa aggtgtttac ttcactctag tgactttgca aagccaggga    1980
aatcaagctc ttaatgaaga ggacataaag gatgcaactg aagatgacat gcttgcgagg    2040
acctttagca gagggagcta ccaggatagt ttaagggctt ccatccggca acgctccaag    2100
tctcagcttt cttacctggt gcacgaacct ccattagctg ttgtagatca taagtctacc    2160
tatgaagaag atagaaagga caaggacatt cctgtgcagg aagaagttga acctgcccca    2220
gttaggagga ttctgaaatt cagtgctcca gaatggccct acatgctggt agggtctgtg    2280
ggtgcagctg tgaacgggac agtcacaccc ttgtatgcct ttttattcag ccagattctt    2340
gggactttt caattcctga taagaggaa caaaggtcac agatcaatgg tgtgtgccta    2400
cttttttgtag caatgggctg tgtatctctt ttcacccaat ttctacaggg atatgccttt    2460
gctaaatctg gggagctcct aacaaaaagg ctacgtaaat ttggtttcag ggcaatgctg    2520
gggcaagata ttgcctggtt tgatgacctc agaaatagcc ctggagcatt gacaacaaga    2580
cttgctacag atgcttccca agttcaaggg gctgccggct ctcagatcgg gatgatagtc    2640
aattccttca ctaacgtcac tgtggccatg atcattgcct ctccttag ctggaagctg    2700
agcctggtca tcttgtgctt cttccccttc ttggctttat caggagccac acagaccagg    2760
atgttgacag gatttgcctc tcgagataag caggccctgg agatggtggg acagattaca    2820
aatgaagccc tcagtaacat ccgcactgtt gctggaattg aaaggagag gcggttcatt    2880
gaagcacttg agactgagct ggagaagccc ttcaagacag ccattcagaa agccaatatt    2940
tacggattct gctttgcctt tgcccagtgc atcatgttta ttgcgaattc tgcttcctac    3000
agatatggag ttacttaat ctccaatgag gggctccatt tcagctatgt gttcagggtg    3060
atctctgcag ttgtactgag tgcaacagct cttggaagag ccttctctta cacccccaagt    3120
tatgcaaaag ctaaaatatc agctgcacgc ttttttcaac tgctggaccg acaaccccca    3180
atcagtgtat acaatactgc aggtgaaaaa tgggacaact tccagggggaa gattgatttt    3240
gttgattgta aatttacata tccttctcga cctgactcgc aagttctgaa tggtctctca    3300
gtgtcgatta gtccagggca gacactggcg tttgttggga gcagtggatg tggcaaaagc    3360
actagcattc agctgttgga acgtttctat gatcctgatc aagggaaggt gatgatagat    3420
ggtcatgaca gcaaaaaagt aaatgtccag ttcctccgct caaacattgg aattgtttcc    3480
caggaaccag tgttgtttgc ctgtagcata atggacaata tcaagtatgg agacaacacc    3540
aaagaaattc ccatggaaag agtcatagca gctgcaaaac aggctcagct gcatgatttt    3600
```

```
gtcatgtcac tcccagagaa atatgaaact aacgttgggt cccagggggtc tcaactctct    3660 agagggggaga aacaacgcat tgctattgct cgggccattg tacgagatcc taaaatcttg    3720
ctactagatg aagccacttc tgccttagac acagaaagtg aaaagacggt gcaggttgct    3780
ctagacaaag ccagagaggg tcggacctgc attgtcattg cccatcgctt gtccaccatc    3840
cagaacgcgg atatcattgc tgtcatggca caggggggtgg tgattgaaaa ggggacccat    3900
gaagaactga tggcccaaaa aggagcctac tacaaactag tcaccactgg atcccccatc    3960
agttga                                                                3966
```

PHARMACEUTICAL FORMULATION OF ODEVIXIBAT

CROSS-REFERENCE TO RELATED APPLICATIONS

This application is a continuation of U.S. application Ser. No. 16/477,160, filed Jul. 10, 2019, which is a National Stage application under 35 U.S.C. § 371 of International Application No. PCT/SE2019/050603, filed Jun. 20, 2019, which claims priority to Swedish Application No. 1850761-6, filed Jun. 20, 2018, and to Swedish Application No. 1850762-4, filed Jun. 20, 2018, the disclosures of which are incorporated by reference herein in their entireties.

TECHNICAL FIELD

The invention relates to a pharmaceutical formulation, e.g. a paediatric formulation, of odevixibat, which comprises a plurality of small particles. The formulation may be used in the treatment of liver diseases, such as bile acid-dependent liver diseases, and particularly cholestatic liver diseases such as biliary atresia, progressive familial intrahepatic cholestasis (PFIC), Alagille syndrome (ALGS) and paediatric cholestatic pruritus. The invention also relates to a process for the preparation of the pharmaceutical formulation.

BACKGROUND

The compound 1,1-dioxo-3,3-dibutyl-5-phenyl-7-methyl-thio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine (odevixibat; also known as A4250) is disclosed in WO 03/022286. The structure of odevixibat is shown below.

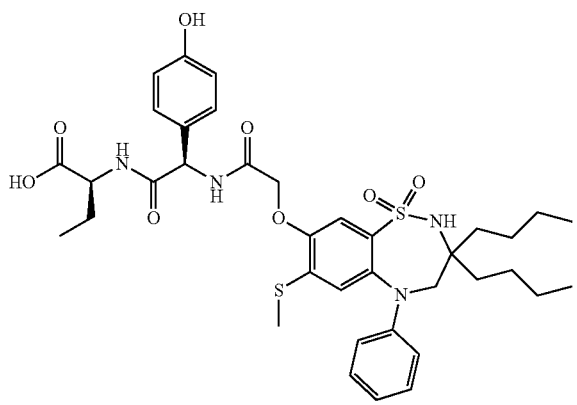 [SMILES: CCCCC1(CCCC)CN(c2ccccc2)c2cc(SC)c(OCC(=O)N[C@@H](C(=O)N[C@@H](CC)C(=O)O)c3ccc(O)cc3)cc2S(=O)(=O)N1]

As an inhibitor of the ileal bile acid transport (IBAT) mechanism, odevixibat inhibits the natural reabsorption of bile acids from the ileum into the hepatic portal circulation. Bile acids that are not reabsorbed from the ileum are instead excreted into the faeces. The overall removal of bile acids from the enterohepatic circulation leads to a decrease in the level of bile acids in serum and the liver. Odevixibat, or a pharmaceutically acceptable salt thereof, is therefore useful in the treatment of liver diseases that are associated with elevated bile acid levels, and particularly in the treatment of rare paediatric cholestatic liver diseases.

Odevixibat exhibits high potency and should be administered in low doses, such as ranging from about 40 to about 120 µg/kg. This corresponds to doses as low as 200 to 800 µg in the treatment of paediatric patients that weigh about 5 to 20 kg (e.g., infants and toddlers). It is desirable that a formulation of odevixibat can be administered to young patients in a dosage form having a small size. It is further desirable that such a formulation has good palatability, is not perceived as gritty, and is well-tolerated by infants and small children.

Multiparticulates can be administered to infants from birth if they are administered with a liquid. For children aged approximately 6 months and older (i.e. after weaning), the multiparticulates can be administered in their solid form either directly into the mouth or mixed with semi-solid food. Particle size, shape, texture, hardness, taste and dose volume (i.e., the number of particles) have been reported to be important for acceptability of multiparticulates by infants and children (Kozarewicz, Int. J. Pharm. 2014, vol. 469, pp 245-248). Various literature reviews have been conducted on the acceptability of different oral dosage forms in paediatric and older adult patients (see e.g. Liu, et al., Drugs 2014, vol. 74, pp. 1871-1889; Drumond et al., Int. J. Pharm. 2017, vol. 521, pp. 294-305; Mistry et al., J. Pharm. Pharmacol. 2017, vol. 69, pp. 361-376; Walsh et al., Int. J. Pharm. 2017, vol. 536, pp. 547-562), but the size and/or dose volume (amount) of multiparticulates investigated have not always been reported in these reviews.

Perception of grittiness may be influenced by a range of factors including particle size, quantity and dosing vehicle (see Mishra et al., Yakugaku Zasshi 2009, vol. 129, pp. 1537-1544; Lopez et al., Eur. J. Pharm. Sci. 2016, vol. 92, pp. 156-162) as well as the hardness and shape of the particles (Tyle, Acta Psychologica 1993, vol. 84, pp. 111-118), with irregular particles being perceived as larger than round (spherical) particles of the same size (Engelen et al., J. Text. Studies 2005, vol. 36, pp. 373-386). Grittiness perception studies have shown that grittiness scores may increase with increasing size and dose of the multiparticulates, whereas grittiness scores may decrease with increasing vehicle viscosity (Lopez et al., Eur. J. Pharm. Sci. 2016, vol. 92, pp. 156-162).

Capsules can be acceptable for children from approximately 6 years of age. The swallowability of the capsules can depend upon the dosage form dimensions (i.e. the size) and the ability of the child. The size, shape, taste and after taste are important capsule attributes that can influence patient acceptability (Kozarewicz, Int. J. Pharm. 2014, vol. 469, pp 245-248). In some embodiments, the size of the capsules is kept as small as possible, and the number of capsules required per dose is kept to a minimum, e.g. not more than 1-3 capsules.

In view of the above, there is a need for a formulation of odevixibat that can be easily administered in small doses adapted to the patients' weight. In some embodiments, the formulation should be suitable for treating very young patients, should be easy to swallow, and should not be perceived as gritty.

DETAILED DESCRIPTION OF THE INVENTION

Figure 1:
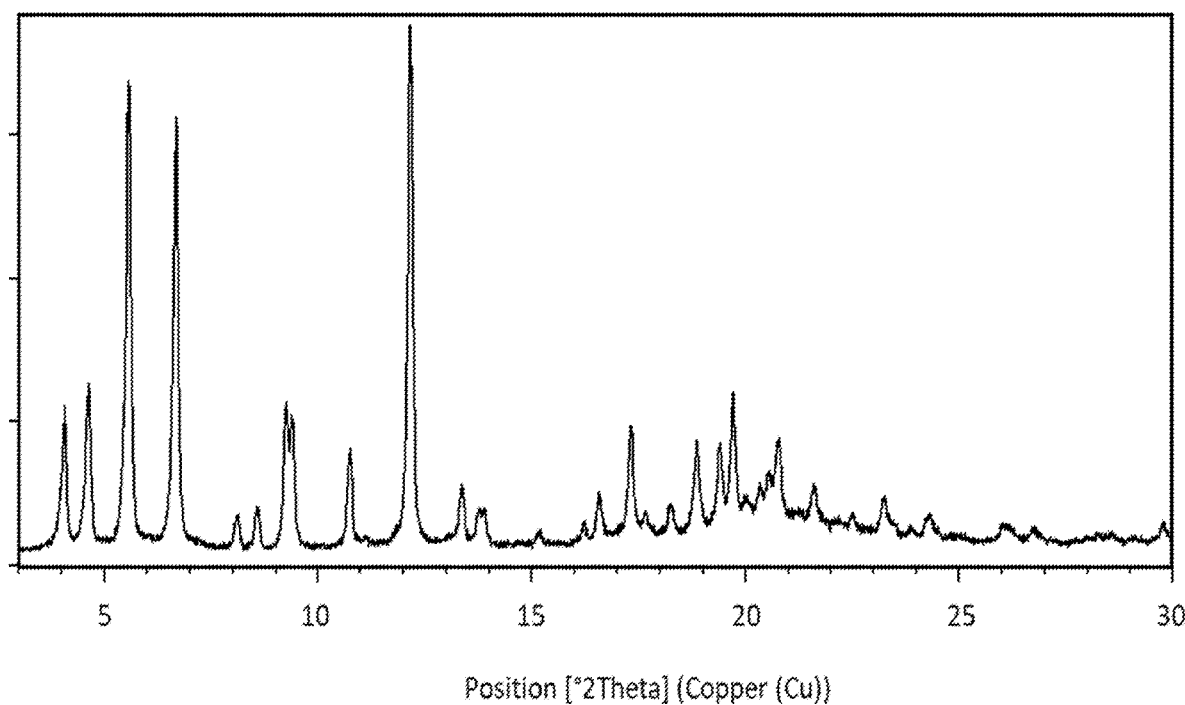
FIG. 1 shows the X-ray powder diffractogram of dried crystal modification 1.

Provided herein is a multiparticulate formulation containing low doses of odevixibat. In some embodiments, the formulation is a paediatric formulation. In some embodiments, the formulation enables weight-based dosing and can be sprinkled onto food. The formulation can be designed to have a good palatability, with an optimal balance between particle size and dose volume.

In a first aspect, the invention relates to a pharmaceutical formulation of odevixibat, comprising a plurality of particles, wherein each particle contains odevixibat, or a pharmaceutically acceptable salt thereof, in an amount of from about 0.1% w/w to about 5.0% w/w based on the total weight of the particle.

Because of the low doses in which odevixibat is to be administered, and further because of the multiparticulate form of the application, each particle of the formulation contains only a very low amount of the active ingredient. For example, the amount of odevixibat, or a pharmaceutically acceptable salt thereof, in each particle can be from about 0.2% w/w to about 3.5% w/w, preferably from about 0.3% w/w to about 3.0% w/w, more preferably from about 0.4% w/w to about 2.5% w/w, and most preferably from about 0.5% w/w to about 2.0% w/w based on the total weight of the particle. In one preferred embodiment, each particle contains odevixibat, or a pharmaceutically acceptable salt thereof, in an amount of about 0.5% w/w based on the total weight of the particle. In another preferred embodiment, each particle contains odevixibat, or a pharmaceutically acceptable salt thereof, in an amount of about 1.0% w/w based on the total weight of the particle. In yet another preferred embodiment, each particle contains odevixibat, or a pharmaceutically acceptable salt thereof, in an amount of about 1.5% w/w based on the total weight of the particle.

As used herein, the term "particles" refers to small particles ranging in size from about 0.1 to about 1.5 mm. Such particles are preferably essentially spherical, although elongated or oblong particles also might be used. The particles may e.g. be pellets, beads, microparticles, microspheres, granules or minitablets, and may optionally be coated with one or more coating layers surrounding every such pellet, bead, microparticle, microsphere, granule or minitablet.

In some embodiments, the particles of the formulation are small enough, that they can be sprinkled onto food and easily swallowed. In some embodiments, the particles can be swallowed without causing a perception of grittiness. In some embodiments, the particles do not give the patient an urge to chew the particles. The particles are, therefore, preferably between about 0.1 and about 1.5 mm in size, more preferably between about 0.1 and about 1.0 mm, and more preferably between about 0.1 and 0.8 mm, such as about 0.2 mm, about 0.3 mm, about 0.4 mm, about 0.5 mm, about 0.6 mm, or about 0.7 mm. In a more preferred embodiment, the particles are between about 0.4 and about 0.8 mm, such as about 0.5 mm, or such as about 0.6 mm, or such as about 0.7 mm. In a particular embodiment of the invention, the particles are about 0.7 mm.

In some embodiments, the invention relates to a formulation of odevixibat, wherein each particle comprises a core and a coating layer surrounding the core. The core of each particle may be a pellet, a granule, a minitablet, a bead, a microparticle or a microsphere.

In some embodiments, the core of each particle comprises the active pharmaceutical ingredient (odevixibat), while the coating layer of each particle does not comprise the active pharmaceutical ingredient. In some embodiments, the core of each particle comprises from about 0.1% to about 5% w/w of the active pharmaceutical ingredient, based on the total weight of the particle, such as from about 0.1% to about 2% w/w, such as from about 0.1% to about 1% w/w, or such as from about 0.1% to about 0.5% w/w of the active pharmaceutical ingredient, based on the total weight of the particle.

In some embodiments, the coating layer of each particle comprises the active pharmaceutical ingredient (odevixibat), while the core of each particle does not comprise the active pharmaceutical ingredient. In some embodiments, the coating layer of each particle comprises from about 0.1% to about 5% w/w of the active pharmaceutical ingredient, based on the total weight of the particle, such as from about 0.1% to about 2% w/w, such as from about 0.1% to about 1% w/w, or such as from about 0.1% to about 0.5% w/w of the active pharmaceutical ingredient, based on the total weight of the particle.

The cores may be orally dispersible and comprise soluble ingredients such as a sugar (e.g., sucrose) or a soluble polymer (e.g. hydroxypropyl methylcellulose) or may be non-orally dispersible and comprise non-soluble ingredients such as a non-soluble polymer (e.g., microcrystalline cellulose). In a preferred embodiment of the invention, the cores comprise microcrystalline cellulose. In a more preferred embodiment, the cores are microcrystalline cellulose spheres.

The coating layer can further comprise a film-forming polymer, such as a cellulose-based polymer, a polysaccharide-based polymer, an N-vinylpyrrolidone-based polymer, an acrylate, an acrylamide, or copolymers thereof. Examples of suitable film-forming polymers include polyvinyl alcohol (PVA), polyvinyl acetate phthalate (PVAP), polyethylene glycol (PEG), polyvinylpyrrolidone (PVP), methacrylic acid copolymers, starch, hydroxypropyl starch, chitosan, shellac, methyl cellulose, hydroxypropyl cellulose (HPC), low-substituted hydroxypropyl cellulose, hydroxypropyl methylcellulose (HPMC; or hypromellose), hydroxypropyl methylcellulose acetate succinate (HPMCAS), hydroxypropyl methylcellulose phthalate (HPMCP), cellulose acetate phthalate (CAP), cellulose acetate trimellitate (CAT), as well as combinations thereof, such as a mixture of methyl cellulose and hydroxypropyl methylcellulose (metolose). In a preferred embodiment, the coating layer comprises a film-forming polymer selected from the group consisting of hydroxypropyl methylcellulose, polyvinyl alcohol (PVA), polyethylene glycol (PEG), starch, hydroxypropyl starch and hydroxypropyl cellulose (HPC). In a most preferred embodiment, the coating layer comprises hydroxypropyl methylcellulose as the film-forming polymer.

The coating layer may optionally comprise one or more additional ingredients, such as a plasticizer (e.g. polyethylene glycol, triacetin or triethyl citrate), an anti-tack agent (e.g. talc or magnesium stearate) or a colouring agent (e.g. titanium dioxide, iron oxides, riboflavin or turmeric).

In some embodiments, the formulation comprises odevixibat in crystalline form. In some embodiments, the formulation comprises a crystalline hydrate of odevixibat. In some embodiments, the formulation comprises crystal modification 1 of odevixibat. This stable crystal modification can be obtained from a slurry of odevixibat in a mixture of water and an organic solvent such as ethanol. Under these conditions, a mixed solvate containing about two moles of water and about one to about three, such as about two to about three, moles of ethanol per mole of odevixibat (e.g., a dihydrate-diethanolate or a dihydrate-triethanolate) is initially formed. This mixed solvate is referred to herein as crystal modification 2. When crystal modification 2 is dried, such as under vacuum (e.g., less than 5 mbar) or under a nitrogen flow, it loses its organic solvent molecules and becomes crystal modification 1. In some embodiments, the transformation of crystal modification 2 to crystal modification 1 proceeds via a crystalline intermediate. It is believed that this crystalline intermediate is a dehydrated form, which quickly takes up water from the air. While not wishing to be bound by theory, it is believed that the solvent molecules can be removed without dissolution and recrystallization of the crystals.

Crystal modification 1 of odevixibat cannot only be obtained from a mixture of water and ethanol, as described above, but also from a slurry of odevixibat in a mixture of water and an organic solvent selected from the group consisting of methanol, 2-propanol, acetone, acetonitrile, 1,4-dioxane, DMF and DMSO. Upon drying of the different mixed solvates obtained under these conditions (crystal modification 2), the same crystalline hydrate of odevixibat is obtained, namely crystal modification 1. Crystal modification 1 contains void volumes that are capable of containing up to about 2 moles of water associated with the crystal per mole of odevixibat, depending on the relative humidity. This form is therefore formally a channel hydrate. At about 30% relative humidity, however, crystal modification 1 contains a substantially stoichiometric amount of about 1.5 moles of water per mole of organic compound and is thus a sesquihydrate. The substantially stoichiometric amount of water is considered advantageous, as the water content of the crystals remains substantially constant even with humidity changes within the normal relative humidity range of about 30% to about 70% RH. Indeed, at normal humidities, such as between about 30 and about 70% RH, crystal modification 1 exhibits relatively low hygroscopicity.

In one embodiment, the formulation comprises crystal modification 1 of odevixibat having an X-ray powder diffraction (XRPD) pattern, obtained with CuKα1-radiation, with at least specific peaks at °2θ positions 5.6±0.2, 6.7±0.2 and/or 12.1±0.2.

In a specific embodiment, the formulation comprises crystal modification 1 having an XRPD pattern, obtained with CuKα1-radiation, with specific peaks at °2θ positions 5.6±0.2, 6.7±0.2 and 12.1±0.2 and one or more of the characteristic peaks: 4.1±0.2, 4.6±0.2, 9.3±0.2, 9.4±0.2 and 10.7±0.2.

In a more specific embodiment, the formulation comprises crystal modification 1 having an XRPD pattern, obtained with CuKα1-radiation, with specific peaks at °2θ positions 4.6±0.2, 5.6±0.2, 6.7±0.2, 9.3±0.2, 9.4±0.2 and 12.1±0.2.

In a more specific embodiment, the formulation comprises crystal modification 1 having an XRPD pattern, obtained with CuKα1-radiation, with characteristic peaks at °2θ positions 4.1±0.2, 4.6±0.2, 5.6±0.2, 6.7±0.2, 9.3±0.2, 9.4±0.2, 10.7±0.2 and 12.1±0.2, and one or more of 8.1±0.2, 8.6±0.2, 13.4±0.2, 13.8±0.2, 13.9±0.2, 16.6±0.2, 17.3±0.2, 17.7±0.2, 18.3±0.2, 18.9±0.2, 19.4±0.2, 19.7±0.2, 20.5±0.2, 20.8±0.2, 21.6±0.2, 23.2±0.2, 24.3±0.2, 29.8±0.2 and 30.6±0.2.

In an even more specific embodiment, the formulation comprises crystal modification 1 having an XRPD pattern, obtained with CuKα1-radiation, with characteristic peaks at °2θ positions 4.1±0.2, 4.6±0.2, 5.6±0.2, 6.7±0.2, 8.1±0.2, 8.6±0.2, 9.3±0.2, 9.4±0.2, 10.7±0.2, 12.1±0.2, 13.4±0.2, 13.8±0.2, 13.9±0.2, 16.6±0.2, 17.3±0.2, 17.7±0.2, 18.3±0.2, 18.9±0.2, 19.4±0.2, 19.7±0.2, 20.5±0.2, 20.8±0.2, 21.6±0.2, 23.2±0.2, 24.3±0.2, 29.8±0.2 and 30.6±0.2.

In another embodiment, the formulation comprises crystal modification 1 having an XRPD pattern, obtained with CuKα1-radiation, substantially as shown in FIG. 1.

Whereas crystal modification 1 is a sesquihydrate containing about 3.5% (w/w) water at about 30% relative humidity (based on the total crystal weight), it has been observed that the crystal can take up an additional 1.5% (w/w) water when the humidity is increased up to 95% RH. The sorption and desorption of this additional water is fully reversible. The additional water may be adsorbed on the surface or may further fill the channels of the structure. In some embodiments, the term "overhydrated" refers to crystal modification 1 containing from about 1.5 to about 4 moles of water per mole of odevixibat, such as from about 1.5 to about 3.5, or such as from about 1.5 to 3, or such as from about 1.5 to about 2.5, or such as from about 1.5 to about 2 moles of water per mole of odevixibat. In some embodiments, the term "overhydrated" refers to crystal modification 1 containing from about 2 to about 4 moles of water per mole of odevixibat, such as from about 2 to about 3.5, or such as from about 2 to about 3, or such as from about 2 to 2.5 moles of water per mole of odevixibat.

Figure 3:
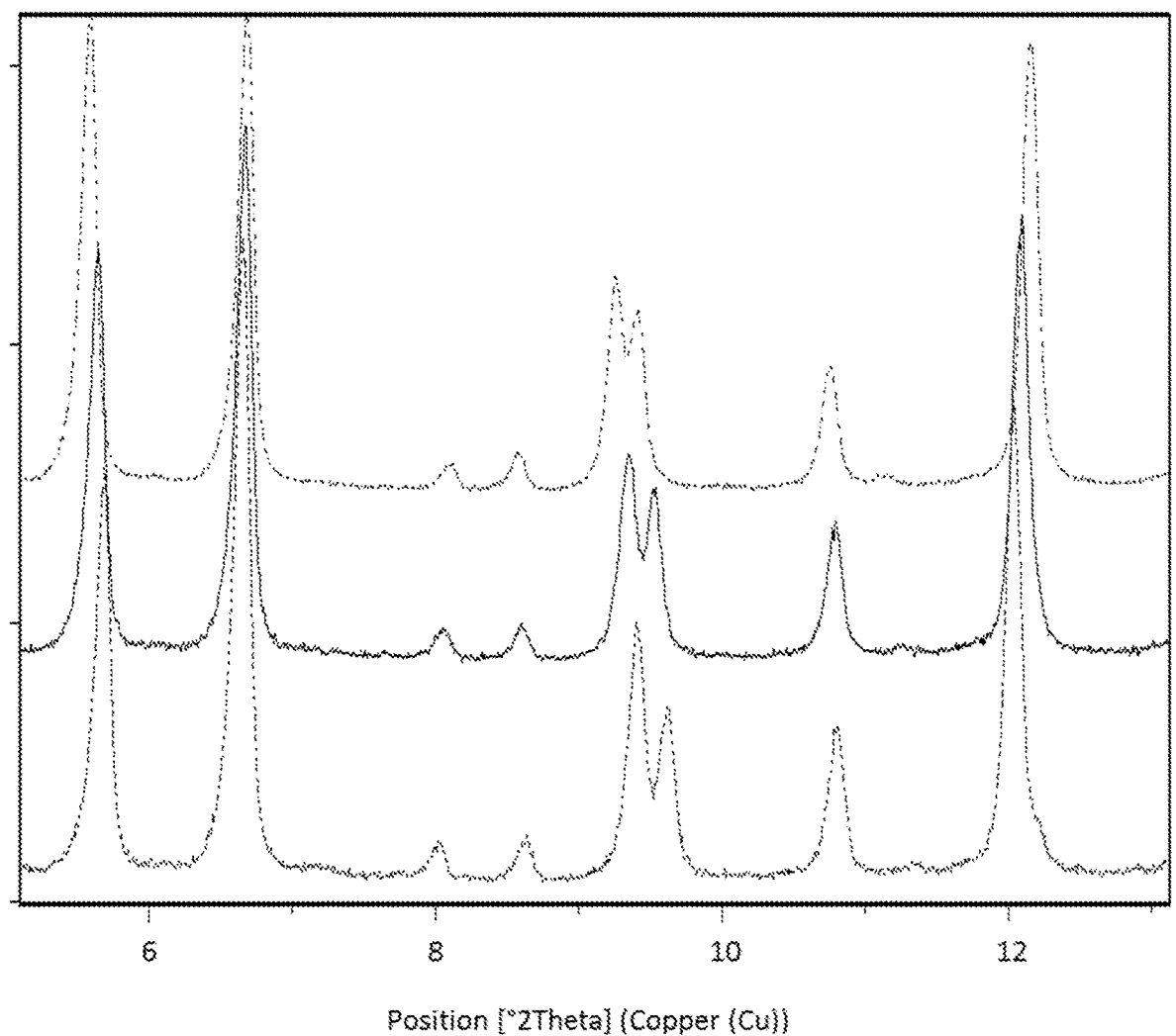
FIG. 3 shows the drying of crystal modification 1, with the X-ray powder diffractogram of an overhydrated sample of crystal modification 1 at the bottom and of a dried sample at the top (2θ range 5-13°).
Figure 4:
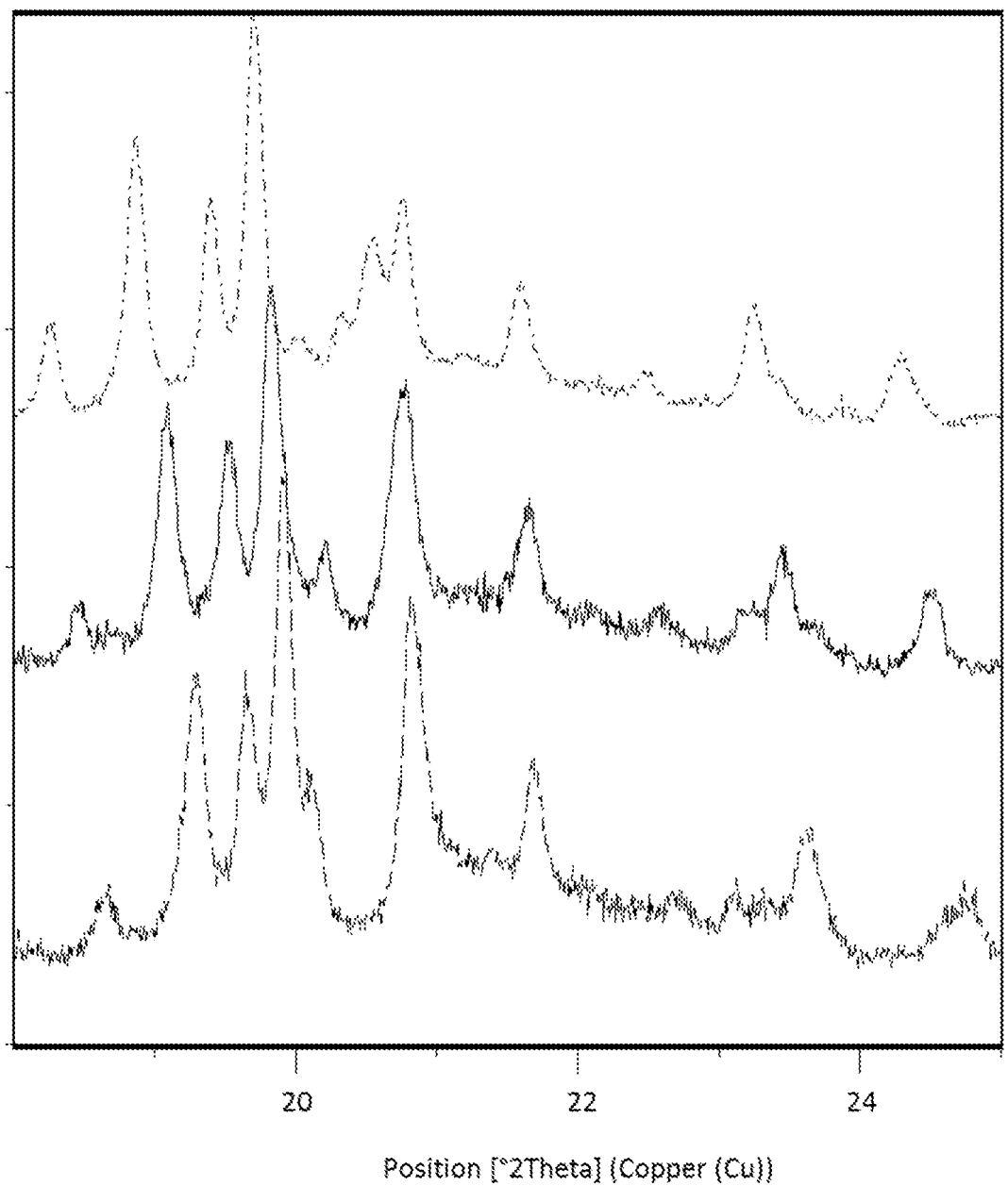
FIG. 4 shows the drying of crystal modification 1, with the X-ray powder diffractogram of an overhydrated sample of crystal modification 1 at the bottom and of a dry sample at the top (2θ range 18-25°).

It has been observed that the XRPD pattern of overhydrated crystal modification 1 slightly changes when it is dried, e.g. at 50° C. in vacuum. A small shift of peaks is most clearly seen in the 2θ ranges 5-13° and 18-25°, as shown in FIGS. 3 and 4, respectively. Exposing the dried modification to elevated relative humidity, such as up to 95% RH, makes the XRPD pattern of the overhydrated modification appear again. The peak shifts are a result of the unit cell volume changes, which occur as water molecules go in and out of the crystal structure.

Therefore, in another embodiment, the formulation comprises overhydrated crystal modification 1 having an X-ray powder diffraction (XRPD) pattern, obtained with CuKα1-radiation, with at least specific peaks at °2θ positions 5.7±0.2, 6.7±0.2 and/or 12.0±0.2.

In a specific embodiment, the formulation comprises overhydrated crystal modification 1 having an XRPD pattern, obtained with CuKα1-radiation, with specific peaks at °2θ positions 5.7±0.2, 6.7±0.2 and 12.0±0.2 and one or more of the characteristic peaks: 4.0±0.2, 9.4±0.2, 9.6±0.2 and 10.8±0.2.

In a more specific embodiment, the formulation comprises overhydrated crystal modification 1 having an XRPD pattern, obtained with CuKα1-radiation, with specific peaks at °2θ positions 4.0±0.2, 5.7±0.2, 6.7±0.2, 9.4±0.2, 9.6±0.2, 10.8±0.2 and 12.1±0.2.

In a more specific embodiment, the formulation comprises overhydrated crystal modification 1 having an XRPD pattern, obtained with CuKα1-radiation, with characteristic peaks at °2θ positions 4.0±0.2, 5.7±0.2, 6.7±0.2, 9.4±0.2, 9.6±0.2, 10.8±0.2 and 12.1±0.2, and one or more of 4.7±0.2, 8.0±0.2, 8.6±0.2, 13.3±0.2, 14.1±0.2, 15.3±0.2, 16.5±0.2, 17.3±0.2, 19.3±0.2, 19.7±0.2, 19.9±0.2, 20.1±0.2, 20.8±0.2, 21.7±0.2, 23.6±0.2, 26.2±0.2, 26.5±0.2, 28.3±0.2 and 30.9±0.2.

In an even more specific embodiment, the formulation comprises overhydrated crystal modification 1 having an XRPD pattern, obtained with CuKα1-radiation, with characteristic peaks at °2θ positions 4.0±0.2, 4.7±0.2, 5.7±0.2, 6.7±0.2, 8.0±0.2, 8.6±0.2, 9.4±0.2, 9.6±0.2, 10.8±0.2, 12.1±0.2, 13.3±0.2, 14.1±0.2, 15.3±0.2, 16.5±0.2, 17.3±0.2, 19.3±0.2, 19.7±0.2, 19.9±0.2, 20.1±0.2, 20.8±0.2, 21.7±0.2, 23.6±0.2, 26.2±0.2, 26.5±0.2, 28.3±0.2 and 30.9±0.2.

Figure 2:
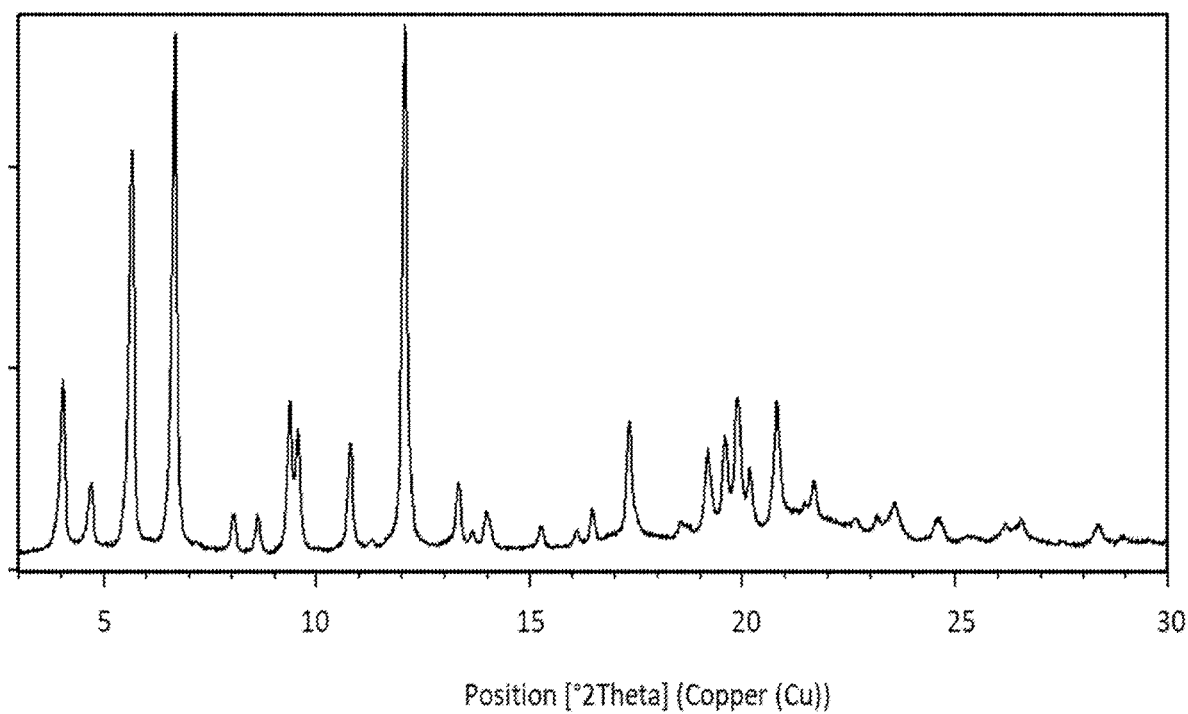
FIG. 2 shows the X-ray powder diffractogram of an overhydrated sample of crystal modification 1.

In another embodiment, the formulation comprises overhydrated crystal modification 1 of odevixibat having an XRPD pattern, obtained with CuKα1-radiation, substantially as shown in FIG. 2.

It is desirable that the use of organic solvents in the preparation of the formulation is avoided. In some embodiments, water is used as the solvent for the preparation of the formulation. Odevixibat dissolves in water only very poorly, and the solubility at pH 7 and at 37° C. has been determined to be as low as about 30 µg/mL. Because of this low solubility in water, aqueous suspensions of odevixibat can contain larger agglomerates of odevixibat, which may lead to an uneven distribution of the active pharmaceutical ingredient on the cores, i.e. the cores may contain different amounts of odevixibat, which in turn impacts dose uniformity. Accordingly, in some embodiments, the aqueous suspension of odevixibat is homogeneous. In some embodiments, a homogeneous aqueous suspension of odevixibat is sprayed onto the cores.

Odevixibat exhibits high potency and it should be administered in low doses, especially in the treatment of pediatric patients that weigh about 5 to 20 kg. In order to reach high dose uniformity for the multiparticulate formulation disclosed herein, it is important that each particle of the formulation substantially contains the same amount of odevixibat, i.e., the deviation in the odevixibat content of the particles of the formulation should be as low as possible.

As used herein, the term "homogeneous" refers to a suspension that does not contain agglomerates of odevixibat that are larger than about 200 µm, and preferably no agglomerates larger than about 100 µm, more preferably no agglomerates larger than about 50 µm. The size of the odevixibat agglomerates in the coating suspension may be determined by optical microscopy, using a method based on European Pharmacopoeia 9.0, monograph 2.9.37, and as described in the experimental section. Alternatively, the size of the odevixibat agglomerates in the coating suspension may be determined by light scattering techniques, such as low-angle laser light scattering (LALLS). In some embodiments, the $d_{90}$ value for the particle size distribution of the coating suspension is smaller than 15 µm, such as smaller than 14 µm, such as smaller than 13 µm, such as smaller than 12 µm, such as smaller than 11 µm, or such as smaller than 10 µm.

In some embodiments, a homogeneous suspension of odevixibat can be prepared by dispersing the compound in water by wet-milling. Wet-milling is a process in which a solid substance is dispersed in a liquid by shearing, by crushing, or by attrition. Examples of wet-milling apparatus include colloid mills, conical mills, ball mills, disc mills and high-shear dispersing machines. A specific example of a wet-milling apparatus for use in the present invention is a colloid mill.

In some embodiments, the crystallinity of odevixibat increases during the wet-milling.

Preferably, odevixibat is first wetted in a small amount of water using a homogenizer and thereafter dispersed in water using a colloid mill. Spraying the homogenized dispersion onto the cores enables an even distribution of the active pharmaceutical ingredient.

It is desirable that the formulation is free of any ingredients that are not strictly necessary for the formulation, such as surfactants. In a preferred embodiment, therefore, the coating suspension does not contain surfactants. Similarly, in some embodiments, the coating layer of the formulation does not contain surfactants.

In one embodiment, the particles are contained within a sachet. In another embodiment, the particles are contained within a capsule. Such capsules may be made from gelatine, from a cellulose-based polymer such as a hydroxypropyl methylcellulose (hypromellose), or from a polysaccharide-based polymer such as a pullulan. Capsules may be swallowed intact, or may be designed to be opened, so that, for example, the contents (i.e. the particles) can be sprinkled onto a food vehicle for administration. In the latter case, the number of particles in one capsule should preferably fit onto a single tablespoon of food. In some embodiments, a capsule contains from about 20 to about 100 mg of particles, such as about 30, about 40, about 50, about 60, about 70, about 80 or about 90 mg.

For younger paediatric patients, such as infants, toddlers and children up to about 6 years old, the particles are preferably sprinkled onto food that can be easily swallowed and which does not require chewing, such as yoghurt, apple sauce, fruit purée or oatmeal. For older paediatric patients, such as children older than about 6 years old, adolescents and younger adults, capsules containing the particles may be swallowed intact, i.e. without opening. For newborn patients up to about 6 months old, who have not yet been weaned or are unable to take semi-solid food, the formulation can be administered by dispersing the particles in a suitable liquid vehicle, such as breast milk, baby formula or water. When the particles have been dispersed in a liquid vehicle, they can be administered to the patient within 30 minutes after dispersion, without loss of the active ingredient or indications of degradation. In some embodiments, the volume of liquid vehicle used for administering the odevixibat particles, including rinsing, can be smaller than about 20 mL, such as smaller than about 15 mL, such as smaller than about 10 mL, or such as smaller than about 5 mL. In some embodiments, the dispersed particles are administered directly into the mouth using an oral syringe.

The formulation disclosed herein may be used in the treatment or prevention of liver diseases, such as bile acid-dependent liver diseases. In some embodiments, a liver disease involves elevated levels of bile acids in the serum and/or in the liver. The formulation disclosed herein may in particular be used in the treatment or prevention of cholestatic liver diseases, including rare paediatric cholestatic liver diseases, such as biliary atresia; post-Kasai biliary atresia; post-liver transplantation biliary atresia; progressive familial intrahepatic cholestasis (PFIC), including PFIC-1, PFIC-2, PFIC-3 and non-specified PFIC, post-biliary diversion PFIC and post-liver transplant PFIC; Alagille syndrome (ALGS); and primary biliary cirrhosis (PBC); as well as paediatric cholestatic pruritus. In one aspect, therefore, the invention relates to the formulation disclosed herein for use in the treatment or prevention of a cholestatic liver disease. In another aspect, the invention relates to a method of treating or preventing a cholestatic liver disease in a subject, such as a human, comprising administering to the subject in need of such treatment or prevention a therapeutically effective amount of the formulation disclosed herein.

Biliary atresia is a rare pediatric liver disease that involves a partial or total blockage (or even absence) of large bile ducts. This blockage or absence causes cholestasis that leads to the accumulation of bile acids that damages the liver. In some embodiments, the accumulation of bile acids occurs in the extrahepatic biliary tree. In some embodiments, the accumulation of bile acids occurs in the intrahepatic biliary tree. The current standard of care is the Kasai procedure, which is a surgery that removes the blocked bile ducts and directly connects a portion of the small intestine to the liver. There are currently no approved drug therapies for this disorder.

Provided herein are methods for treating biliary atresia in a subject in need thereof, the methods comprising administration of a therapeutically effective amount of the formulation disclosed herein. In some embodiments, the subject has undergone the Kasai procedure prior to administration of the formulation disclosed herein. In some embodiments, the subject is administered the formulation disclosed herein prior to undergoing the Kasai procedure. In some embodiments, the treatment of biliary atresia decreases the level of serum bile acids in the subject. In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of the formulation disclosed herein. In some embodiments, the treatment of biliary atresia includes treatment of pruritus.

PFIC is a rare genetic disorder that is estimated to affect between one in every 50,000 to 100,000 children born worldwide and causes progressive, life-threatening liver disease.

One manifestation of PFIC is pruritus, which often results in a severely diminished quality of life. In some cases, PFIC leads to cirrhosis and liver failure. Current therapies include Partial External Biliary Diversion (PEBD) and liver transplantation, however, these options can carry substantial risk of post-surgical complications, as well as psychological and social issues.

Three alternative gene defects have been identified that correlate to three separate PFIC subtypes known as types 1, 2 and 3.

- PFIC, type 1, which is sometimes referred to as "Byler disease," is caused by impaired bile secretion due to mutations in the ATP8B1 gene, which codes for a protein that helps to maintain an appropriate balance of fats known as phospholipids in cell membranes in the bile ducts. An imbalance in these phospholipids is associated with cholestasis and elevated bile acids in the liver. Subjects affected by PFIC, type 1 usually develop cholestasis in the first months of life and, in the absence of surgical treatment, progress to cirrhosis and end-stage liver disease before the end of the first decade of life.
- PFIC, type 2, which is sometimes referred to as "Byler syndrome," is caused by impaired bile salt secretion due to mutations in the ABCB11 gene, which codes for a protein, known as the bile salt export pump, that moves bile acids out of the liver. Subjects with PFIC, type 2 often develop liver failure within the first few years of life and are at increased risk of developing a type of liver cancer known as hepatocellular carcinoma.
- PFIC, type 3, which typically presents in the first years of childhood with progressive cholestasis, is caused by mutations in the ABCB4 gene, which codes for a transporter that moves phospholipids across cell membranes.

In addition, TJP2 gene, NR1H4 gene or Myo5b gene mutations have been proposed to be causes of PFIC. In addition, some subjects with PFIC do not have a mutation in any of the ATP8B1, ABCB11, ABCB4, TJP2, NR1H4 or Myo5b genes. In these cases, the cause of the condition is unknown.

Exemplary mutations of the ATP8B1 gene or the resulting protein are listed in Tables 1 and 2, with numbering based on the human wild type ATP8B1 protein (e.g., SEQ ID NO: 1) or gene (e.g., SEQ ID NO: 2). Exemplary mutations of the ABCB11 gene or the resulting protein are listed in Tables 4 and 5, with numbering based on the human wild type ABCB11 protein (e.g., SEQ ID NO: 3) or gene (e.g., SEQ ID NO: 4).

As can be appreciated by those skilled in the art, an amino acid position in a reference protein sequence that corresponds to a specific amino acid position in SEQ ID NO: 1 or 3 can be determined by aligning the reference protein sequence with SEQ ID NO: 1 or 3 (e.g., using a software program, such as ClustalW2). Changes to these residues (referred to herein as "mutations") may include single or multiple amino acid substitutions, insertions within or flanking the sequences, and deletions within or flanking the sequences. As can be appreciated by those skilled in the art, an nucleotide position in a reference gene sequence that corresponds to a specific nucleotide position in SEQ ID NO: 2 or 4 can be determined by aligning the reference gene sequence with SEQ ID NO: 2 or 4 (e.g., using a software program, such as ClustalW2). Changes to these residues (referred to herein as "mutations") may include single or multiple nucleotide substitutions, insertions within or flanking the sequences, and deletions within or flanking the sequences. See also Kooistra, et al., "KLIFS: A structural kinase-ligand interaction database," Nucleic Acids Res. 2016, vol. 44, no. D1, pp. D365-D371, which is incorporated by reference in its entirety herein.

TABLE 1

Exemplary ATP8B1 Mutations

Amino acid position 3 (e.g., T3K)[27]
Amino acid position 23 (e.g., P23L)[5]
Amino acid position 45 (e.g., N45T)[5,8,9]
Amino acid position 46 (e.g., R46X)[4,25]
Amino acid position 62 (e.g., C62R)[28]
Amino acid position 63 (e.g., T63T)[41]
Amino acid position 70 (e.g., D70N)[1,6]
Amino acid position 71 (e.g., R71H)[43]
Amino acid position 78 (e.g., H78Q)[19]
Amino acid position 82 (e.g., T82T)[41]
Amino acid position 92 (e.g., Y92Y)[41]
Amino acid position 93 (e.g., A93A)[6]
Amino acid position 96 (e.g., A96G)[27]
Amino acid position 114 (e.g., E114Q)[8]
Amino acid position 127 (e.g., L127P[6], L127V[36])
Amino acid position 177 (e.g., T177T)[6]
Amino acid position 179 (e.g., E179X)[29]
Δ Amino acid positions 185-282[44]
Amino acid position 197 (e.g., G197Lfs*10)[22]
Amino acid position 201 (e.g., R201S[27], R201H[35])

TABLE 1-continued

Exemplary ATP8B1 Mutations

Amino acid position 203 (e.g., K203E[5,8], K203R[9], K203fs[25])
Amino acid position 205 (e.g., N205fs[6], N205Kfs*2[35])
Amino acid position 209 (e.g., P209T)[4]
Amino acid position 217 (e.g., S217N)[43]
Amino acid position 232 (e.g., D232D)[30]
Amino acid position 233 (e.g., G233R)[38]
Amino acid position 243 (e.g., L243fs*28)[33]
Amino acid position 265 (e.g., C265R)[25]
Amino acid position 271 (e.g., R271X[13], R271R[30])
Amino acid position 288 (e.g., L288S)[6]
Amino acid position 294 (e.g., L294S)[43]
Amino acid position 296 (e.g., R296C)[11]
Amino acid position 305 (e.g., F305I)[28]
Amino acid position 306 (e.g., C306R)[23]
Amino acid position 307 (e.g., H307L)[35]
Amino acid position 308 (e.g., G308V[1], G308D[6], G308S[35])
Amino acid position 314 (e.g., G314S)[13]
Amino acid position 320 (e.g., M320Vfs*13)[11]
Amino acid position 337 (e.g., M337R)[18]
Amino acid position 338 (e.g., N338K)[18]
Amino acid position 340 (e.g., M340V)[18]
Amino acid position 344 (e.g., I344F)[6,20]
Amino acid position 349 (e.g., I349T)[41]
Amino acid position 358 (e.g., G358R)[28]
Amino acid position 367 (e.g., G367G)[41]
Amino acid position 368 (e.g., N368D)[41]
Amino acid position 393 (e.g., I393V)[27]
Amino acid position 403 (e.g., S403Y)[6]
Amino acid position 407 (e.g., S407N)[40]
Amino acid position 412 (e.g., R412P)[6]
Amino acid position 415 (e.g., Q415R)[27]
Amino acid position 422 (e.g., D422H)[35]
Amino acid position 429 (e.g., E429A)[6]
Amino acid position 446 (e.g., G446R)[4,11]
Amino acid position 453 (e.g., S453Y)[6]
Amino acid position 454 (e.g., D454G)[6]
Amino acid position 455 (e.g., K455N)[43]
Amino acid position 456 (e.g., T456M[3,6], T456K[35])
Amino acid position 457 (e.g., G457G[6], G457fs*6[33])
Amino acid position 469 (e.g., C469G)[41]
Amino acid position 478 (e.g., H478H)[41]
Amino acid position 500 (e.g., Y500H)[6]
Amino acid position 525 (e.g., R525X)[4]
Δ Amino acid position 529[6]
Amino acid position 535 (e.g., H535L[6], H535N[41])
Amino acid position 553 (e.g., P553P)[43]
Amino acid position 554 (e.g., D554N[1,6], D554A[35])
Δ Amino acid positions 556-628[44]
Δ Amino acid positions 559-563[35]
Amino acid position 570 (e.g., L570L)[41]
Amino acid position 577 (e.g., I577V)[19]
Amino acid position 581 (e.g., E581K)[35]
Amino acid positions 554 and 581 (e.g., D554A + E581K)[35]
Amino acid position 585 (e.g., E585X)[21]
Amino acid position 600 (e.g., R600W[2,4], R600Q[6])
Amino acid position 602 (e.g., R602X)[3,6]
Amino acid position 628 (e.g., R628W)[6]
Amino acid position 631 (e.g., R631Q)[28]
Δ Amino acid positions 645-699[4]
Amino acid position 661 (e.g., I661T)[1,4,6]
Amino acid position 665 (e.g., E665X)[4,6]
Amino acid position 672 (e.g., K672fs[6], K672Vfs*1[35])
Amino acid position 674 (e.g., M674T)[19]
Amino acid positions 78 and 674 (e.g., H78Q/M674T)[19]
Amino acid position 684 (e.g., D684D)[41]
Amino acid position 688 (e.g., D688G)[6]
Amino acid position 694 (e.g., I694T[6], I694N[17])
Amino acid position 695 (e.g., E695K)[27]
Amino acid position 709 (e.g., K709fs[6], K709Qfs*41[13])
Amino acid position 717 (e.g., T717N)[4]
Amino acid position 733 (e.g., G733N)[6]
Amino acid position 757 (e.g., Y757X)[4]
Amino acid position 749 (e.g., L749P)[21]
Amino acid position 792 (e.g., P792fs)[6]
Δ Amino acid position 795-797[6]
Amino acid position 809 (e.g., I809L)[27]
Amino acid position 814 (e.g., K814N)[28]
Amino acid position 833 (e.g., R833Q[27], R833W[41])
Amino acid position 835 (e.g., K835Rfs*36)[35]
Amino acid position 845 (e.g., K845fs)[25]
Amino acid position 849 (e.g., R849Q)[24]
Amino acid position 853 (e.g., F853S, F853fs)[6]
Amino acid position 867 (e.g., R867C[1], R867fs[6], R867H[23])
Amino acid position 885 (e.g., K885T)[41]
Amino acid position 888 (e.g., T888T)[41]
Amino acid position 892 (e.g., G892R)[6]
Amino acid position 912 (e.g., G912R)[35]
Amino acid position 921 (e.g., S921S)[41]
Amino acid position 924 (e.g., Y924C)[28]
Amino acid position 930 (e.g., R930X[6], R930Q[28])
Amino acid position 941 (e.g., R941X)[35]
Amino acid position 946 (e.g., R946T)[41]
Amino acid position 952 (e.g., R952Q[5,9,15], R952X[6])
Amino acid position 958 (e.g., N958fs)[6]
Amino acid position 960 (e.g., A960A)[41]
Δ Amino acid position 971[43]
Amino acid position 976 (e.g., A976E[41], A976A[43])
Amino acid position 981 (e.g., E981K)[20]
Amino acid position 994 (e.g., S994R)[4]
Amino acid position 1011 (e.g., L1011fs*18)[33]
Amino acid position 1012 (e.g., S1012I)[10]
Amino acid position 1014 (e.g., R1014X)[6,11]
Amino acid position 1015 (e.g., F1015L)[27]
Amino acid position 1023 (e.g., Q1023fs)[6]
Amino acid position 1040 (e.g., G1040R)[1,6]
Amino acid position 1044 (e.g., S0144L)[34]
Amino acid position 1047 (e.g., L1047fs)[6]
Amino acid position 1050 (e.g., I1050K)[31]
Amino acid position 1052 (e.g., L1052R)[28]
Amino acid position 1095 (e.g., W1095X)[11]
Amino acid position 1098 (e.g., V1098X)[35]
Amino acid position 1131 (e.g., Q1131X)[44]
Amino acid position 1142 (e.g., A1142Tfs*35)[43]
Amino acid position 1144 (e.g., Y1144Y)[43]
Amino acid position 1150 (e.g., I1150T)[41]
Amino acid position 1152 (e.g., A1152T)[30]
Amino acid position 1159 (e.g., P1159P)[25,43]
Amino acid position 1164 (e.g., R1164X)[6]
Amino acid position 1193 (e.g., R1193fs*39)[33]
Amino acid position 1197 (e.g., V1197L)[41]
Amino acid position 1208 (e.g., A1208fs)[6]
Amino acid position 1209 (e.g., Y1209Lfs*28)[4]
Amino acid position 1211 (e.g., F1211L)[27]
Amino acid position 1219 (e.g., D1219H[5], D1219G[27])
Amino acid position 1223 (e.g., S1223S)[41]
Amino acid position 1233 (e.g., P1233P)[41]
Amino acid position 1241 (e.g., G1241fs)[6]
Amino acid position 1248 (e.g., T1248T)[43]
Splice site mutation IVS3 + 1_+3delGTG[6]
Splice site mutation IVS3 − 2A > G[6]
IVS6 + 5T > G[17,25]
Splice site mutation IVS8 + 1G > T[6]
IVS9 − G > A[26]
IVS12 + 1G > A[25]
Splice site mutation IVS17 − 1G > A[6]
Splice site mutation IVS18 + 2T > C[6]
Splice site mutation IVS20 − 4CT > AA
Splice site mutation IVS21 + 5G > A[6]
Splice site mutation IVS23 − 3C > A[6]
Splice site mutation IVS26 + 2T > A[6]
g.24774-42062del[4]
c.−4C > G[41]
c.145C > T[12]
c.181 − 72G > A[9]
c.182 − 5T > A[41]
c.182 − 72G > A[41]
c.246A > G[9]
c.239G > A[39]
c.279 + 1_279 + 3delGTG[46]
c.280 − 2A > G[46]
c.625_62715delinsACAGTAAT[46]
c.554 + 122C > T[9]
c.555 − 3T > C[27]
c.625 + 5 G > T[4]

TABLE 1-continued

Exemplary ATP8B1 Mutations

Amino acid position 209 (e.g., P209T) and c.625 + 5 G > T[4]
c.628 − 30G > A[41]
c.628 − 31C > T[41]
c.698 + 1G > T[46]
c.698 + 20C > T[41]
c.782 − 1G > A[46]
c.782 − 34G > A[41]
Δ795-797[14]
c.782 − 1G > A[4]
c.852A > C[27]
c.941 − 1G > A[46]
c.1014C > T[9]
c.1029 + 35G > A[9]
c.1221 − 8C.G[41]
1226delA[16]
c.1429 + 1G > A[46]
c.1429 + 2T > G[13]
c.1429 + 49G > A[41]
c.1430 − 42A > G[41]
c.1493T > C[12]
c.1587_1589delCTT[46]
c.1630 + 2T > G[27]
c.1631 − 10T > A[41]
c.1637 − 37T > C[41]
1660 G > A[14]
1798 C > T[14]
1799 G > A[14]
c.1819 − 39_41delAA[9]
c.1819 + 1G > A[31]
c.1820 − 27G > A[41]
c.1918 + 8C > T[27]
c.1933 − 1G > A K46
c.2097 + 2T > C[32]
c.2097 + 60T > G[41]
c.2097 + 89T > C[41]
c.2097 + 97T > G[41]
c.2210 − 114T > C[9]
2210delA[16]
c.2210 − 45_50dupATAAAA[9]
c.2285 + 29C · T[41]
c.2285 + 32A > G[41]
c.2286 − 4_2286-3delinsAA[46]
c.2418 + 5G > A[46]
c.2707 + 3G > C[27]
c.2707 + 9T > G[41]
c.2707 + 43A > G[41]
c.2709 − 59T > C[41]
c.2931 + 9A > G[41]
c.2931 + 59T > A[41]
c.2932 − 3C > A[46]
c.2932 + 59T > A[9]
c.2937A > C[27]
c.3016 − 9C > A[31]
c.3033-3034del[19]
3122delTCCTA/insACATCGATGTTGATGTTAGG[45]
3318 G > A[14]
c.3400 + 2T > A[46]
c.3401 − 175C > T[9]
c.3401 − 167C > T[9]
c.3401 − 108C > T[9]
c.3531 + 8G > T[9,15]
c.3532 − 15C > T[9]
Δ Phe ex 15[4]
Ex1_Ex13del[6]
Ex2_Ex6del[33]
Ex12_Ex14del[27]
Skipped Exon 24[45]
del5'UTR-ex18[11]
c.*11C > T[41]
c.*1101 + 366G > A[7]
g.92918del565[31]
GC preceding exon 16 (e.g., resulting in a 4 bp deletion)[42]
Frameshift from the 5' end of exon 16[42]
5' 1.4 kb deletion[46]

TABLE 2

Selected ATP8B1 Mutations Associated with PFIC-1

Amino acid position 23 (e.g., P23L)[5]
Amino acid position 78 (e.g., H78Q)[19]
Amino acid position 93 (e.g., A93A)[6]
Amino acid position 96 (e.g., A96G)[27]
Amino acid position 127 (e.g., L127P)[6]
Amino acid position 197 (e.g., G197Lfs*10)[22]
Amino acid position 205 (e.g., N205fs)[6]
Amino acid position 209 (e.g., P209T)[4]
Amino acid position 233 (e.g., G233R)[38]
Amino acid position 243 (e.g., L243fs*28)[33]
Amino acid position 288 (e.g., L288S)[6]
Amino acid position 296 (e.g., R296C)[11]
Amino acid position 308 (e.g., G308V)[1,6]
Amino acid position 320 (e.g., M320Vfs*13)[11]
Amino acid position 403 (e.g., S403Y)[6]
Amino acid position 407 (e.g., S407N)[40]
Amino acid position 412 (e.g., R412P)[6]
Amino acid position 415 (e.g., Q415R)[27]
Amino acid position 429 (e.g., E429A)[6]
Amino acid position 446 (e.g., G446R)[4]
Amino acid position 456 (e.g., T456M)[3,6]
Amino acid position 457 (e.g., G457G[6], G457fs*6[33])
Amino acid position 500 (e.g., Y500H)[6]
Amino acid position 525 (e.g., R525X)[4]
Δ Amino acid position 529[6]
Amino acid position 535 (e.g., H535L)[6]
Amino acid position 554 (e.g., D554N)[1,6]
Amino acid position 577 (e.g., I577V)[19]
Amino acid position 585 (e.g., E585X)[21]
Amino acid position 600 (e.g., R600W)[4]
Amino acid position 602 (e.g., R602X)[3,6]
Amino acid position 661 (e.g., I661T)[4,6]
Amino acid position 665 (e.g., E665X)[4,6]
Δ Amino acid positions 645-699[4]
Amino acid position 672 (e.g., K672fs)[6]
Amino acid position 674 (e.g., M674T)[19]
Amino acid positions 78 and 674 (e.g., H78Q/M674T)[19]
Amino acid position 688 (e.g., D688G)[6]
Amino acid position 694 (e.g., I694N)[17]
Amino acid position 695 (e.g., E695K)[27]
Amino acid position 709 (e.g., K709fs)[6]
Amino acid position 717 (e.g., T717N)[4]
Amino acid position 733 (e.g., G733R)[6]
Amino acid position 749 (e.g., L749P)[21]
Amino acid position 757 (e.g., Y757X)[4]
Amino acid position 792 (e.g., P792fs)[6]
Amino acid position 809 (e.g., I809L)[27]
Amino acid position 853 (e.g., F853S, F853fs)[6]
Amino acid position 867 (e.g., R867fs)[6]
Amino acid position 892 (e.g., G892R)[6]
Amino acid position 930 (e.g., R930X[6], R952Q[15])
Amino acid position 952 (e.g., R952X)[6]
Amino acid position 958 (e.g., N958fs)[6]
Amino acid position 981 (e.g., E981K)[20]
Amino acid position 994 (e.g., S994R)[4]
Amino acid position 1014 (e.g., R1014X)[6,11]
Amino acid position 1015 (e.g., F1015L)[27]
Amino acid position 1023 (e.g., Q1023fs)[6]
Amino acid position 1040 (e.g., G1040R)[1,6]
Amino acid position 1047 (e.g., L1047fs)[6]
Amino acid position 1095 (e.g., W1095X)[11]
Amino acid position 1208 (e.g., A1208fs)[6]
Amino acid position 1209 (e.g., Y1209Lfs*28)[4]
Amino acid position 1211 (e.g., F1211L)[27]
Amino acid position 1219 (e.g., D1219H[5], D1219G[27])
Splice site mutation IVS3 + 1_+3delGTG[6]
Splice site mutation IVS3 − 2A > G[6]
IVS6 + 5T > G[17]
Splice site mutation IVS8 + 1G > T[6]
IVS9 − G > A[26]
Splice site mutation IVS17 − 1G > A[6]
Splice site mutation IVS18 + 2T > C[6]
Splice site mutation IVS21 + 5G > A[6]
g.24774-42062del[4]
c.145C > T[12]
c.239G > A[39]
c.625 + 5 G > T[4]

TABLE 2-continued

Selected ATP8B1 Mutations Associated with PFIC-1

Amino acid position 209 (e.g., P209T) and c.625 + 5 G > T[4]
c.782 − 1G > A[4]
c.1493T > C[12]
c.1630 + 2T > G[27]
1660 G > A[14]
c.2707 + 3G > C[27]
c.2097 + 2T > C[32]
c.3033-3034del[19]
3318 G > A[14]
c.3158 + 8G > T[15]
Δ Phe ex 15[4]
Ex1_Ex13del[6]
Ex2_Ex6del[33]
Ex12_Ex14del[27]
del5'UTR-ex18[11]
c.*1101 + 366G > A[7]
GC preceding exon 16 (e.g., resulting in a 4 bp deletion)[42]
Frameshift from the 5' end of exon 16[42]

[4] A mutation to 'X' denotes an early stop codon

References for Tables 1 and 2

[1] Folmer et al., Hepatology. 2009, vol. 50(5), p. 1597-1605.
[2] Hsu et al., Hepatol Res. 2009, vol. 39(6), p. 625-631.
[3] Alvarez et al., Hum Mol Genet. 2004, vol. 13(20), p. 2451-2460.
[4] Davit-Spraul et al., Hepatology 2010, vol. 51(5), p. 1645-1655.
[5] Vitale et al., J Gastroenterol. 2018, vol. 53(8), p. 945-958.
[6] Klomp et al., Hepatology 2004, vol. 40(1), p. 27-38.
[7] Zarenezhad et al., Hepatitis Monthly: 2017, vol. 17(2); e43500.
[8] Dixon et al., Scientific Reports 2017, vol. 7, 11823.
[9] Painter et al., Eur J Hum Genet. 2005, vol. 13(4), p. 435-439.
[10] Deng et al., World J Gastroenterol. 2012, vol. 18(44), p. 6504-6509.
[11] Giovannoni et al., PLoS One. 2015, vol. 10(12): e0145021.
[12] Li et al., Hepatology International 2017, vol. 11, No. 1, Supp. Supplement 1, pp. S180. Abstract Number: OP284.
[13] Togawa et al., Journal of Pediatric Gastroenterology and Nutrition 2018, vol. 67, Supp. Supplement 1, pp. S363. Abstract Number: 615.
[14] Miloh et al., Gastroenterology 2006, vol. 130, No. 4, Suppl. 2, pp. A759-A760. Meeting Info.: Digestive Disease Week Meeting/107th Annual Meeting of the American-Gastroenterological-Association. Los Angeles, Calif., USA. May 19.
[15] Dröge et al., Zeitschrift fur Gastroenterologie 2015, vol. 53, No. 12. Abstract Number: A3-27. Meeting Info: 32. Jahrestagung der Deutschen Arbeitsgemeinschaft zum Studium der Leber. Dusseldorf, Germany. 22 Jan. 2016- 23 Jan. 2016
[16] Mizuochi et al., Clin Chim Acta. 2012, vol. 413(15-16), p. 1301-1304.
[17] Liu et al., Hepatology International 2009, vol. 3, No. 1, p. 184-185. Abstract Number: PE405. Meeting Info: 19th Conference of the Asian Pacific Association for the Study of the Liver. Hong Kong, China. 13 Feb. 2009-16 Feb. 2009
[18] McKay et al., Version 2. F1000Res. 2013; 2: 32. DOI: 10.12688/f1000research.2-32.v2
[19] Hasegawa et al., Orphanet J Rare Dis. 2014, vol. 9:89.
[20] Stone et al., J Biol Chem. 2012, vol. 287(49), p. 41139-51.
[21] Kang et al., J Pathol Transl Med. 2019 May 16. doi: 10.4132/jptm.2019.05.03. [Epub ahead of print]
[22] Sharma et al., BMC Gastroenterol. 2018, vol. 18(1), p. 107.
[23] Uegaki et al., Intern Med. 2008, vol. 47(7), p. 599-602.
[24] Goldschmidt et al., Hepatol Res. 2016, vol. 46(4), p. 306-311.
[25] Liu et al., J Pediatr Gastroenterol Nutr. 2010, vol. 50(2), p. 179-183.
[26] Jung et al., J Pediatr Gastroenterol Nutr. 2007, vol. 44(4), p. 453-458.
[27] Bounford. University of Birmingham. Dissertation Abstracts International, (2016) Vol. 75, No. 1C. Order No.: AA110588329. ProQuest Dissertations & Theses.
[28] Stolz et al., Aliment Pharmacol Ther. 2019, vol. 49(9), p. 1195-1204.
[29] Ivashkin et al., Hepatology International 2016, vol. 10, No. 1, Supp. SUPPL. 1, pp. S461. Abstract Number: LBO-38. Meeting Info: 25th Annual Conference of the Asian Pacific Association for the Study of the Liver, APASL 2016. Tokyo, Japan. 20 Feb. 2016-24 Feb. 2016
[30] Blackmore et al., J Clin Exp Hepatol. 2013, vol. 3(2), p. 159-161.
[31] Matte et al., J Pediatr Gastroenterol Nutr. 2010, vol. 51(4), p. 488-493.
[32] Squires et al., J Pediatr Gastroenterol Nutr. 2017, vol. 64(3), p. 425-430.
[33] Hayshi et al., EBioMedicine. 2018, vol. 27, p. 187-199.
[34] Nagasaka et al., J Pediatr Gastroenterol Nutr. 2007, vol. 45(1), p. 96-105.
[35] Wang et al., PLoS One. 2016; vol. 11(4): e0153114.
[36] Narchi et al., Saudi J Gastroenterol. 2017, vol. 23(5), p. 303-305.
[37] Alashkar et al., Blood 2015, vol. 126, No. 23. Meeting Info.: 57th Annual Meeting of the American-Society-of-Hematology. Orlando, Fla., USA. Dec. 5-8, 2015. Amer Soc Hematol.
[38] Ferreira et al., Pediatric Transplantation 2013, vol. 17, Supp. SUPPL. 1, pp. 99. Abstract Number: 239. Meeting Info: IPTA 7th Congress on Pediatric Transplantation. Warsaw, Poland. 13 Jul. 2013-16 Jul. 2013.
[39] Pauli-Magnus et al., J Hepatol. 2005, vol. 43(2), p. 342-357.
[40] Jericho et al., Journal of Pediatric Gastroenterology and Nutrition 2015, vol. 60(3), p. 368-374.
[41] van der Woerd et al., PLoS One. 2013, vol. 8(11): e80553.
[42] Copeland et al., J Gastroenterol Hepatol. 2013, vol. 28(3), p. 560-564.
[43] Dröge et al., J Hepatol. 2017, vol. 67(6), p. 1253-1264.
[44] Chen et al., Journal of Pediatrics 2002, vol. 140(1), p. 119-124.
[45] Jirsa et al., Hepatol Res. 2004, vol. 30(1), p. 1-3.
[46] van der Woerd et al., Hepatology 2015, vol. 61(4), p. 1382-1391.

In some embodiments, the mutation in ATP8B1 is selected from L127P, G308V, T456M, D554N, F529del, I661T, E665X, R930X, R952X, R1014X, and G1040R.

TABLE 3

Exemplary ABCB11 Mutations

Amino acid position 1 (e.g., M1V)[9]
Amino acid position 4 (e.g., S4X)[4,64]
Amino acid position 8 (e.g., R8X)[88]
Amino acid position 19 (e.g., G19R)[56]
Amino acid position 24 (e.g., K24X)[35]

TABLE 3-continued

Exemplary ABCB11 Mutations

Amino acid position 25 (e.g., S25X)[5,14]
Amino acid position 26 (e.g., Y26Ifs*7)[38]
Amino acid position 36 (e.g., D36D)[27]
Amino acid position 38 (e.g., K38Rfs*24)[73]
Amino acid position 43 (e.g., V43I)[57]
Amino acid position 49 (e.g., Q49X)[73]
Amino acid position 50 (e.g., L50S, L50W)[57]
Amino acid position 52 (e.g., R52W[26], R52R[28])
Amino acid position 56 (e.g., S56L)[58]
Amino acid position 58 (e.g., D58N)[62]
Amino acid position 62 (e.g., M62K)[9]
Amino acid position 66 (e.g., S66N)[17]
Amino acid position 68 (e.g., C68Y)[41]
Amino acid position 50 (e.g., L50S)[5,7]
Amino acid position 71 (e.g., L71H)[73]
Amino acid position 74 (e.g., I74R)[71]
Amino acid position 77 (e.g., P77A)[73]
Amino acid position 87 (e.g., T87R)[67]
Amino acid position 90 (e.g., F90F)[7,27]
Amino acid position 93 (e.g., Y93S[13], Y93X[88])
Amino acid position 96 (e.g., E96X)[88]
Amino acid position 97 (e.g., L97X)[39]
Amino acid position 101 (e.g., Q101Dfs*8)[9]
Amino acid position 107 (e.g., C107R)[36]
Amino acid position 112 (e.g., I112T)[9]
Amino acid position 114 (e.g., W114R)[2,9]
Amino acid position 123 (e.g., M123T)[67]
Amino acid position 127 (e.g., T127Hfs*6)[5]
Amino acid position 129 (e.g., C129Y)[25]
Amino acid position 130 (e.g., G130G)[77]
Amino acid position 134 (e.g., I134I)[28]
Amino acid position 135 (e.g., E135K[7,13], E135L[17])
Amino acid position 137 (e.g., E137K)[7]
Amino acid position 157 (e.g., Y157C)[5]
Amino acid position 161 (e.g., C161X)[39]
Amino acid position 164 (e.g., V164Gfs*7[30], V164I[85])
Amino acid position 167 (e.g., A167S[4], A167V[7], A167T[9,17])
Amino acid position 181 (e.g., R181I)[35]
Amino acid position 182 (e.g., I182K)[9]
Amino acid position 183 (e.g., M183V[8], M183T[9])
Amino acid position 185 (e.g., M185I)[73]
Amino acid position 186 (e.g., E186G)[2,7,22]
Amino acid position 188 (e.g., G188W)[73]
Amino acid position 194 (e.g., S194P)[7]
Amino acid position 198 (e.g., L198P)[7]
Amino acid position 199 (e.g., N199Ifs*15X)[88]
Amino acid position 206 (e.g., I206V)[28]
Amino acid position 212 (e.g., A212T)[73]
Amino acid position 217 (e.g., M217R)[88]
Amino acid position 225 (e.g., T225P)[57]
Amino acid position 226 (e.g., S226L)[9]
Amino acid position 232 (e.g., L232Cfs*9)[9]
Amino acid position 233 (e.g., L233S)[86]
Amino acid position 238 (e.g., G238V)[2,7]
Amino acid position 242 (e.g., T242I)[5,7]
Amino acid position 245 (e.g., I245Tfs*26)[57]
Amino acid position 256 (e.g., A256G)[9]
Amino acid position 260 (e.g., G260D)[7]
Amino acid position 269 (e.g., Y269Y)[27]
Amino acid position 277 (e.g., A277E)[77]
Amino acid position 283 (e.g., E283D)[73]
Amino acid positions 212 and 283 (e.g., A212T + E283D)[73]
Amino acid position 284 (e.g., V284L[7,39], V284A[7], V284D[23])
Amino acid position 297 (e.g., E297G[1,2,5,7], E297K[7])
Amino acid position 299 (e.g., R299K)[28]
Amino acid position 303 (e.g., R303K[8], R303M[63] R303fsX321[83])
Amino acid position 304 (e.g., Y304X)[26]
Amino acid position 312 (e.g., Q312H)[7]
Amino acid position 313 (e.g., R313S)[5,7]
Amino acid position 314 (e.g., W314X)[57]
Amino acid position 318 (e.g., K318Rfs*26)[29]
Amino acid position 319 (e.g., G319G)[7]
Amino acid position 327 (e.g., G327E)[5,7]
Amino acid position 330 (e.g., W330X)[24]
Amino acid position 336 (e.g., C336S)[2,7]
Amino acid position 337 (e.g., Y337H)[21,27]
Amino acid position 342 (e.g., W342G)[50]
Amino acid position 354 (e.g., R354X)[9]
Amino acid position 361 (e.g., Q361X[57], Q361R[74])
Amino acid position 366 (e.g., V366V[28], V366D[57])
Amino acid position 368 (e.g., V368Rfs*27)[5]
Amino acid position 374 (e.g., G374S)[3]
Amino acid position 380 (e.g., L380Wfs*18)[5]
Amino acid position 382 (e.g., A382G)[88]
Δ Amino acid positions 382-388[5]
Δ Amino acid positions 383-389[57]
Amino acid position 387 (e.g., R387H)[9]
Amino acid position 390 (e.g., A390P)[5,7]
Amino acid position 395 (e.g., E395E)[28]
Amino acid position 404 (e.g., D404G)[9]
Amino acid position 410 (e.g., G410D)[5,7]
Amino acid position 413 (e.g., L413W)[5,7]
Amino acid position 415 (e.g., R415X)[42]
Amino acid position 416 (e.g., I416I)[27]
Amino acid position 420 (e.g., I420T)[9]
Amino acid position 423 (e.g., H423R)[13]
Amino acid position 432 (e.g., R432T)[1,2,7]
Amino acid position 436 (e.g., K436N)[40]
Amino acid position 440 (e.g., D440E)[88]
Amino acid position 444 (e.g., V444A)[2]
Amino acid position 454 (e.g., V454X)[49]
Amino acid position 455 (e.g., G455E)[9]
Amino acid position 457 (e.g., S457Vfs*23)[88]
Amino acid position 461 (e.g., K461E)[2,7]
Amino acid position 462 (e.g., S462R)[88]
Amino acid position 463 (e.g., T463I)[5,7]
Amino acid position 466 (e.g., Q466K)[5,7]
Amino acid position 470 (e.g., R470Q[5,7], R470X[9])
Amino acid position 471 (e.g., Y472X)[5]
Amino acid position 472 (e.g., Y472C[5,27], Y472X[14])
Amino acid position 473 (e.g., D473Q[35], D473V[88])
Amino acid position 475 (e.g., C475X)[29]
Amino acid position 481 (e.g., V481E)[5,7]
Amino acid position 482 (e.g., D482G)[2,5,7]
Amino acid position 484 (e.g., H484Rfs*5)[9]
Amino acid position 487 (e.g., R487H[2], R487P[5])
Amino acid position 490 (e.g., N490D)[5,7]
Amino acid position 493 (e.g., W493X)[8]
Amino acid positon 496 (e.g., D496V)[88]
Amino acid position 498 (e.g., I498T)[2,7]
Amino acid position 499 (e.g., G499E)[73]
Amino acid position 501 (e.g., V501G)[68]
Amino acid position 504 (e.g., E504K)[79]
Amino acid position 510 (e.g., T510T)[7]
Amino acid position 512 (e.g., I512T)[5,7]
Amino acid position 515 (e.g., N515T[5,7], N515D[64])
Amino acid position 516 (e.g., I516M)[17]
Amino acid position 517 (e.g., R517H)[5,7]
Amino acid position 520 (e.g., R520X)[5]
Amino acid position 523 (e.g., A523G)[13]
Amino acid position 528 (e.g., I528Sfs*21[5], I528X[9], I528T[73])
Amino acid position 535 (e.g., A535A[7], A535X[89])
Amino acid position 540 (e.g., F540L)[46]
Amino acid position 541 (e.g., I541L[5,7], I541T[5,17])
Amino acid position 546 (e.g., Q546K[39], Q546H[73])
Amino acid position 548 (e.g., F548Y)[5,7]
Amino acid position 549 (e.g., D549V)[9]
Amino acid position 554 (e.g., E554K)[21]
Amino acid position 556 (e.g., G556R)[67]
Amino acid position 558 (e.g., Q558H)[23]
Amino acid position 559 (e.g., M559T)[57]
Amino acid position 562 (e.g., G562D[5,7], G562S[73])
Amino acid position 570 (e.g., A570T[2,5,7], A570V[26])
Amino acid position 575 (e.g., R575X[2,5], R575Q[21])
Amino acid position 580 (e.g., L580P)[57]
Amino acid position 586 (e.g., T586I)[7]
Amino acid position 587 (e.g., S587X)[73]
Amino acid position 588 (e.g., A588V[5,7], A588P[73])
Amino acid position 591 (e.g., N591S)[2,7]
Amino acid position 593 (e.g., S593R)[2,7]
Amino acid position 597 (e.g., V597V[9], V597L[13])
Amino acid position 603 (e.g., K603K)[55]
Amino acid position 609 (e.g., H609Hfs*46)[26]
Amino acid position 610 (e.g., I610Gfs*45[9], I610T[57])[9]
Amino acid position 615 (e.g., H615R)[26]
Amino acid position 616 (e.g., R616G[28], R616H[73])

TABLE 3-continued

Exemplary ABCB11 Mutations

Amino acid position 619 (e.g., T619A)[28]
Amino acid position 623 (e.g., A623A)[28]
Amino acid position 625 (e.g., T625Nfs*5)[26]
Amino acid position 627 (e.g., I627T)[7]
Amino acid position 628 (e.g., G628Wfs*3)[70]
Amino acid position 636 (e.g., E636G)[2]
Amino acid position 648 (e.g., G648Vfs*6[5], G648V[50])
Amino acid position 655 (e.g., T655I)[7]
Amino acid position 669 (e.g., I669V)[26]
Amino acid position 676 (e.g., D676Y)[11]
Amino acid position 677 (e.g., M677V)[7,13]
Amino acid position 679 (e.g., A679V)[58]
Amino acid position 685 (e.g., G685W)[60]
Amino acid position 696 (e.g., R696W[27], R696Q[58])
Amino acid position 698 (e.g., R698H[7,9], R698K[61], R698C[88])
Amino acid position 699 (e.g., S699P)[9]
Amino acid position 701 (e.g., S701P)[58]
Amino acid position 702 (e.g., Q702X)[89]
Amino acid position 709 (e.g., E709K)[7]
Amino acid position 710 (e.g., P710P)[7]
Amino acid position 712 (e.g., L712L)[28]
Amino acid position 721 (e.g., Y721C)[88]
Amino acid position 729 (e.g., D724N)[39]
Amino acid position 731 (e.g., P731S)[23]
Amino acid position 740 (e.g., P740Qfs*6)[73]
Amino acid position 758 (e.g., G758R)[5]
Amino acid position 766 (e.g., G766R)[5,24]
Amino acid position 772 (e.g., Y772X)[5]
Amino acid position 804 (e.g., A804A)[7]
Amino acid position 806 (e.g., G806D[44], G806G[55])
Amino acid position 809 (e.g., S809F)[81]
Amino acid position 817 (e.g., G817G)[88]
Amino acid position 818 (e.g., Y818F)[7]
Amino acid position 824 (e.g., G824E)[42]
Amino acid position 825 (e.g., G825G)[73]
Amino acid position 830 (e.g., R830Gfs*28)[73]
Amino acid position 832 (e.g., R832C[7,26], R832H[41])
Amino acid position 842 (e.g., D842G)[2]
Amino acid position 848 (e.g., D848N)[73]
Amino acid position 855 (e.g., G855R)[11]
Amino acid position 859 (e.g., T859R)[5,7]
Amino acid position 865 (e.g., A865V)[27]
Amino acid position 866 (e.g., S866A)[57]
Amino acid position 868 (e.g., V868D)[73]
Amino acid position 869 (e.g., Q869P)[73]
Amino acid position 875 (e.g., Q875X)[73]
Amino acid position 877 (e.g., G877R)[56]
Amino acid position 879 (e.g., I879R)[88]
Amino acid position 893 (e.g., A893V)[57]
Amino acid position 901 (e.g., S901R[17], S901I[73])
Amino acid position 903 (e.g., V903G)[57]
Δ Amino acid position 919[12]
Amino acid position 923 (e.g., T923P)[2,7]
Amino acid position 926 (e.g., A926P)[2,7]
Amino acid position 928 (e.g., R928X[15], R928Q[40])
Amino acid position 930 (e.g., K930X[5], K930Efs*79[5,10], K930Efs*49[26])
Amino acid position 931 (e.g., Q931P)[27]
Amino acid position 945 (e.g., S945N)[57]
Amino acid position 948 (e.g., R948C)[5,7,26]
Amino acid position 958 (e.g., R958Q)[28]
Amino acid position 969 (e.g., K969R)[88]
Δ Amino acid positions 969-972[5]
Amino acid position 973 (e.g., T973I)[57]
Amino acid position 976 (e.g., Q976R[58], Q976X[88])
Amino acid position 979 (e.g., N979D)[5,7]
Amino acid position 981 (e.g., Y981Y)[28]
Amino acid position 982 (e.g., G982R)[2,5,7]
Amino acid positions 444 and 982 (e.g., V444A + G982R)[38]
Amino acid position 995 (e.g., A995A)[28]
Amino acid position 1001 (e.g., R1001R)[9]
Amino acid position 1003 (e.g., G1003R)[24]
Amino acid position 1004 (e.g., G1004D)[2,7]
Amino acid position 1027 (e.g., S1027R)[26]
Amino acid position 1028 (e.g., A1028A[7,10,88], A1028E[88])
Amino acid position 1029 (e.g., T1029K)[5]
Amino acid position 1032 (e.g., G1032R)[12]
Amino acid position 1041 (e.g., Y1041X)[9]
Amino acid position 1044 (e.g., A1044P)[88]
Amino acid position 1050 (e.g., R1050C)[2,7,57]
Amino acid position 1053 (e.g., Q1053X)[57]
Amino acid position 1055 (e.g., L1055P)[36]
Amino acid position 1057 (e.g., R1057X[2], R1057Q[58])
Amino acid position 1058 (e.g., Q1058Hfs*38[9], Q1058fs*38[17], Q1058X[73])
Amino acid position 1061 (e.g., I1061Vfs*34)[9]
Amino acid position 1083 (e.g., C1083Y)[47]
Amino acid position 1086 (e.g., T1086T)[28]
Amino acid position 1090 (e.g., R1090X)[2,5]
Amino acid position 1099 (e.g., L1099Lfs*38)[26]
Amino acid position 1100 (e.g., S1100Qfs*38)[13]
Amino acid position 1110 (e.g., A1110E)[5,7]
Amino acid position 1112 (e.g., V1112F)[70]
Amino acid position 1116 (e.g., G1116R[7], G1116F[9,17], G1116E[36])
Amino acid position 1120 (e.g., S1120N)[88]
Amino acid position 1128 (e.g., R1128H[2,7], R1128C[5,7,13])
Amino acid position 1131 (e.g., D1131V)[27]
Amino acid position 1144 (e.g., S1144R)[7]
Amino acid position 1147 (e.g., V1147X)[5]
Amino acid position 1153 (e.g., R1153C[2,5,7], R1153H[5])
Amino acid position 1154 (e.g., S1154P)[5,7]
Amino acid position 1162 (e.g., E1162X)[39]
Δ Amino acid position 1165[88]
Amino acid position 1164 (e.g., V1164Gfs*7)
Amino acid position 1173 (e.g., N1173D)[57]
Amino acid position 1175 (e.g., K1175T)[58]
Amino acid position 1186 (e.g., E1186K)[7]
Amino acid position 1192 (e.g., A1192Efs*50)[9]
Amino acid position 1196 (e.g., Q1196X)[88]
Amino acid position 1197 (e.g., L1197G)[7]
Amino acid position 1198 (e.g., H1198R)[27]
Amino acid position 1204 (e.g., L1204P)[88]
Amino acid position 1208 (e.g. Y1208C)[73]
Amino acid position 1210 (e.g., T1210P[5,7], T1210F[57])
Amino acid position 1211 (e.g., N1211D)[7]
Amino acid position 1212 (e.g., V1212F)[36]
Amino acid position 1215 (e.g., Q1215X)[5]
Amino acid position 1221 (e.g., R1221K)[53]
Amino acid position 1223 (e.g., E1223D)[7]
Amino acid position 1226 (e.g., R1226P)[73]
Amino acid position 1228 (e.g., A1228V)[7]
Amino acid position 1231 (e.g., R1231W[5,7], R1231Q[5,7])
Amino acid position 1232 (e.g., A1232D)[17]
Amino acid position 1235 (e.g., R1235X)[5,12]
Amino acid position 1242 (e.g., L1242I)[5,7]
Amino acid position 1243 (e.g., D1243G)[67]
Amino acid position 1249 (e.g., L1249X)[73]
Amino acid position 1256 (e.g., T1256fs*1296)[83]
Amino acid position 1268 (e.g., R1268Q)[2,7]
Amino acid position 1276 (e.g., R1276H)[30]
Amino acid position 1283 (e.g., A1283A[28], A1283V[88])
Amino acid position 1292 (e.g., G1292V)[73]
Amino acid position 1298 (e.g., G1298R)[5]
Amino acid position 1302 (e.g., E1302X)[5]
Amino acid position 1311 (e.g., Y1311X)[57]
Amino acid position 1316 (e.g., T1316Lfs*64)[15]
Amino acid position 1321 (e.g., S1321N)[57]
Intron 4 ((+3)A > C)[1]
IVS4 − 74A > T[89]
Splice site mutation 3′ Intron 5 c.3901G > A[5]
Splice site mutation 5; Intron 7 c.6111G > A[5]
Splice site mutation IVS7 + 1G > A[14]
IVS7 + 5G > A[40]
IVS8 + 1G > C[76]
Splice site mutation 5′ Intron 9 c.9081delG[5]
Splice site mutation 5′ Intron 9 c.9081G > T[5]
Splice site mutation 5′ Intron 9 c.9081G > A[5]
Splice site mutation IVS9 + 1G > T[14]
Splice site mutation 3′ Intron 13 c.143513_1435 − 8del[5]
Splice site mutation IVS13del − 13^−8[14]
Splice site mutation 3′ Intron 16 c.20128T > G[5]
Splice site mutation IVS16 − 8T > G[14]
Splice site mutation 5′ Intron 18 c.21781G > T[5]
Splice site mutation 5′ Intron 18 c.21781G > A[5]
Splice site mutation 5′ Intron 18 c.21781G > C[5]
Splice site mutation 3′ Intron 18 c.21792A > G[5]
Splice site mutation IVS18 + 1G > A[14]

TABLE 3-continued

Exemplary ABCB11 Mutations

Splice site mutation 5' Intron 19 c.2343 + 1G > T[5]
Splice site mutation 5' Intron 19 c.2343 + 2T > C[5]
Splice site mutation IVS19 + 2T > C[14]
Splice site mutation IVS19 + 1G > A[22]
Splice site mutation 3' Intron 21 c.26112A > T[5]
IVS22 + 3A > G[89]
IVS 23 − 8 G − A[36]
IVS24 + 5G > A[51]
Splice site mutation 5' Intron 24 c.32131delG[5]
IVS35 − 6C > G[89]
Putative splice mutation 1198 − 1G > C[17]
Putative splice mutation 1810 − 3C > G[17]
Putative splice mutation 2178 + 1G > A[17]
Putative splice mutation 2344 − 1G > T[17]
Putative splice mutation 2611 − 2A > T[39]
Putative splice mutation 3213 + 1_3213 + 2delinsA[17]
c.−24C > A[44,78]
c.76 13 G > T[9]
c.77 − 19T > A[52]
c.90_93delGAAA[18]
c.124G > A[69]
c.150 + 3 A > C[10]
174C > T[54]
c.245T > C[87]
c.249_250insT[18]
270T > C[54]
402C > T[54]
585G > C[54]
c.611 + 1G > A[70]
c.611 + 4A > G[36]
c.612 − 15_−6del10bp[55]
c.625A > C[31]
c.627 + 5G > T[31]
c.625A > C/c.627 + 5G > T[31]
696G > T[54]
c. 784 + 1G > C[49]
807T > C[54]
c.886G > T[31]
c.890A > G[59]
c.908 + 1G > A[57]
c.908 + 5G > A[55]
c.908delG[59]
c.909 − 15A > G[66]
957A > G[54]
c.1084 − 2A > G[57]
1145 1 bp deletion[90]
1281C > T[54,57]
c.1309 − 165C > T[19]
c.1434 + 174G > A[19]
c.1434 + 70C > T[19]
c.1530C > A[57]
c.1587-1589delCTT[31]
c.1621A > C[33,59]
c.1638 + 32T > C[66]
c.1638 + 80C > T[66]
1671C > T[54]
1791G > T[54]
1939delA[14]
c.2075 + 3A > G[53]
c.2081T > A[31]
c.2093G > A[65]
2098delA[16]
c.2138 − 8T > G[67]
2142A > G[54]
c.2178 + 1G > T[36,39]
c.2179 − 17C > A[66]
c.2344 − 157T > G[66]
c.2344 − 17T > C[66]
c.2417G > A[78]
c.2541delG[87]
c.2620C > T[32,33]
c.2815 − 8A > G[55]
c.3003A > G[37]
c.3084A > G[48,54]
c.3213 + 4 A > G[9,37]
c.3213 + 5 G > A[9]
c.3268C > T[75]
3285A > G[54]

TABLE 3-continued

Exemplary ABCB11 Mutations c.3382C > T[75]
3435A > G[54]
c.3491delT[72]
c.3589C > T[57]
c.3765(+1 + 5)del5[42]
c.3766 − 34A > G[66]
c.3767 − 3768insC[6]
c.3770delA[67]
c.3826C > T[72]
c.3846C > T[57]
c.3929delG[67]
c.*236A > G[66]
1145delC[8]
Ex13_Ex17del[82]

TABLE 4

Selected ABCB11 Mutations Associated with PFIC-2

Amino acid position 1 (e.g., M1V)[9]
Amino acid position 4 (e.g., S4X)[64]
Amino acid position 19 (e.g., G19R)[56]
Amino acid position 25 (e.g., S25X)[14]
Amino acid position 26 (e.g., Y26Ifs*7)[38]
Amino acid position 50 (e.g., L50S)[7,57]
Amino acid position 52 (e.g., R52W)[26]
Amino acid position 58 (e.g., D58N)[62]
Amino acid position 62 (e.g., M62K)[9]
Amino acid position 66 (e.g., S66N)[17]
Amino acid position 68 (e.g., C68Y)[41]
Amino acid position 93 (e.g., Y93S)[13]
Amino acid position 101 (e.g., Q101Dfs*8)[9]
Amino acid position 107 (e.g., C107R)[36]
Amino acid position 112 (e.g., I112T)[9]
Amino acid position 114 (e.g., W114R)[2,9]
Amino acid position 129 (e.g., C129Y)[25]
Amino acid position 135 (e.g., E135K[13], E135L[17])
Amino acid position 167 (e.g., A167V[7], A167T[9,17])
Amino acid position 182 (e.g., I182K)[9]
Amino acid position 183 (e.g., M183V[8], M183T[9])
Amino acid position 225 (e.g., T225P)[57]
Amino acid position 226 (e.g., S226L)[9]
Amino acid position 232 (e.g., L232Cfs*9)[9]
Amino acid position 233 (e.g., L233S)[86]
Amino acid position 238 (e.g., G238V)[2,7]
Amino acid position 242 (e.g., T242I)[7]
Amino acid position 245 (e.g., I245Tfs*26)[57]
Amino acid position 256 (e.g., A256G)[9]
Amino acid position 260 (e.g., G260D)[57]
Amino acid position 284 (e.g., V284L)[7]
Amino acid position 297 (e.g., E297G)[2,7]
Amino acid position 303 (e.g., R303K[8], R303M[63], R303fsX321[83])
Amino acid position 304 (e.g., Y304X)[26]
Amino acid position 312 (e.g., Q312H)[7]
Amino acid position 313 (e.g., R313S)[7]
Amino acid position 314 (e.g., W314X)[57]
Amino acid position 318 (e.g., K318Rfs*26)[29]
Amino acid position 327 (e.g., G327E)[7]
Amino acid position 330 (e.g., V330X)[24]
Amino acid position 336 (e.g., C336S)[2,7]
Amino acid position 337 (e.g., Y337H)[21]
Amino acid position 342 (e.g., W342G)[50]
Amino acid position 354 (e.g., R354X)[9]
Amino acid position 361 (e.g., Q361X)[57]
Amino acid position 366 (e.g., V366D)[57]
Amino acid position 386 (e.g., G386X)[34]
Δ Amino acid positions 383-389[57]
Amino acid position 387 (e.g., R387H)[9]
Amino acid position 390 (e.g., A390P)[7]
Amino acid position 410 (e.g., G410D)[7]
Amino acid position 413 (e.g., L413W)[7]
Amino acid position 415 (e.g., R415X)[42]
Amino acid position 420 (e.g., I420T)[9]
Amino acid position 454 (e.g., V454X)[49]
Amino acid position 455 (e.g., G455E)[9]

TABLE 4-continued

Selected ABCB11 Mutations Associated with PFIC-2

Amino acid position 461 (e.g., K461E)[2,7]
Amino acid position 463 (e.g., T463I)[7]
Amino acid position 466 (e.g., Q466K)[7]
Amino acid position 470 (e.g., R470Q[7], R470X[9])
Amino acid position 472 (e.g., Y472X[14], Y472C[27])
Amino acid position 475 (e.g., C475X)[29]
Amino acid position 481 (e.g., V481E)[7]
Amino acid position 482 (e.g., D482G)[2,7]
Amino acid position 484 (e.g., H484Rfs*5)[9]
Amino acid position 487 (e.g., R487H[2], R487P[84])
Amino acid position 490 (e.g., N490D)[7]
Amino acid position 493 (e.g., W493X)[8]
Amino acid position 498 (e.g., I498T)[7]
Amino acid position 501 (e.g., V501G)[68]
Amino acid position 512 (e.g., I512T)[7]
Amino acid position 515 (e.g., N515T[7], N515D[64])
Amino acid position 516 (e.g., I516M)[17]
Amino acid position 517 (e.g., R517H)[7]
Amino acid position 520 (e.g., R520X)[57]
Amino acid position 523 (e.g., A523G)[13]
Amino acid position 528 (e.g., I528X)[9]
Amino acid position 540 (e.g., F540L)[46]
Amino acid position 541 (e.g., I541L[7], I541T[17])
Amino acid position 548 (e.g., F548Y)[7]
Amino acid position 549 (e.g., D549V)[9]
Amino acid position 554 (e.g., E554K)[21]
Amino acid position 559 (e.g., M559T)[57]
Amino acid position 562 (e.g., G562D)[7]
Amino acid position 570 (e.g., A570T[7], A570V[26])
Amino acid position 575 (e.g., R575X[2], R575Q[21])
Amino acid position 588 (e.g., A588V)[7]
Amino acid position 591 (e.g., N591S)[9,17]
Amino acid position 593 (e.g., S593R)[2,7]
Amino acid position 597 (e.g., V597V[9], V597L[13])
Amino acid positions 591 and 597 (e.g., N591S + V597V)[9]
Amino acid position 603 (e.g., K603K)[55]
Amino acid position 609 (e.g., H609Hfs*46)[26]
Amino acid position 610 (e.g., I610Gfs*45)[9]
Amino acid position 615 (e.g., H615R)[26]
Amino acid position 625 (e.g., T625Nfs*5)[26]
Amino acid position 627 (e.g., I627T)[7]
Amino acid position 636 (e.g., E636G)[2]
Amino acid position 669 (e.g., I669V)[26]
Amino acid position 698 (e.g., R609H)[9]
Amino acid positions 112 and 698 (e.g., I112T + R698H)[9]
Amino acid position 699 (e.g., S699P)[9]
Amino acid position 766 (e.g., G766R)[24]
Amino acid position 806 (e.g., G806G)[55]
Amino acid position 824 (e.g., G824E)[42]
Amino acid position 832 (e.g., R832C[7,26], R832H[41])
Amino acid position 842 (e.g., D842G)[2]
Amino acid position 859 (e.g., T859R)[7]
Amino acid position 865 (e.g., A865V)[45]
Amino acid position 877 (e.g., G877R)[56]
Amino acid position 893 (e.g., A893V)[57]
Amino acid position 901 (e.g., S901R)[17]
Amino acid position 903 (e.g., V903G)[57]
Δ Amino acid position 919[12]
Amino acid position 928 (e.g., R928X)[15,21]
Amino acid position 930 (e.g., K930Efs*79[10], K930Efs*49[26])
Amino acid position 948 (e.g., R948C)[7,26]
Amino acid position 979 (e.g., N979D)[7]
Amino acid position 982 (e.g., G982R)[2,7]
Amino acid positions 444 and 982 (e.g., V444A + G982R)[38]
Amino acid position 1001 (e.g., R1001R)[9]
Amino acid position 1003 (e.g., G1003R)[24]
Amino acid position 1004 (e.g., G1004D)[2,7]
Amino acid position 1027 (e.g., S1027R)[26]
Amino acid position 1028 (e.g., A1028A)[10]
Amino acid position 1032 (e.g., G1032R)[12]
Amino acid position 1041 (e.g., Y1041X)[9]
Amino acid position 1050 (e.g., R1050C)[57]
Amino acid position 1053 (e.g., Q1053X)[57]
Amino acid position 1055 (e.g., L1055P)[36]
Amino acid position 1057 (e.g., R1057X)[2]
Amino acid position 1058 (e.g., Q1058Hfs*38[9], Q1058fs*38[17])
Amino acid position 1061 (e.g., I1061Vfs*34)[9]
Amino acid position 1083 (e.g., C1083Y)[47]
Amino acid position 1090 (e.g., R1090X)[2]
Amino acid position 1099 (e.g., L1099Lfs*38)[26]
Amino acid position 1100 (e.g., S1100Qfs*38)[13]
Amino acid position 1110 (e.g., A1110E)[7]
Amino acid position 1116 (e.g., G1116R[7], G1116F[9,17], G1116E[36])
Amino acid position 1128 (e.g., R1128C)[7,13]
Amino acid position 1131 (e.g., D1131V)[27]
Amino acid position 1144 (e.g., S1144R)[7]
Amino acid position 1153 (e.g., R1153C[2,7], R1153H[7,26])
Amino acid position 1154 (e.g., S1154P)[7]
Amino acid position 1173 (e.g., N1173D)[57]
Amino acid position 1192 (e.g., A1192Efs*50)[9]
Amino acid position 1198 (e.g., H1198R)[27]
Amino acid position 1210 (e.g., T1210P[7], T1210F[57])
Amino acid position 1211 (e.g., N1211D)[7]
Amino acid position 1212 (e.g., V1212F)[36]
Amino acid position 1231 (e.g., R1231W[7], R1223Q[7])
Amino acid position 1232 (e.g., A1232D)[17]
Amino acid position 1235 (e.g., R1235X)[12]
Amino acid position 1242 (e.g., L1242I)[7]
Amino acid position 1256 (e.g., T1256fs*1296)[83]
Amino acid position 1268 (e.g., R1268Q)[2,7]
Amino acid position 1302 (e.g. E1302X)[57]
Amino acid position 1311 (e.g., Y1311X)[57]
Amino acid position 1316 (e.g., T1316Lfs*64)[15]
Intron 4 ((+3)A > C)[1]
Splice site mutation IVS7 + 1G > A[14]
IVS8 + 1G > C[76]
Splice site mutation IVS9 + 1G > T[14]
Splice site mutation IVS13del-13^-8[14]
Splice site mutation IVS16 − 8T > G[14]
Splice site mutation IVS18 + 1G > A[14]
Splice site mutation IVS19 + 2T > C[14]
IVS 23 − 8 G − A[36]
IVS24 + 5G > A[51]
Putative splice mutation 1198 − 1G > C[17]
Putative splice mutation 1810 − 3C > G[17]
Putative splice mutation 2178 + 1G > A[17]
Putative splice mutation 2344 − 1G > T[17]
Putative splice mutation 3213 + 1_3213 + 2delinsA[17]
c.-24C > A[78]
c.76 13 G > T[9]
c.77 − 19T > A[52]
c.90_93delGAAA[18]
c.124G > A[69]
c.150 + 3 A > C[10]
c.249_250insT[18]
c.611 + 1G > A[84]
c.611 + 4A > G[36]
c.612 − 15_-6del10bp[55]
c.625A > C[31]
c.627 + 5G > T[31]
c.625A > C/c.627 + 5G > T[31]
c.886C > T[31]
c.890A > G[59]
c.908 + 1G > A[57]
c.908 + 5G > A[55]
c.908delG[59]
1273 1 bp deletion[91]
c.1084 − 2A > G[57]
c.1445A > G[59]
c.1587-1589delCTT[31]
c.1621A > C[59]
1939delA[14]
c.2081T > A[31]
2098delA[16]
c.2343 + 1 G > T[80]
c.2178 + 1G > T[36]
c.2417G > A[78]
c.2620C > T[32]
c.2815 − 8A > G[55]
c.3003A > G[37]
c.3213 + 4 A > G[9,37]
c.3213 + 5 G > A[9]
c.3268C > T[75]
c.3382C > T[75]
c.3765(+1 + 5)del5[42]
c.3767-3768insC[6]

TABLE 4-continued

Selected ABCB11 Mutations Associated with PFIC-2

1145delC[8]
Ex13_Ex17del[82]

[A] A mutation to 'X' denotes an early stop codon

References for Tables 3 and 4

[1] Noe et al., J Hepatol. 2005, vol. 43(3), p. 536-543.
[2] Lam et al., Am J Physiol Cell Physiol. 2007, vol. 293(5), p. C1709-16.
[3] Stindt et al., Liver Int. 2013, vol. 33(10), p. 1527-1735.
[4] Gao et al., Shandong Yiyao 2012, vol. 52(10), p. 14-16.
[5] Strautnieks et al., Gastroenterology. 2008, vol. 134(4), p. 1203-1214.
[6] Kagawa et al., Am J Physiol Gastrointest Liver Physiol. 2008, vol. 294(1), p. G58-67.
[7] Byrne et al., Hepatology. 2009, vol. 49(2), p. 553-567.
[8] Chen et al., J Pediatr. 2008, vol. 153(6), p. 825-832.
[9] Davit-Spraul et al., Hepatology 2010, vol. 51(5), p. 1645-1655.
[10] Dröge et al., Sci Rep. 2016, vol. 6: 24827.
[11] Lang et al., Pharmacogenet Genomics. 2007, vol. 17(1), p. 47-60.
[12] Ellinger et al., World J Gastroenterol. 2017, vol. 23(29), p. 5295-5303.
[13] Vitale et al., J Gastroenterol. 2018, vol. 53(8), p. 945-958.
[14] Knisely et al., Hepatology. 2006, vol. 44(2), p. 478-86.
[15] Ellis et al., Hepatology. 2018, vol. 67(4), p. 1531-1545.
[16] Lam et al., J Hepatol. 2006, vol. 44(1), p. 240-242.
[17] Varma et al., Hepatology 2015, vol. 62(1), p. 198-206.
[18] Treepongkaruna et al., World J Gastroenterol. 2009, vol. 15(34), p. 4339-4342.
[19] Zarenezhad et al., Hepatitis Monthly: 2017, vol. 17(2); e43500.
[20] Hayashi et al., Hepatol Res. 2016, vol. 46(2), p. 192-200.
[21] Guorui et al., Linchuang Erke Zazhi 2013, vol. 31(10), 905-909.
[22] van Mil et al., Gastroenterology. 2004, vol. 127(2), p. 379-384.
[23] Anzivino et al., Dig Liver Dis. 2013, vol. 45(3), p. 226-232.
[24] Park et al., World J Gastroenterol. 2016, vol. 22(20), p. 4901-4907.
[25] Imagawa et al., J Hum Genet. 2018, vol. 63(5), p. 569-577.
[26] Giovannoni et al., PLoS One. 2015, vol. 10(12): e0145021.
[27] Hu et al., Mol Med Rep. 2014, vol. 10(3), p. 1264-1274.
[28] Lang et al., Drug Metab Dispos. 2006, vol. 34(9), p. 1582-1599.
[29] Masahata et al., Transplant Proc. 2016, vol. 48(9), p. 3156-3162.
[30] Holz et al., Hepatol Commun. 2018, vol. 2(2), p. 152-154.
[31] Li et al., Hepatology International 2017, vol. 11, No. 1, Supp. Supplement 1, pp. S180. Abstract Number: OP284.
[32] Francalanci et al., Laboratory Investigation 2011, vol. 91, Supp. SUPPL. 1, pp. 360A. Abstract Number: 1526.
[33] Francalanci et al., Digestive and Liver Disease 2010, vol. 42, Supp. SUPPL. 1, pp. S16. Abstract Number: T.N.S.
[34] Shah et al., J Pediatr Genet. 2017, vol. 6(2), p. 126-127.
Gao et al., Hepatitis Monthly 2017, vol. 17(10), e55087/1-e55087/6.
[36] Evason et al., Am J Surg Pathol. 2011, vol. 35(5), p. 687-696.
[37] Davit-Spraul et al., Mol Genet Metab. 2014, vol. 113(3), p. 225-229.
[38] Maggiore et al., J Hepatol. 2010, vol. 53(5), p. 981-6.
[39] McKay et al., Version 2. F1000Res. 2013; 2: 32. DOI: 10.12688/f1000 research. 2-32.v2
[40] Liu et al., Pediatr Int. 2013, vol. 55(2), p. 138-144.
[41] Waisbourd-Zinman et al., Ann Hepatol. 2017, vol. 16(3), p. 465-468.
[42] Griffin, et al., Canadian Journal of Gastroenterology and Hepatology 2016, vol. 2016. Abstract Number: A200. Meeting Info: 2016 Canadian Digestive Diseases Week, CDDW 2016. Montreal, QC, United States. 26 Feb. 2016-29 Feb. 2016
[43] Qiu et al., Hepatology 2017, vol. 65(5), p. 1655-1669.
[44] Imagawa et al., Sci Rep. 2017, 7:41806.
[45] Kang et al., J Pathol Transl Med. 2019 May 16. doi: 10.4132/jptm.2019.05.03. [Epub ahead of print]
[46] Takahashi et al., Eur J Gastroenterol Hepatol. 2007, vol. 19(11), p. 942-6.
[47] Shimizu et al., Am J Transplant. 2011, vol. 11(2), p. 394-398.
[48] Krawczyk et al., Ann Hepatol. 2012, vol. 11(5), p. 710-744.
[49] Sharma et al., BMC Gastroenterol. 2018, vol. 18(1), p. 107.
[50] Sattler et al., Journal of Hepatology 2017, vol. 66, No. 1, Suppl. S, pp. S177. Meeting Info.: International Liver Congress/52nd Annual Meeting of the European-Association-for-the-Study-of-the-Liver. Amsterdam, NETHERLANDS. Apr. 19-23, 2017. European Assoc Study Liver.
[51] Jung et al., J Pediatr Gastroenterol Nutr. 2007, vol. 44(4), p. 453-458.
[52] Sciveres. Digestive and Liver Disease 2010, vol. 42, Supp. SUPPL. 5, pp. S329. Abstract Number: CO18. Meeting Info: 17th National Congress SIGENP. Pescara, Italy. 7 Oct. 2010-9 Oct. 2010
[53] Sohn et al., Pediatr Gastroenterol Hepatol Nutr. 2019, vol. 22(2), p. 201-206.
[54] Ho et al., Pharmacogenet Genomics. 2010, vol. 20(1), p. 45-57.
[55] Wang et al., Hepatol Res. 2018, vol. 48(7), p. 574-584.
[56] Shaprio et al., J Hum Genet. 2010, vol. 55(5), p. 308-313.
[52] Bounford. University of Birmingham. Dissertation Abstracts International, (2016) Vol. 75, No. 1C. Order No.: AA110588329. ProQuest Dissertations & Theses.
[58] Stolz et al., Aliment Pharmacol Ther. 2019, vol. 49(9), p. 1195-1204.
[59] Jankowska et al., J Pediatr Gastroenterol Nutr. 2014, vol. 58(1), p. 92-95.
[60] Kim. Journal of Pediatric Gastroenterology and Nutrition 2016, vol. 62, Supp. SUPPL. 1, pp. 620. Abstract Number: H-P-045. Meeting Info: 49th Annual Meeting of the European Society for Paediatric Gastroenterology, Hepatology and Nutrition, ESPGHAN 2016. Athens, Greece. 25 May 2016-28 May 2016.
[61] Pauli-Magnus et al., Hepatology 2003, vol. 38, No. 4 Suppl. 1, pp. 518A. print. Meeting Info.: 54th Annual Meeting of the American Association for the Study of Liver Diseases. Boston, Mass., USA. Oct. 24-28, 2003. American Association for the Study of Liver Diseases.
[62] Li et al., Hepatology International 2017, vol. 11, No. 1, Supp. Supplement 1, pp. S362. Abstract Number: PP0347. Meeting Info: 26th Annual Conference of the Asian Pacific Association for the Study of the Liver, APASL 2017. Shanghai, China. 15 Feb. 2017-19 Feb. 2017.

[63] Rumbo et al., Transplantation 2018, vol. 102, No. 7, Supp. Supplement 1, pp. S848. Abstract Number: P. 752. Meeting Info: 27th International Congress of The Transplantation Society, TTS 2018. Madrid, Spain. 30 Jun. 2018-5 Jul. 2018.

[64] Lee et al., Pediatr Gastroenterol Hepatol Nutr. 2017, vol. 20(2), p. 114-123.

[65] Sherrif et al., Liver international: official journal of the International Association for the Study of the Liver 2013, vol. 33, No. 8, pp. 1266-1270.

[66] Blackmore et al., J Clin Exp Hepatol. 2013, vol. 3(2), p. 159-161.

[67] Matte et al., J Pediatr Gastroenterol Nutr. 2010, vol. 51(4), p. 488-493.

[68] Lin et al., Zhongguo Dang Dai Er Ke Za Zhi. 2018, vol. 20(9), p. 758-764.

[69] Harmanci et al., Experimental and Clinical Transplantation 2015, vol. 13, Supp. SUPPL. 2, pp. 76. Abstract Number: P62. Meeting Info: 1st Congress of the Turkic World Transplantation Society. Astana, Kazakhstan. 20 May 2015-22 May 2015.

[70] Herbst et al., Mol Cell Probes. 2015, vol. 29(5), p. 291-298.

[71] Moghadamrad et al., Hepatology. 2013, vol. 57(6), p. 2539-2541.

[72] Holz et al., Zeitschrift fur Gastroenterologie 2016, vol. 54, No. 8. Abstract Number: KV275. Meeting Info: Viszeralmedizin 2016, 71. Jahrestagung der Deutschen Gesellschaft fur Gastroenterologie, Verdauungs-und Stoffwechselkrankheiten mit Sektion Endoskopie—10. Herbsttagung der Deutschen Gesellschaft fur Allgemein- und Viszeralchirurgie. Hamburg, Germany. 21 Sep. 2016-24 Sep. 2016.

[73] Wang et al., PLoS One. 2016; vol. 11(4): e0153114.

[74] Hao et al., International Journal of Clinical and Experimental Pathology 2017, vol. 10(3), p. 3480-3487.

[75] Arnel et al., J Pediatr Gastroenterol Nutr. 2010, vol. 51(4), p. 494-499.

[76] Sharma et al., Indian Journal of Gastroenterology 2017, vol. 36, No. 1, Supp. Supplement 1, pp. A99. Abstract Number: M-20. Meeting Info: 58th Annual Conference of the Indian Society of Gastroenterology, ISGCON 2017. Bhubaneswar, India. 14 Dec. 2017-17 Dec. 2017.

[77] Beauséjour et al., Can J Gastroenterol. 2011, vol. 25(6), p. 311-314.

[78] Imagawa et al., Journal of Pediatric Gastroenterology and Nutrition 2016, vol. 63, Supp. Supplement 2, pp. S51. Abstract Number: 166. Meeting Info: World Congress of Pediatric Gastroenterology, Hepatology and Nutrition 2016. Montreal, QC, Canada. 5 Oct. 2016-8 Oct. 2016.

[79] Peng et al., Zhonghua er ke za zhi (Chinese journal of pediatrics) 2018, vol. 56, No. 6, pp. 440-444.

[80] Tibesar et al., Case Rep Pediatr. 2014, vol. 2014: 185923.

[81] Ng et al., Journal of Pediatric Gastroenterology and Nutrition 2018, vol. 66, Supp. Supplement 2, pp. 860. Abstract Number: H-P-127. Meeting Info: 51st Annual Meeting European Society for Paediatric Gastroenterology, Hepatology and Nutrition, ESPGHAN 2018. Geneva, Switzerland. 9 May 2018-12 May 2018.

[82] Wong et al., Clin Chem. 2008, vol. 54(7), p. 1141-1148.

[83] Pauli-Magnus et al., J Hepatol. 2005, vol. 43(2), p. 342-357.

[84] Jericho et al., Journal of Pediatric Gastroenterology and Nutrition. 60, vol. 3, p. 368-374.

[85] Scheimann et al., Gastroenterology 2007, vol. 132, No. 4, Suppl. 2, pp. A452. Meeting Info.: Digestive Disease Week Meeting/108th Annual Meeting of the American-Gastroenterological-Association. Washington, D.C., USA. May 19-24, 2007. Amer Gastroenterol Assoc; Amer Assoc Study Liver Dis; Amer Soc Gastrointestinal Endoscopy; Soc Surg Alimentary Tract.

[86] Jaquotot-Haerranz et al., Rev Esp Enferm Dig. 2013, vol. 105(1), p. 52-54.

[87] Khosla et al., American Journal of Gastroenterology 2015, vol. 110, No. Suppl. 1, pp. S397. Meeting Info.: 80th Annual Scientific Meeting of the American-College-of-Gastroenterology. Honolulu, Hi., USA. Oct. 16-21, 2015.

[88] Dröge et al., J Hepatol. 2017, vol. 67(6), p. 1253-1264.

[89] Liu et al., Liver International 2010, vol. 30(6), p. 809-815.

[90] Chen et al., Journal of Pediatrics 2002, vol. 140(1), p. 119-124.

[91] U.S. Pat. No. 9,295,677

In some embodiments, the mutation in ABCB11 is selected from A167T, G238V, V284L, E297G, R470Q, R470X, D482G, R487H, A570T, N591S, A865V, G982R, R1153C, and R1268Q.

Provided are methods of treating PFIC (e.g., PFIC-1 and PFIC-2) in a subject that includes performing an assay on a sample obtained from the subject to determine whether the subject has a mutation associated with PFIC (e.g., a ATP8B1, ABCB11, ABCB4, TJP2, NR1H4 or Myo5b mutation), and administering (e.g., specifically or selectively administering) a therapeutically effective amount of a compound of formula (I), or a pharmaceutically acceptable salt thereof, to the subject determined to have a mutation associated with PFIC. In some embodiments, the mutation is an ATP8B1 or ABCB11 mutation. For example, a mutation as provided in any one of Tables 1-4. In some embodiments, the mutation in ATP8B1 is selected from L127P, G308V, T456M, D554N, F529del, I661T, E665X, R930X, R952X, R1014X, and G1040R. In some embodiments, the mutation in ABCB11 is selected from A167T, G238V, V284L, E297G, R470Q, R470X, D482G, R487H, A570T, N591S, A865V, G982R, R1153C, and R1268Q.

Also provided are methods for treating PFIC (e.g., PFIC-1 and PFIC-2) in a subject in need thereof, the method comprising: (a) detecting a mutation associated with PFIC (e.g., a ATP8B1, ABCB11, ABCB4, TJP2, NR1H4 or Myo5b mutation) in the subject; and (b) administering to the subject a therapeutically effective amount of the formulation disclosed herein. In some embodiments, methods for treating PFIC can include administering a therapeutically effective amount of a compound of formula (I), or a pharmaceutically acceptable salt thereof, to a subject having a mutation associated with PFIC (e.g., an ATP8B1, ABCB11, ABCB4, TJP2, NR1H4 or Myo5b mutation). In some embodiments, the mutation is an ATP8B1 or ABCB11 mutation. For example, a mutation as provided in any one of Tables 1-4. In some embodiments, the mutation in ATP8B1 is selected from L127P, G308V, T456M, D554N, F529del, I661T, E665X, R930X, R952X, R1014X, and G1040R. In some embodiments, the mutation in ABCB11 is selected from A167T, G238V, V284L, E297G, R470Q, R470X, D482G, R487H, A570T, N591S, A865V, G982R, R1153C, and R1268Q.

In some embodiments, the subject is determined to have a mutation associated with PFIC in a subject or a biopsy sample from the subject through the use of any art recognized tests, including next generation sequencing (NGS). In some embodiments, the subject is determined to have a mutation associated with PFIC using a regulatory agency-approved, e.g., FDA-approved test or assay for identifying a mutation associated with PFIC in a subject or a biopsy sample from the subject or by performing any of the non-limiting examples of assays described herein. Additional methods of diagnosing PFIC are described in Gunaydin, M. et al., Hepat Med. 2018, vol. 10, p. 95-104, incorporated by reference in its entirety herein.

In some embodiments, the treatment of PFIC (e.g., PFIC-1 or PFIC-2) decreases the level of serum bile acids in the subject. In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of the formulation disclosed herein. In some embodiments, the treatment of PFIC includes treatment of pruritus.

In another aspect, the invention relates to a process for the preparation of the pharmaceutical formulation as disclosed herein, comprising the step of preparing a homogeneous aqueous suspension of odevixibat. In a preferred embodiment, the coating suspension is prepared by dispersing odevixibat in water by wet milling.

In a more specific embodiment, the process comprises the steps of:
a) wetting odevixibat in water using a homogenizer; and
b) dispersing the wetted odevixibat in water by wet milling, thereby obtaining a homogeneous aqueous suspension of odevixibat.

In some embodiments, odevixibat is sieved prior to the wetting of step a).

In some embodiments, the process further comprises the step of adding a film-forming polymer to the suspension. A film-forming polymer can facilitate a uniform dispersion of odevixibat in the suspension. The film-forming polymer may be added either before or after the wet milling step. In some embodiments, the wet milling is more effective in the absence of the film-forming polymer. In a preferred embodiment, therefore, the film-forming polymer is added to the homogeneous aqueous suspension of odevixibat obtained in step (b).

The homogeneity of the coating suspension may be checked either before or after addition of the film-forming polymer. When the size of the odevixibat agglomerates can be determined by optical microscopy, such as described in the experimental section, the coating suspension should not contain agglomerates larger than 200 µm. The suspension preferably does not contain agglomerates larger than 100 µm, and more preferably does not contain agglomerates larger than 50 µm. When the size of the agglomerates is determined by light scattering techniques, such as LALLS, the $d_{90}$ value for the particle size distribution of the coating suspension is preferably smaller than 15 µm, such as smaller than 14 µm, such as smaller than 13 µm, such as smaller than 12 µm, such as smaller than 11 µm, or such as smaller than 10 µm.

In another preferred embodiment, the coating suspension does not contain surfactants.

In another aspect, the invention relates to the formulation obtained by any of the processes disclosed herein.

Definitions

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "pharmaceutically acceptable" refers to those compounds, materials, compositions and/or dosage forms that are suitable for human pharmaceutical use and that are generally safe, non-toxic and neither biologically nor otherwise undesirable.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The term "crystal modification" refers to a crystalline solid phase of an organic compound. A crystal modification can be either a solvate or an ansolvate.

The term "solvate" refers to a crystalline solid phase of an organic compound, which has solvent (i.e., solvent molecules) incorporated into its crystal structure. A "hydrate" is a solvate wherein the solvent is water.

The term "sesquihydrate" refers to a hydrate containing about 1.5 moles of water associated with the crystal per mole of organic compound (i.e., a 1.5 hydrate). As used herein, a sesquihydrate includes from about 1.2 to about 1.8, more preferably from about 1.3 to about 1.7, more preferably from about 1.4 to about 1.6 and even more preferably from about 1.45 to about 1.55 moles of water associated with each mole of odevixibat in a crystal. The amount of water calculated herein excludes water adsorbed to the surface of the crystal.

The term "mixed solvate" refers to a crystalline solid phase of an organic compound, which has two or more different solvent molecules incorporated into its crystal structure. One of the at least two solvent molecules may be water.

The term "slurry" refers to a saturated solution to which an excess of solid is added, thereby forming a mixture of solid and saturated solution.

As used herein, the term "void volumes" refers to channels, layers or other more or less isolated voids in the crystal structure.

The crystallinity of a crystalline sample of odevixibat may be measured e.g. by X-Ray Powder Diffraction (XRPD) methods or by Differential Scanning calorimetry (DSC) methods, such as the method disclosed in the experimental section. When reference is made herein to a crystalline compound, preferably the crystallinity as measured by DSC methods is greater than about 70%, such as greater than about 80%, particularly greater than about 90%, more particularly greater than about 95%. In some embodiments, the degree of crystallinity as measured by DSC methods is greater than about 98%. In some embodiments, the degree of crystallinity as measured by DSC methods is greater than about 99%. The % crystallinity refers to the percentage by weight of the total sample mass which is crystalline.

The invention will now be described by the following examples which do not limit the invention in any respect. All cited documents and references mentioned herein are incorporated by reference in their entireties.

Abbreviations

DMF dimethylformamide
DMSO dimethyl sulfoxide
EtOH ethanol
MeOH methanol
RH relative humidity
2-PrOH 2-propanol Experimental Methods X-Ray Powder Diffraction (XRPD) Analysis Analyses were performed at 22° C. on a PANalytical X'Pert Pro diffractometer equipped with a Cu long fine focus X-ray tube and a PIXcel detector. Automatic divergence and anti-scatter slits were used together with 0.02 rad Soller slits and a Ni-filter. Dry samples were smeared onto cut Silicon Zero Background Holders (ZBH) and analysed between 2-40° in 2-theta with an analysis time of 17 minutes. All slurry samples were dripped on tempered porous Alumina filter substrates and analysed twice as they dried, first with a one minute 16-second scan (2-30° in 2-theta) and then a 7-minute scan (2-30° in 2-theta). A final 17-minute scan was performed when the sample had dried for several hours.

The samples were spun during analysis in order to increase the randomness of the samples. The following experimental settings were used:
Tube tension and current: 40 kV, 50 mA
Wavelength alpha1 (CuKα1): 1.5406 Å
Wavelength alpha1 (CuKα2): 1.5444 Å
Wavelength alpha1 and alpha1 mean (CuKα): 1.5418 Å

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation. For example, persons skilled in the art of XRPD will realise that the relative intensities of peaks may vary according to the orientation of the sample under the test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractometry", John Wiley & Sons, 1996).

Differential Scanning Calorimetry (DSC)

Experiments were performed using a TA Instruments Q2000 Differential Scanning calorimeter. The DCS crucible used was a TZero aluminum pan with pinhole (diameter ≥0.2 mm) in the lid. A dry nitrogen purge at a constant flow rate of 50 mL/min was maintained in the DSC cell throughout the measurement.

EXAMPLES

Example 1

Preparation of the Formulation (Small Scale)

Microcrystalline cellulose spheres were coated with one of two different coating suspensions of odevixibat, as indicated in Table 5 below, to obtain particles containing either 0.5% w/w or 1.5% w/w odevixibat.

TABLE 5

| Ingredient | Amount (g/batch) | Amount (g/batch) |
|---|---|---|
| Core: | | |
| Microcrystalline cellulose spheres 700 (Vivapur ® MCC sphere 700) | 1500 | 1500 |
| Coating: | 7.5 | 22.5 |
| Odevixibat | 30.0 | 90.0 |
| Hypromellose 3 mPa · s (Methocel ® E3 premium) | | |
| Purified water[a] | 337.5 | 1012.5 |
| Total (coated particles) | 1537.5 | 1612.5 |

[a]Purified water is removed during the coating and drying process.

Crystalline odevixibat was used. Typical values for the particle size distribution of the crystalline material were $d_{10}$=0.9 μm, $d_{50}$=4 μm and $d_{90}$=20 μm, wherein $d_{10}$, $d_{50}$ and $d_{90}$ are defined as the diameters where 10%, 50% and 90%, respectively, of the particle population lies below these values.

Coating Suspension

The coating suspension containing odevixibat drug substance was prepared in three steps:
a) Odevixibat suspension: odevixibat drug substance was sieved through a 0.5 mm sieve, followed by wetting in a small amount of the water using a homogenizer (Ultra Turrax T25; 15 minutes at approximately 6600-7000 rpm). The resulting wetted odevixibat drug substance was then dispersed in water by means of a colloid mill (IKA Magic Lab MKO or MK modules, 14600 rpm for 20 minutes, gap size 1.5 rotation) until the level of agglomerates met the in-process control acceptance limits.
b) Hypromellose dispersion: Hypromellose (3 mPa·s) was dispersed in hot water with mixing, and the resultant dispersion was cooled to room temperature.
c) Odevixibat coating suspension: The hypromellose dispersion was added to the odevixibat suspension in the colloid mill and the suspension was mixed for 4 minutes at 10000 rpm. Final mixing was continued at low speed using a magnetic stirrer. The odevixibat coating suspension was filtered through a 0.5 mm sieve before use in the coating process.

The dispersion of odevixibat in the coating suspension was monitored by optical microscopy, using a method based on European Pharmacopoeia 9.0, monograph 2.9.37, which was adjusted to be applicable for the odevixibat coating suspension. A Leica DMLB microscope equipped with a Leica DMC 2900 digital camera was used, and an objective with 10× magnification.

Samples were prepared by placing a small droplet of the coating suspension (using a Pasteur pipette) on a blank objective glass on top of a grid counting chamber of 4×4 test fields. A cover glass (about 18×18 mm, the same size as the grid) was placed on the droplet and slightly pressed on the centre to get a thin, even sample. The diameter of the sample was comparable with the size of the cover glass.

The objective was set with magnification ×10 and the scale bar was adjusted to 100 µm. Five replicates were scanned. The size of any agglomerates was checked by comparing them against the scale bar in four predetermined test fields for each replicate. The total number of agglomerates was calculated from 5 replicates×4 test fields, i.e. in total 20 test fields. The coating suspension was accepted if the 20 test fields did not contain more than 5 agglomerates 50 µm, and no agglomerates 200 µm.

Coating Process

Microcrystalline cellulose (MCC) spheres were coated using the odevixibat coating suspension in a fluid bed coater with Wurster insert. The amount of coating suspension on the MCC spheres is determined by weighing. The coated particles were sieved through a 0.5 mm and 1.25 mm sieve, respectively, in order to remove fine particles as well as twins. The particles were then transferred to bulk containers and handled as a drug product intermediate.

Capsule Filling

The calculated amount of particles required for each unit dose were filled into hard hydroxypropyl methylcellulose (HPMC) capsules (Size 0 or Size 3) using an automatic capsule filler, to provide four different strengths: 200, 400, 600 and 1200 µg.

The 200 and 600 µg strengths are Size 0 white capsules containing 40 mg of particles having an odevixibat concentration of 0.5% w/w and 1.5% w/w, respectively. These strengths will be used for patients with a weight range of 5.0 kg to <19.5 kg in the low- (40 µg/kg) and high- (120 µg/kg) dose groups of the Phase 3 clinical studies. The Size 0 capsules are designed to be opened so that the contents can be sprinkled onto a food vehicle for administration. They are not intended to be swallowed intact.

The 400 µg and 1200 µg strengths are Size 3 white capsules containing 80 mg of particles having an odevixibat concentration of 0.5% w/w and 1.5% w/w, respectively. These strengths will be used for patients with a weight range of 19.5 kg to >55.5 kg in the low- (40 µg/kg) and high- (120 µg/kg) dose groups of the Phase 3 clinical studies. The Size 3 capsules are intended to be swallowed intact.

The fill weight, the amounts of odevixibat and other ingredients and the capsule size for the different capsule strengths are shown in Table 6 below.

TABLE 6

| | Strength | | | |
|---|---|---|---|---|
| COMPONENT | 200 µg | 400 µg | 600 µg | 1200 µg |
| odevixibat concentration of particles | 0.5% w/w | | 1.5% w/w | |
| Fill weight (mg) (theoretical) Particles | 40 | 80 | 40 | 80 |
| Microcrystalline cellulose spheres 700 (Vivapur ® MCC sphere 700) | 39 | 78 | 37 | 74 |
| Odevixibat | 0.200 | 0.400 | 0.600 | 1.200 |
| Hypromellose 3 mPa · s (Methocel ® E3 Premium) | 0.8 | 1.6 | 2.4 | 4.8 |
| Capsule | | | | |
| Hypromellose capsule, white (Vcaps ® Plus) | Size 0 | Size 3 | Size 0 | Size 3 |

Example 2

Preparation of the Formulation (Larger Scale)

Microcrystalline cellulose spheres were coated with one of two different coating suspensions of odevixibat, as indicated in Table 7 below, to obtain particles containing either 0.5% w/w or 1.5% w/w odevixibat.

TABLE 7

| Ingredient | Amount (kg/batch) | Amount (kg/batch) |
|---|---|---|
| Core: | | |
| Microcrystalline cellulose spheres 700 (Vivapur ® MCC sphere 700) | 14.625 | 13.875 |
| Coating: | | |
| Odevixibat | 0.075 | 0.225 |
| Hypromellose 3 mPa · s (Methocel ® E3 premium) | 0.300 | 0.900 |
| Purified water[a] | 3.375 | 10.125 |
| Total (coated particles) | 15.000 | 15.000 |

[a]Purified water is removed during the coating and drying process.

Crystalline odevixibat was used. Typical values for the particle size distribution of the crystalline material were $d_{10}$=0.9 µm, $d_{50}$=4 µm and $d_{90}$=20 µm, wherein $d_{10}$, $d_{50}$ and $d_{90}$ are defined as the diameters where 10%, 50% and 90%, respectively, of the particle population lies below these values.

Coating Suspension

The coating suspension containing odevixibat drug substance was prepared in three steps:
  a) odevixibat suspension: odevixibat drug substance was wetted in a small amount of the water using a homogenizer (Ultra Turrax T25; 15 minutes at approximately 6600-7000 rpm). The resulting wetted odevixibat drug substance was then dispersed in water by means of a colloid mill (IKA Magic Lab MKO or MK modules, 14600 rpm for 20 minutes, gap size 1.5 rotation) until the level of agglomerates met the in-process control acceptance limits, i.e. $d_{90}$<12 µm (as determined by low-angle laser light scattering (LALLS)).
  b) hypromellose dispersion: Hypromellose (3 mPa·s) was dispersed in hot water with mixing, and the resultant dispersion was cooled to room temperature.
  c) odevixibat coating suspension: The hypromellose dispersion was added to the odevixibat suspension and the suspension was mixed. Final mixing was continued at low speed using a stirrer. The odevixibat coating suspension was filtered through a 0.5 mm sieve before use in the coating process.

Coating Process

The obtained odevixibat coating suspension was used for coating microcrystalline cellulose (MCC) spheres in accordance with the coating process described in Example 1.

Capsule Filling

Capsules were prepared in accordance with Example 1. The fill weight, the amounts of odevixibat and other ingredients and the capsule size for the different capsule strengths were as presented in Table 5 above.

Example 3

Preparation of Crystal Modification 1

Absolute alcohol (100.42 kg) and crude odevixibat (18.16 kg) were charged to a 250-L GLR with stirring under nitrogen atmosphere. Purified water (12.71 kg) was added and the reaction mass was stirred under nitrogen atmosphere at 25±5° C. for 15 minutes. Stirring was continued at 25±5° C. for 3 to 60 minutes, until a clear solution had formed. The solution was filtered through a 5.0 μSS cartridge filter, followed by a 0.2 μPP cartridge filter and then transferred to a clean reactor. Purified water (63.56 kg) was added slowly over a period of 2 to 3 hours at 25±5° C., and the solution was seeded with crystal modification 1 of odevixibat. The solution was stirred at 25±5° C. for 12 hours. During this time, the solution turned turbid. The precipitated solids were filtered through centrifuge and the material was spin dried for 30 minutes. The material was thereafter vacuum dried in a Nutsche filter for 12 hours. The material was then dried in a vacuum tray drier at 25±5° C. under vacuum (550 mm Hg) for 10 hours and then at 30±5° C. under vacuum (550 mm Hg) for 16 hours. The material was isolated as an off-white crystalline solid. The isolated crystalline material was milled and stored in LDPE bags.

An overhydrated sample was analyzed with XRPD and the diffractogram is shown in FIG. 2. Another sample was dried at 50° C. in vacuum and thereafter analysed with XRPD. The diffractogram of the dried sample is shown in FIG. 1.

The diffractograms for the drying of the sample are shown in FIGS. 3 and 4 for 2θ ranges 5-13° and 18-25°, respectively (overhydrated sample at the bottom and dry sample at the top).

Example 4

Preparation of Crystal Modification 2 from Ethanol and Water 105.9 mg of odevixibat were weighed into a 1 mL Chromacol vessel. A magnetic stir bar and 1.0 mL of an ethanol:water 70:30% v/v mixture were added and the vessel was closed with a crimped cap. The resulting slurry was then left stirred at 25° C. for 1 week.

Figure 5:
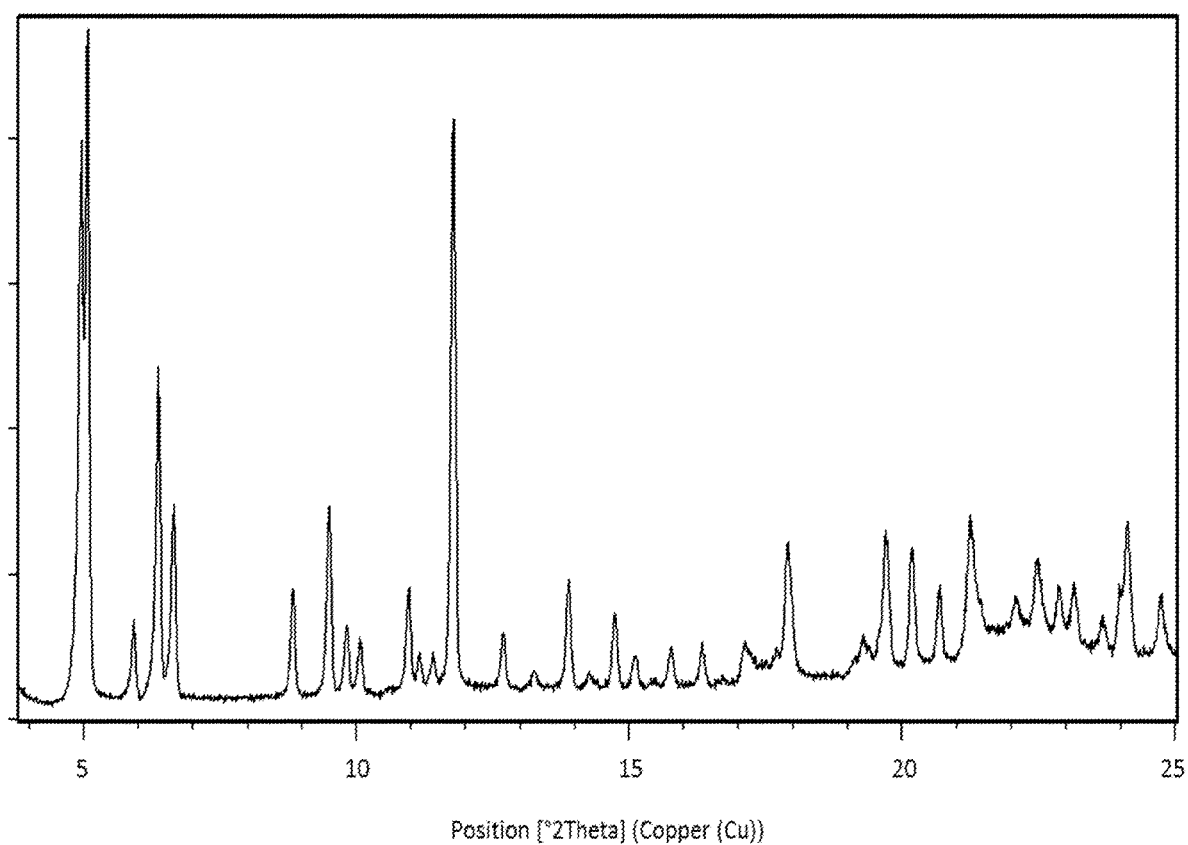
FIG. 5 shows the X-ray powder diffractogram of crystal modification 2A, as obtained from a mixture of ethanol and water (70:30% v/v).

The wet sample was analyzed with XRPD and the diffractogram is shown in FIG. 5. Upon drying of the sample, it transformed into crystal modification 1.

Example 5

Determination of Crystalline Fraction by Differential Scanning Calorimetry

This method quantifies the crystalline fraction of odevixibat drug substance in partially crystalline samples. The quantification is based on the assumption that partially crystalline samples are binary mixtures of the crystalline hydrate and the amorphous phase of odevixibat. The crystalline fraction is quantified based on the melting enthalpy of an anhydrous form. This anhydrous form is the dehydrated hydrate which spontaneously and reproducibly forms by drying the hydrate at elevated temperature.

5-6 mg of a sample of a crystalline or partially crystalline sample of odevixibat was accurately weighed into a DSC crucible which was then closed with a perforated lid using a suitable press. The total weight of the DSC crucible (pan+lid+sample) was noted and the total weight of the crucible was again determined after the DSC test. The weight loss during the DSC test must not be more than 5%.

The DSC test consists of three cycles:
Cycle 1: an increase in temperature from 20° C. to 120° C. at a scanning rate of 5° C./min;
Cycle 2: a decrease in temperature from 120° C. to 80° C. at a scanning rate of 10° C./min; and
Cycle 3: an increase in temperature from 80° C. to 200° C. at a scanning rate of 10° C./min.

The first scan cycle dries the sample and thereby converts the hydrate form into a dehydrated hydrate (an anhydrous form). In the second scan cycle, the sample is cooled down to obtain a stable baseline in the subsequent heat-up for signal integration. The melting enthalpy is determined in the third scan cycle, where the sample is heated through the melting of the anhydrous form.

Figure 6:
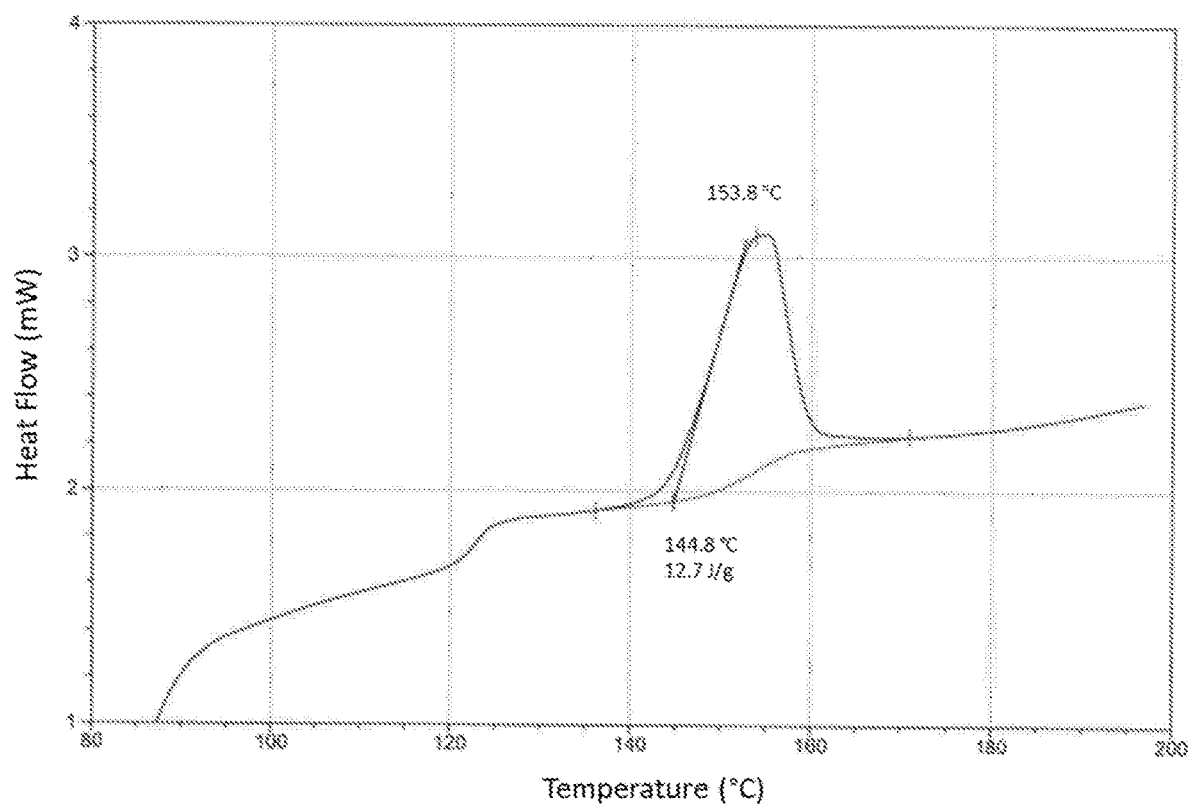
FIG. 6 shows the DSC trace of a sample of odevixibat with about 50% crystalline fraction (after pre-heating and cooling).

The endothermic event due to melting appears in the temperature range of 140-165° C. The peak must be integrated over a sigmoidal tangent baseline using the Sig Tangent integration function of the TA Universal Analysis software. The integration should start at a temperature between 130° C. and 140° C., and end at a temperature between 165° C. and 175° C., depending on the actual baseline. The glass transition of the amorphous part may appear in the temperature range of 120-130° C., depending on the actual amorphous fraction (see FIG. 6 for an example). If an irregular baseline does not allow the integration, it should be assessed whether the drying of the sample was incomplete.

The evaluation of the melting enthalpy is done by using the dry weight of the sample, which is obtained by subtracting the total weight of the DSC crucible (pan+lid+sample) after the DSC test from the total weight of the crucible before the test. The percent weight loss during the DSC scan, which is the difference between the initial weight and the dry weight divided by the initial weight, must not be more than 5%; otherwise the crystalline content of the sample cannot be calculated. The crystalline fraction expressed in weight percent is to be calculated from the melting enthalpy ($\Delta H_{sample}$) based on the following formula. The value shall be given on an integer number.

$$\% \text{ crystalline content} = \frac{\Delta H_{sample} + 1.1626}{0.2815}$$

Example 6

Homogeneity Monitored by LALLS

The homogeneity of odevixibat coating suspensions was studied using low-angle laser light scattering (LALLS). Three odevixibat coating suspensions intended for particles containing 0.5% w/w odevixibat were produced by dispersing odevixibat drug substance (16 g) in water (200 g) with an Ultra Turrax homogenizer for 7 minutes. When the drug substance was dispersed, the homogenizer was run for an additional 8 minutes. The homogenizer was then rinsed with water (216 g), which was added to the suspension.

The odevixibat suspensions were then dispersed using a wet mill (IKA Magic Lab and MK module), using the settings presented in Table 8. Methocel E3 was dispersed in hot water (85-90° C.) while mixing with an overhead stirrer and then cooled to room temperature. The concentration was adjusted to 17.4% w/w by the addition of water.

368 g of the Methocel gel was charged to the odevixibat suspension and mixed using the wet mill for another 4 minutes at 10000 rpm. The temperature of the suspension was checked during the process. The homogeneity of the odevixibat suspension was monitored with LALLS after 0, 5, 10, 15 and 20 minutes recirculation time. The data are presented in Table 9.

TABLE 8

| | Suspension No. | | |
|---|---|---|---|
| | 1 | 2 | 3 |
| Dispersion (Ultra Turrax) | | | |
| Time (min) | 15 | 15 | 15 |
| Speed (rpm) | 6800-8000 | 7600-8000 | 6600-8000 |
| Dispersion (Wet mill) | | | |
| Gap (rotations) | 1.5 | 1.5 | 1.0 |
| Time (min) | 20 | 20 | 20 |
| Speed (rpm) | 14600 | 14600 | 14600 |
| Cooling (MK module) | | | |
| Set point (° C.) | N/A | 25 | 10 |
| Temperature (° C.) of coating suspension after 20 min wet milling | 72 | 50 | 55 |

TABLE 9

| Suspension No. | Recirculation time (min) | LALLS (μm) | | | Comments |
|---|---|---|---|---|---|
| | | $d_{10}$ | $d_{50}$ | $d_{90}$ | |
| 1 | 0 | 1.5 | 5.5 | 17.9 | |
| | 5 | 1.1 | 3.9 | 10.5 | |
| | 10 | 1.2 | 3.9 | 9.3 | |
| | 15 | 2.4 | 5.2 | 11.3 | |
| | 20 | 1.8 | 4.1 | 8.8 | Sample taken after addition of Methocel |
| | 20 | 1.6 | 3.9 | 8.7 | Sample taken after 5 days storage at room temperature with magnetic stirring |
| 2 | 0 | 1.5 | 6.5 | 29.1 | |
| | 5 | 1.2 | 4.3 | 11.4 | |
| | 10 | 1.1 | 3.8 | 9.3 | |
| | 15 | 1.1 | 3.6 | 8.5 | |
| | 20 | 1.0 | 3.5 | 8.2 | Sample taken when wet milling was finished |
| | 20 | 1.1 | 3.7 | 8.6 | Sample taken after addition of Methocel |
| 3 | 0 | n.d. | n.d. | n.d. | |
| | 5 | 0.9 | 3.4 | 8.8 | |
| | 10 | 0.9 | 3.2 | 7.7 | |
| | 15 | 1.1 | 3.7 | 8.5 | |
| | 20 | 1.1 | 3.8 | 8.9 | Sample taken when wet milling was finished |
| | 20 | 1.0 | 3.4 | 8.0 | Sample taken after addition of Methocel |

Example 7

Content Uniformity

Pellets of two different strengths, 0.5% w/w and 1.5% w/w, were prepared as described in Example 1. The amount of odevixibat in a capsule was determined for 30 capsules, using reversed-phase high-performance liquid chromatography (RP-HPLC). Mobile phase: 40:60 acetonitrile:acetate buffer pH 5.5; flow rate 1.5 mL/min; column: Zorbax SB-CN (50×4.6 mm, 3.5 μm). The assayed amount of odevixibat and the content uniformity are presented in Table 10.

TABLE 10

| Odevixibat concentration in particles | 0.5% w/w | 1.5% w/w | 0.5% w/w |
|---|---|---|---|
| Assay (mg/g) | 4.98 | 14.2 | 4.88 |
| Content Uniformity: RSD % (n = 30) | 1.6 | 0.8 | 1.4 |

Example 8

Stability Testing at Low pH

The compatibility between particles coated with odevixibat and yoghurt, apple sauce, or fruit purée was evaluated by sprinkling about 40 mg of coated particles containing 0.5% w/w odevixibat (corresponding to the contents one 200 μg capsule) onto 1 tablespoon of the food and determining recovery over a period of 120 minutes. The recovery of odevixibat was determined using a reversed-phase high-performance liquid chromatography (RP-HPLC) method. Mobile phase: 40:60 acetonitrile:acetate buffer pH 5.5; flow rate 1.5 mL/min; column: Zorbax SB-CN (50×4.6 mm, 3.5 μm).

The recovery for all food samples ranged between 95% to 101% with no change over time. Visual inspection concluded that the particles were intact for up to 6 hours for all samples; no colour differences and no dissolved particles were observed. The results verify that patients who sprinkle the particles onto food will receive the intended dose. A summary of the foods tested is presented in Table 11, and the results of the recovery testing are presented in Table 12 (apple sauce), Table 13 (yoghurt smoothie), and Table 14 (fruit purée).

TABLE 11

| Food | Brand | pH | Ingredients |
|---|---|---|---|
| Apple sauce | Eldorado | 3.7 | Apple 92%, sugar 7%, antioxidant (ascorbic acid), preservatives (E202) |
| Yoghurt smoothie | Semper | 3.9 | Banana 42%, strawberry 30%, yoghurt (heat treated) 20%, water, corn starch, chokeberry juice concentrate, lemon juice concentrate, antioxidant (ascorbic acid) |
| Fruit purée | Semper | 3.9 | Water, orange juice (from concentrate) 23%, apple 20%, banana 15%, rice starch, vitamin C, iron |

TABLE 12

| Time (min) | Added particle weight (mg) | Nominal amount of odevixibat (μg) | Assay for odevixibat (μg) | Recovery (%) | Mean (%) |
|---|---|---|---|---|---|
| 0 | 39.58 | 201.07 | 199.35 | 99.1 | 99 |
| | 42.35 | 215.14 | 212.28 | 98.7 | |
| 15 | 40.37 | 205.08 | 187.29 | 91.3 | 96 |
| | 40.37 | 205.08 | 205.37 | 100.1 | |
| 30 | 41.21 | 209.35 | 206.45 | 98.6 | 98 |
| | 39.97 | 203.05 | 197.70 | 97.4 | |
| 60 | 40.50 | 205.74 | 198.14 | 96.3 | 97 |
| | 40.20 | 204.22 | 199.99 | 97.9 | |
| 120 | 39.61 | 201.22 | 199.22 | 99.0 | 98 |
| | 40.12 | 203.81 | 199.65 | 98.0 | |

TABLE 13

| Time (min) | Added particle weight (mg) | Nominal amount of odevixibat (μg) | Assay for odevixibat (μg) | Recovery (%) | Mean (%) |
|---|---|---|---|---|---|
| 0 | 42.07 | 213.72 | 213.60 | 99.9 | 99 |
| | 42.38 | 215.29 | 209.17 | 97.2 | |
| 15 | 41.24 | 209.50 | 206.01 | 98.3 | 97 |
| | 40.42 | 205.33 | 195.58 | 95.2 | |
| 30 | 40.70 | 206.76 | 199.48 | 96.5 | 96 |
| | 41.96 | 213.16 | 203.30 | 95.4 | |

TABLE 13-continued

| Time (min) | Added particle weight (mg) | Nominal amount of odevixibat (μg) | Assay for odevixibat (μg) | Recovery (%) | Mean (%) |
|---|---|---|---|---|---|
| 60 | 40.39 | 205.18 | 197.33 | 96.2 | 96 |
|  | 39.38 | 200.05 | 192.06 | 96.0 |  |
| 120 | 40.99 | 208.23 | 199.05 | 95.6 | 96 |
|  | 39.42 | 200.25 | 192.38 | 96.1 |  |

TABLE 14

| Time (min) | Added particle weight (mg) | Nominal amount of odevixibat (μg) | Assay for odevixibat (μg) | Recovery (%) | Mean (%) |
|---|---|---|---|---|---|
| 0 | 43.57 | 221.34 | 188.05 | 85.0 | 95 |
|  | 37.79 | 191.97 | 200.25 | 104.3 |  |
| 15 | 39.74 | 201.88 | 194.86 | 96.5 | 101 |
|  | 39.34 | 199.85 | 209.63 | 104.9 |  |
| 30 | 41.72 | 211.94 | 203.61 | 96.1 | 101 |
|  | 41.77 | 212.19 | 226.27 | 106.6 |  |
| 60 | 42.25 | 214.63 | 208.02 | 96.9 | 96 |
|  | 43.39 | 220.42 | 210.74 | 95.6 |  |
| 120 | 39.05 | 198.37 | 196.18 | 98.9 | 97 |
|  | 40.33 | 204.88 | 196.19 | 95.8 |  |

The primary degradation pathway expected for odevixibat particles, when mixed with the specified food vehicles for administration, is acidic hydrolysis of the dipeptide moiety. To evaluate the chemical stability of the odevixibat particles, 1 mL of phosphate buffer pH 3.0 was added to about 200 mg of particles containing 0.5% w/w odevixibat (i.e., the content of five 200 μg capsules) and left at room temperature for 2 hours. No degradation was observed.

Example 9

Long-Term Stability Testing

Odevixibat capsules of size 0 and size 3, prepared in accordance with Example 1, were stored in a HDPE bottle with an HDPE cap and kept at 25° C. and 60% relative humidity as the long-term storage condition, and at 40° C. and 75% relative humidity as the accelerated condition. The amounts of odevixibat, related substances and water were determined after 1, 3, 6, 9 and 12 months for samples stored at 25° C./60% RH, and after 1, 3, and 6 months for samples stored at 40° C./75% RH. The results for capsules of strength 200 μg (Size 0) are presented in Table 15; for capsules of strength 600 μg (Size 0) in Table 16; for capsules of strength 400 μg (Size 3) in Table 17; and for capsules of strength 1200 μg (Size 3) in Table 18.

TABLE 15

Stability data for capsules of strength 200 μg.

| Test | Acceptance Criteria | Storage Conditions | Storage period (months) | | | | | |
|---|---|---|---|---|---|---|---|---|
|  |  |  | 0 | 1 | 3 | 6 | 9 | 12 |
| Description | White oblong hard capsule containing white to off-white pellets | 25° C./60% RH | Conforms | Conforms | Conforms | Conforms | Conforms | Conforms |
|  |  | 40° C./75% RH |  | Conforms | Conforms | Conforms |  |  |
| Assay | 180-220 μg/capsule | 25° C./60% RH | 207 | 205 | 206 | 204 | 209 | 207 |
|  |  | 40° C./75% RH |  | 206 | 206 | 205 |  |  |
| Related Substances, Total | ≤4.0% | 25° C./60% RH | 0.53 | 0.51 | 0.48 | 0.47 | 0.55 | 0.57 |
|  |  | 40° C./75% RH |  | 0.44 | 0.63 | 0.90 |  |  |
| Dissolution | Q = 75% at 45 mins | 25° C./60% RH | 104 | 101 | 102 | 102 | 106 | 106 |
|  |  | 40° C./75% RH |  | 99 | 102 | 101 |  |  |
| Water Content | Report (%) | 25° C./60% RH | 3.3 | NT | NT | 3.5 | NT | 4.3 |
|  |  | 40° C./75% RH |  | NT | NT | 4.5 |  |  |

TABLE 16

Stability data for capsules of strength 600 μg.

| Test | Acceptance Criteria | Storage Conditions | Storage period (months) | | | | | |
|---|---|---|---|---|---|---|---|---|
|  |  |  | 0 | 1 | 3 | 6 | 9 | 12 |
| Description | White oblong hard capsule containing white to off-white pellets | 25° C./60% RH | Conforms | Conforms | Conforms | Conforms | Conforms | Conforms |
|  |  | 40° C./75% RH |  | Conforms | Conforms | Conforms |  |  |
| Assay | 540-660 μg/capsule | 25° C./60% RH | 576 | 600 | 596 | 597 | 603 | 599 |
|  |  | 40° C./75% RH |  | 599 | 612 | 601 |  |  |
| Related Substances, Total | ≤4.0% | 25° C./60% RH | 0.53 | 0.52 | 0.47 | 0.44 | 0.43 | 0.41 |
|  |  | 40° C./75% RH |  | 0.45 | 0.48 | 0.73 |  |  |

TABLE 16-continued

Stability data for capsules of strength 600 μg.

| Test | Acceptance Criteria | Storage Conditions | Storage period (months) | | | | | |
|---|---|---|---|---|---|---|---|---|
| | | | 0 | 1 | 3 | 6 | 9 | 12 |
| Dissolution | Q = 75% at 45 mins | 25° C./60% RH | 99 | 99 | 100 | 97 | 102 | 106 |
| | | 40° C./75% RH | | 100 | 99 | 96 | | |
| Water Content | Report (%) | 25° C./60% RH | 3.4 | NT | NT | 3.3 | NT | 4.4 |
| | | 40° C./75% RH | | NT | NT | 4.4 | | |

TABLE 17

Stability data for capsules of strength 400 μg.

| Test | Acceptance Criteria | Storage Conditions | Storage period (months) | | | | | |
|---|---|---|---|---|---|---|---|---|
| | | | 0 | 1 | 3 | 6 | 9 | 12 |
| Description | White oblong hard capsule containing white to off-white pellets | 25° C./60% RH | Conforms | Conforms | Conforms | Conforms | Conforms | Conforms |
| | | 40° C./75% RH | | Conforms | Conforms | Conforms | | |
| Assay | 360-440 μg/capsule | 25° C./60% RH | 397 | 395 | 397 | 400 | 396 | 399 |
| | | 40° C./75% RH | | 394 | 392 | 398 | | |
| Related Substances, Total | ≤4.0% | 25° C./60% RH | 0.63 | 0.51 | 0.47 | 0.57 | 0.57 | 0.59 |
| | | 40° C./75% RH | | 0.42 | 0.55 | 0.83 | | |
| Dissolution | Q = 75% at 45 mins | 25° C./60% RH | 100 | 99 | 99 | 99 | 102 | 99 |
| | | 40° C./75% RH | | 100 | 101 | 99 | | |
| Water Content | Report (%) | 25° C./60% RH | 3.7 | NT | NT | 3.1 | NT | 4.2 |
| | | 40° C./75% RH | | NT | NT | 4.3 | | |

TABLE 18

Stability data for capsules of strength 1200 μg.

| Test | Acceptance Criteria | Storage Conditions | Storage period (months) | | | | | |
|---|---|---|---|---|---|---|---|---|
| | | | 0 | 1 | 3 | 6 | 9 | 12 |
| Description | White oblong hard capsule containing white to off-white pellets | 25° C./60% RH | Conforms | Conforms | Conforms | Conforms | Conforms | Conforms |
| | | 40° C./75% RH | | Conforms | Conforms | Conforms | | |
| Assay | 1080-1320 μg/capsule | 25° C./60% RH | 1191 | 1194 | 1174 | 1169 | 1196 | 1175 |
| | | 40° C./75% RH | | 1200 | 1192 | 1191 | | |
| Related Substances, Total | ≤4.0% | 25° C./60% RH | 0.53 | 0.51 | 0.48 | 0.46 | 0.44 | 0.51 |
| | | 40° C./75% RH | | 0.55 | 0.51 | 0.63 | | |
| Dissolution | Q = 75% at 45 mins | 25° C./60% RH | 99 | 97 | 99 | 99 | 98 | 98 |
| | | 40° C./75% RH | | 101 | 100 | 98 | | |
| Water Content | Report (%) | 25° C./60% RH | 3.5 | NT | NT | 3.0 | NT | 4.1 |
| | | 40° C./75% RH | | NT | NT | 4.3 | | |

Example 10

Blend Uniformity of Pellets

Particles of two different strengths, 0.5% w/w and 1.5% w/w, were prepared as described in Example 2. The sieved pellets were collected in a 55 L drum, lined with a PE bag. The pellets were sampled from 10 different locations of the drum with a sampling thief tip of 0.25 mL. The average sample from each location was 80 mg, corresponding to the content of two Size 0 capsules of 200 μg or 600 μg, or one Size 3 capsule of 400 μg or 1200 rig. The content of odevixibat was determined by RP-UPLC: Mobile phase A: 80:20 ammonium acetate buffer pH 5.7/acetonitrile; Mobile phase B: 20:80 ammonium acetate buffer pH 5.7/acetonitrile; flow rate 0.40 mL/min; column: Waters Acquity BEH C8 100×2.1 mm, 1.7 mm; Gradient: 0 min: 60% A:40% B, 12 min: 20% A:80% B, 13.5 min: 20% A:80% B, 13.6 min: 60% A:40% B, 15 min: 60% A:40% B. The assayed amount of odevixibat and the content uniformity are presented in Table 19.

TABLE 19

| | Assay for odevixibat (% of Label Claim) | |
|---|---|---|
| Sample | 0.5% w/w | 1.5% w/w |
| 1 | 101.7 | 99.5 |
| 2 | 97.6 | 101.7 |
| 3 | 98.8 | 101.1 |
| 4 | 100.8 | 101.5 |
| 5 | 100.4 | 97.7 |
| 6 | 99.7 | 98.5 |
| 7 | 100.4 | 102.7 |
| 8 | 99.5 | 103.5 |
| 9 | 98.4 | 102.5 |
| 10 | 99.5 | 100.6 |
| Mean | 99.7 | 100.9 |
| Min | 97.6 | 97.7 |
| Max | 101.7 | 103.5 |
| RSD (%) | 1.2 | 1.9 |

The invention claimed is:

1. A pharmaceutical formulation of odevixibat, comprising a plurality of particles, wherein each particle is between about 0.1 and about 1.5 mm in size and comprises:
   a) a core comprising microcrystalline cellulose, and
   b) a coating layer surrounding the core, wherein the coating layer comprises odevixibat, or a pharmaceutically acceptable salt thereof, and a film-forming polymer; and wherein the coating layer comprises odevixibat agglomerates having a $d_{90}$ particle size distribution of less than 15 μm;
wherein each particle contains odevixibat, or a pharmaceutically acceptable salt thereof, in an amount of from about 0.1% w/w to about 2.0% w/w based on the total weight of the particle, and each particle of the formulation substantially contains the same amount of odevixibat.

2. The formulation according to claim 1, wherein each particle contains odevixibat, or a pharmaceutically acceptable salt thereof, in an amount of about 0.5% w/w based on the total weight of the particle.

3. The formulation according to claim 1, wherein each particle contains odevixibat, or a pharmaceutically acceptable salt thereof, in an amount of about 1.5% w/w based on the total weight of the particle.

4. The formulation according to claim 1, wherein the core does not contain odevixibat.

5. The formulation according to claim 1, wherein the coating layer is prepared by spraying onto the cores a homogeneous suspension of odevixibat in water.

6. The formulation according to claim 5, wherein the homogenous suspension is prepared by dispersing odevixibat in water by wet milling.

7. The formulation according to claim 5, wherein the homogenous suspension does not contain agglomerates of odevixibat that are larger than 200 μm.

8. The formulation according to claim 1, wherein the coating layer does not contain a surfactant.

9. The formulation according to claim 1, wherein the particles are between about 0.1 and about 1.0 mm in size.

10. The formulation according to claim 1, wherein odevixibat is present as a crystalline hydrate of odevixibat.

11. The formulation according to claim 1, wherein odevixibat is present as crystal modification 1 of odevixibat.

12. The formulation according to claim 11, wherein crystal modification 1 of odevixibat has an X-ray powder diffraction (XRPD) pattern, obtained with CuKα1-radiation, with at least specific peaks at °2θ positions 5.6±0.2, 6.7±0.2 and/or 12.1±0.2.

13. The formulation according to claim 1, wherein the particles are contained within a sachet or a capsule.

14. The formulation according to claim 1, which is a paediatric formulation.

15. The pharmaceutical formulation of claim 1, wherein the coating layer comprises odevixibat agglomerates having a $d_{90}$ particle size distribution of less than 12 μm.

* * * * *